US009428749B2

(12) United States Patent
van Rooij et al.

(10) Patent No.: US 9,428,749 B2
(45) Date of Patent: Aug. 30, 2016

(54) CONTROL OF WHOLE BODY ENERGY HOMEOSTASIS BY MICRORNA REGULATION

(71) Applicants: THE BOARD OF REGENTS, THE UNIVERSITY OF TEXAS SYSTEM, Austin, TX (US); MIRAGEN THERAPEUTICS, INC., Boulder, CO (US)

(72) Inventors: Eva van Rooij, Utrecht (NL); Eric Olson, Dallas, TX (US); Chad Grueter, Richardson, TX (US); Rusty Montgomery, Boulder, CO (US)

(73) Assignees: THE BOARD OF REGENTS, THE UNIVERSITY OF TEXAS SYSTEM, Austin, TX (US); MIRAGEN THERAPEUTICS, INC., Boulder, CO (US)

( * ) Notice: Subject to any disclaimer, the term of this patent is extended or adjusted under 35 U.S.C. 154(b) by 30 days.

(21) Appl. No.: 14/350,027

(22) PCT Filed: Oct. 9, 2012

(86) PCT No.: PCT/US2012/059349
§ 371 (c)(1),
(2) Date: Aug. 6, 2014

(87) PCT Pub. No.: WO2013/052965
PCT Pub. Date: Apr. 11, 2013

(65) Prior Publication Data
US 2014/0303236 A1    Oct. 9, 2014

Related U.S. Application Data

(60) Provisional application No. 61/544,187, filed on Oct. 6, 2011, provisional application No. 61/638,345, filed on Apr. 25, 2012.

(51) Int. Cl.
C12N 15/11        (2006.01)
C12N 15/113       (2010.01)

(52) U.S. Cl.
CPC ....... C12N 15/113 (2013.01); *C12N 2310/113* (2013.01); *C12N 2310/315* (2013.01); *C12N 2310/3231* (2013.01)

(58) Field of Classification Search
CPC .......................... C12N 15/113; C12N 2310/14
See application file for complete search history.

(56) References Cited

U.S. PATENT DOCUMENTS

| 6,632,628 | B1  | 10/2003 | Olson et al. |
| 7,232,806 | B2  | 6/2007  | Tuschl et al. |
| 7,687,617 | B2  | 3/2010  | Thrue et al. |
| 8,222,221 | B2  | 7/2012  | Corey et al. |
| 8,304,397 | B2  | 11/2012 | Olson et al. |
| 8,481,507 | B2  | 7/2013  | Olson et al. |
| 8,629,119 | B2  | 1/2014  | Olson et al. |
| 8,642,751 | B2  | 2/2014  | Dalby et al. |
| 8,716,258 | B2* | 5/2014  | Olson ................. C12N 15/113 514/44 A |
| 8,962,588 | B2* | 2/2015  | Olson ................. A61K 31/7105 514/44 A |
| 2004/0127443 | A1 | 7/2004  | Pershadsingh |
| 2004/0157790 | A1 | 8/2004  | Herweijer et al. |
| 2005/0059005 | A1 | 3/2005  | Tuschl et al. |
| 2005/0075492 | A1 | 4/2005  | Chen et al. |
| 2005/0124568 | A1 | 6/2005  | Usman et al. |
| 2005/0261218 | A1 | 11/2005 | Esau et al. |
| 2006/0019286 | A1 | 1/2006  | Horvitz et al. |
| 2006/0185027 | A1 | 8/2006  | Bartel et al. |
| 2007/0287179 | A1 | 12/2007 | Tuschl et al. |
| 2007/0292878 | A1 | 12/2007 | Raymond |
| 2008/0050744 | A1 | 2/2008  | Brown et al. |
| 2008/0176766 | A1 | 7/2008  | Brown et al. |
| 2008/0214437 | A1 | 9/2008  | Mohapatra et al. |
| 2009/0105174 | A1 | 4/2009  | Jayasena |
| 2009/0137504 | A1 | 5/2009  | Echwald et al. |
| 2009/0143326 | A1 | 6/2009  | Obad et al. |
| 2009/0180957 | A1 | 7/2009  | Olson et al. |
| 2009/0286969 | A1 | 11/2009 | Esau et al. |
| 2009/0291906 | A1 | 11/2009 | Esau et al. |
| 2009/0291907 | A1 | 11/2009 | Esau et al. |

(Continued)

FOREIGN PATENT DOCUMENTS

EP    1959012 A2    8/2008
EP    2113567 A1    11/2009

(Continued)

OTHER PUBLICATIONS

Diseases and Conditions Metabolic syndrome by Mayo Clinic Staff, Aug. 22, 1014, pp. 1-2, retrieved on Nov. 2, 2015 from www.mayoclinic.org/diseases-conditions/metabolic syndrome/bascis/symptoms.*
van Rooij et al. Cell 24, 2008, pp. 159-166.*
Agrawal et al., "Antisense therapeutics: is it as simple as complementary base recognition?" Molecular Med. Today, vol. 6, pp. 72-81 (2000).
Anselmino et al., "Implications of abnormal glucose metabolism in patients with coronary artery disease," Diab. Vasc. Dis. Res. 5(4):285-290 (2008).
Chirila et al., "The use of synthetic polymers for delivery of therapeutic antisense oligodeoxynucleotides," Biomaterials, vol. 23, pp. 321-342 (2002).

(Continued)

*Primary Examiner* — Brian Whiteman
(74) *Attorney, Agent, or Firm* — Cooley LLP

(57) ABSTRACT

The disclosure provides a method of regulating fatty acid or glucose metabolism in a cell by contacting the cell with a modulator of miR-208a and/or miR-208b activity or expression. The disclosure also provides a method of treating or preventing a metabolic disorder, such as obesity, diabetes, or metabolic syndrome, in a subject by administering to the subject an inhibitor of miR-208a and/or miR-208b activity or expression. Also provided is a method of enhancing or improving mitochondrial function and/or redox-homeostasis in a subject by administering to the subject an inhibitor of miR-208a and/or miR-208b activity or expression.

19 Claims, 10 Drawing Sheets

(56) References Cited

U.S. PATENT DOCUMENTS

| | | |
|---|---|---|
| 2009/0293148 A1 | 11/2009 | Ren et al. |
| 2009/0326049 A1 | 12/2009 | Aristarkhov et al. |
| 2010/0004320 A1 | 1/2010 | Elmen et al. |
| 2010/0029003 A1 | 2/2010 | Bartel et al. |
| 2010/0173288 A1 | 7/2010 | Zhang et al. |
| 2010/0210712 A1 | 8/2010 | Hansen et al. |
| 2010/0269183 A1 | 10/2010 | Olson et al. |
| 2010/0280094 A1 | 11/2010 | Beuvink et al. |
| 2010/0292297 A1* | 11/2010 | Wang ............... C12N 15/113 514/44 A |
| 2010/0298410 A1 | 11/2010 | Obad et al. |
| 2011/0020345 A1 | 1/2011 | Herring et al. |
| 2011/0071211 A1 | 3/2011 | Thum et al. |
| 2011/0098338 A1 | 4/2011 | Hajjar et al. |
| 2011/0105593 A1 | 5/2011 | Steel et al. |
| 2011/0117560 A1 | 5/2011 | Spinale et al. |
| 2011/0152352 A1 | 6/2011 | Hata et al. |
| 2011/0160285 A1 | 6/2011 | Anderson et al. |
| 2011/0224277 A1 | 9/2011 | Esau et al. |
| 2011/0294869 A1 | 12/2011 | Petersen |
| 2011/0313019 A1 | 12/2011 | Swayze et al. |
| 2012/0035243 A1 | 2/2012 | Olson et al. |
| 2012/0041052 A1 | 2/2012 | Beuvink et al. |
| 2012/0083596 A1 | 4/2012 | Elmén et al. |
| 2012/0114744 A1 | 5/2012 | Beuvink et al. |
| 2012/0172416 A1 | 7/2012 | Velin et al. |
| 2012/0184596 A1 | 7/2012 | Dalby et al. |
| 2012/0322851 A1 | 12/2012 | Hardee et al. |
| 2013/0078225 A1 | 3/2013 | Zeng et al. |
| 2013/0079505 A1 | 3/2013 | Moeller et al. |
| 2013/0096290 A1 | 4/2013 | Brown |
| 2013/0109738 A1 | 5/2013 | Chang et al. |
| 2013/0137753 A1 | 5/2013 | Samant et al. |
| 2013/0150256 A1 | 6/2013 | Synnergren et al. |
| 2013/0156845 A1 | 6/2013 | Manoharan et al. |
| 2013/0157883 A1 | 6/2013 | Keller et al. |
| 2013/0171242 A1 | 7/2013 | Lim et al. |
| 2014/0187603 A1 | 7/2014 | Dalby et al. |

FOREIGN PATENT DOCUMENTS

| | | | |
|---|---|---|---|
| EP | | 2194129 A2 | 6/2010 |
| EP | | 2208798 A1 | 7/2010 |
| EP | | 2388327 A1 | 11/2011 |
| EP | | 2388328 A1 | 11/2011 |
| EP | | 2447274 A2 | 5/2012 |
| EP | | 2205737 B1 | 2/2013 |
| EP | | 2559442 A1 | 2/2013 |
| EP | | 2604690 A1 | 6/2013 |
| EP | | 2610342 A1 | 7/2013 |
| WO | WO 2005/013901 | A2 | 2/2005 |
| WO | WO 2005/017145 | A1 | 2/2005 |
| WO | WO 2005/078096 | A2 | 8/2005 |
| WO | WO 2005/078139 | A2 | 8/2005 |
| WO | WO 2005/079397 | A2 | 9/2005 |
| WO | WO 2005/118806 | A2 | 12/2005 |
| WO | WO 2006/063356 | A1 | 6/2006 |
| WO | WO 2006/111512 | A1 | 10/2006 |
| WO | WO 2006/137941 | A2 | 12/2006 |
| WO | WO 2007/000668 | A2 | 1/2007 |
| WO | WO 2007/070483 | A2 | 6/2007 |
| WO | WO 2007/090073 | A2 | 8/2007 |
| WO | WO 2007/112754 | A2 | 10/2007 |
| WO | WO 2008/016924 | A2 | 2/2008 |
| WO | WO 2008/042231 | A2 | 4/2008 |
| WO | WO 2008/043521 | A2 | 4/2008 |
| WO | WO 2008/061537 | A2 | 5/2008 |
| WO | WO 2008/074328 | A2 | 6/2008 |
| WO | WO 2008/076324 | A2 | 6/2008 |
| WO | WO 2008/147839 | A1 | 12/2008 |
| WO | WO 2009/018492 | A2 | 2/2009 |
| WO | WO 2009/026576 | A1 | 2/2009 |
| WO | WO 2009/043353 | A2 | 4/2009 |
| WO | WO 2009/058818 | A2 | 5/2009 |
| WO | WO 2009/062169 | A2 | 5/2009 |
| WO | WO 2009/114681 | A2 | 9/2009 |
| WO | WO 2009/149182 | A1 | 12/2009 |
| WO | WO 2010/048585 | A2 | 4/2010 |
| WO | WO 2010/091204 | A1 | 8/2010 |
| WO | WO 2010/144485 | A1 | 12/2010 |
| WO | WO 2011/139911 | A2 | 11/2011 |
| WO | WO 2011/154553 | A2 | 12/2011 |
| WO | WO 2011/158191 | A1 | 12/2011 |
| WO | WO 2012/006577 | A2 | 1/2012 |
| WO | WO 2012/020307 | A2 | 2/2012 |
| WO | WO 2012/027206 | A1 | 3/2012 |
| WO | WO 2012/149646 | A1 | 11/2012 |
| WO | WO 2013/052965 | A2 | 4/2013 |
| WO | WO 2013/054113 | A1 | 4/2013 |
| WO | WO 2013/057527 | A2 | 4/2013 |
| WO | WO 2013/059496 | A1 | 4/2013 |
| WO | WO 2013/087907 | A1 | 6/2013 |
| WO | WO 2013/088338 | A1 | 6/2013 |
| WO | WO 2013/090457 | A2 | 6/2013 |

OTHER PUBLICATIONS

Crooke, S., "Progress in Antisense Technology," Annu. Rev. Medicine, vol. 55, pp. 61-95 (2004).

Fichtlscherer et al., "Circulating MicroRNAs in Patients With Coronary Artery Disease," Circ. Res. 107(5):677-684 (2010).

Fichtlscherer et al., "Circulating MicroRNAs. Biomarkers or Mediators of Cardiovascular Diseases?" Arterioscler. Thromb. Vasc. Biol. 31(11):2383-2390 (2011).

International Search Report and Written Opinion for PCT/US2007/074866, 14 pages (mailed Jun. 20, 2008).

International Preliminary Report on Patentability, PCT appl..No. PCT/US2011/065121, 9 pages (Jun. 18, 2013).

International Preliminary Report on Patentability, PCT appl. No. PCT/US2012/059349, 10 pages (Apr. 8, 2014).

International Search Report, PCT appl..No. PCT/US2011/065121, 5 pages (Jun. 5, 2012).

International Search Report, PCT appl. No. PCT/US2012/059349, 8 pages (Apr. 1, 2013).

Jang et al., "Gene delivery from polymer scaffolds for tissue engineering," Expert Rev. Medical Devices, vol. 1, No. 1, pp. 127-138 (2004).

Krutzfeldt, J., et al. (2005) Silencing of microRNAs in vivo with 'antagomirs'. Nature, v.438, pp. 685-689.

Lagos-Quintana et al., "Identification of tissue-specific microRNAs from mouse," Current Biology, vol. 12:735-739, 2002.

Lagos-Quintana et al., "New microRNAs from mouse and human," RNA, vol. 9:175-179, 2003.

Montgomery et al., "Therapeutic Inhibition of miR-208a Improves Cardiac Function and Survival During Heart Failue," Circ. 124(14):1537-1547, Supplemental Material (2011).

Myocardial Infarction definition [online]. [retrieved on Feb. 23, 2012]. Retrieved from the Internet: <http://www.credoreference.com/entry.do?id=6584661 >.

Opalinska et al., "Nucleic-Acid Therapeutics: Basic Principles and Recent Applications," Nature Rev., vol. 1, pp. 503-514 (2002).

Peracchi et al., "Prospects for antiviral ribozymes and deoxyribozymes," Rev. Med. Virol., vol. 14, pp. 47-64 (2004).

Sempere et al., "Expression profiling of mammalian microRNAs uncovers a subset of brain-expressed microRNAs with possible roles in murine and human neuronal differentiation," Genome Biology, vol. 5:R13, 2004.

Written Opinion of the International Searching Authority, PCT appl. No. PCT/US2011/065121, 8 pages (Jun. 5, 2012).

Written Opinion of the International Searching Authority, PCT appl. No. PCT/US2012/059349, 9 pages (Apr. 1, 2013).

Poy et al., "microRNAs and the regulation of glucose and lipid metabolism," Diab. Obes. Metab. 9(Suppl. 2):67-73 (2007).

Supplementary European Search Report, EP appl. No. 128389117, 3 pages (Apr. 8, 2015).

Tavintharan et al., "Riboregulators and Metabolic Disorders: Getting Closer Towards Understanding the Pathogenesis of Diabetes Mellitus?" Curr. Molec. Med. 9:281-286 (2009).

* cited by examiner p<0.05 vs. Saline
*p<0.05 vs. M-10591

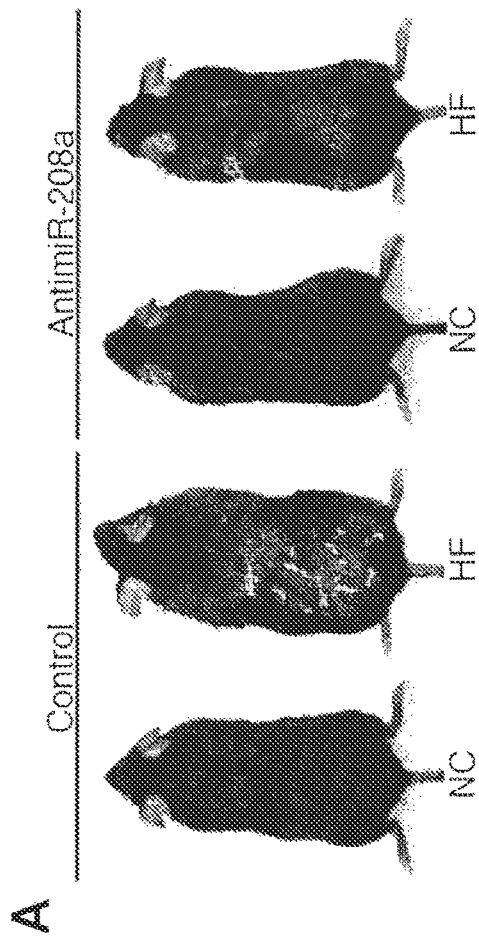
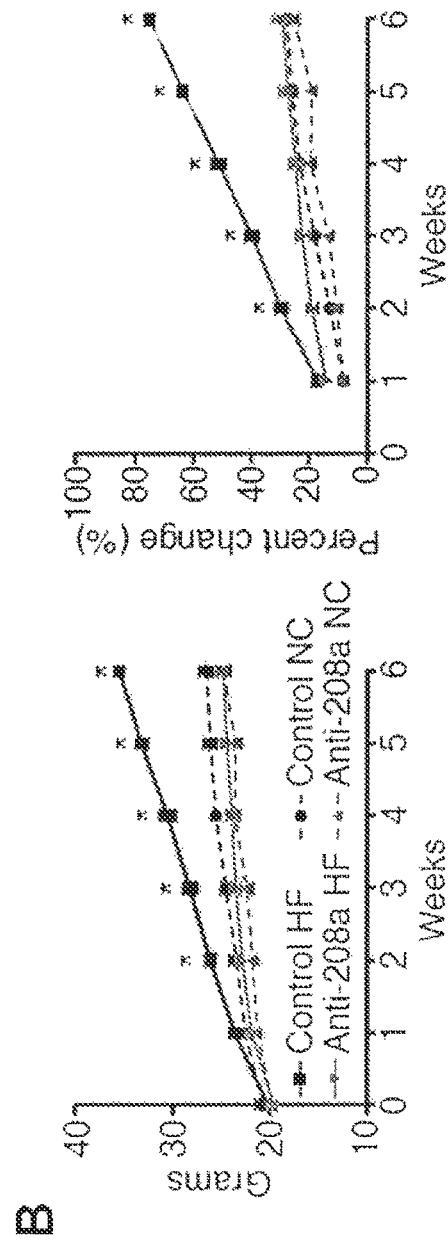
FIGURE 4A-B

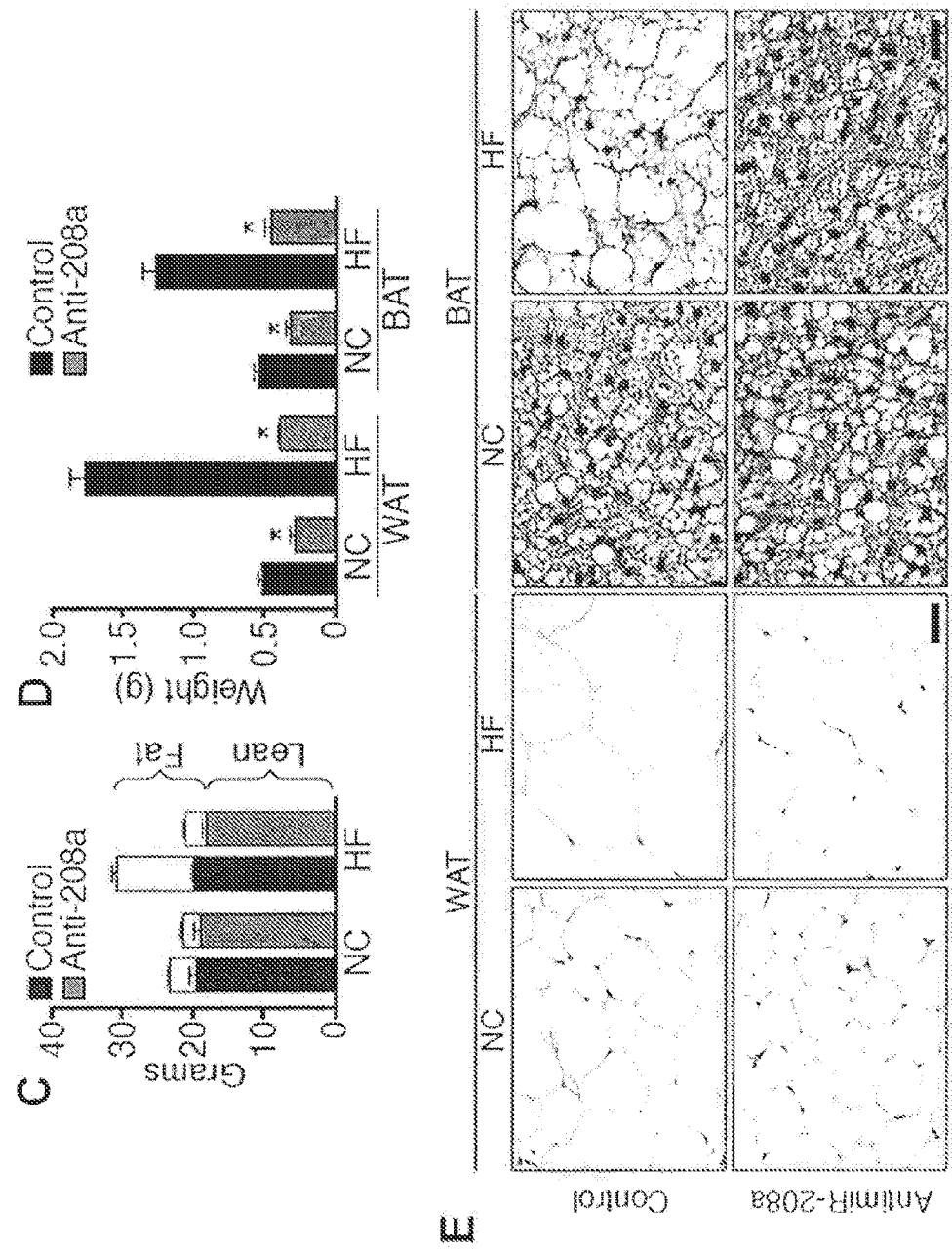
FIGURE 4C-E

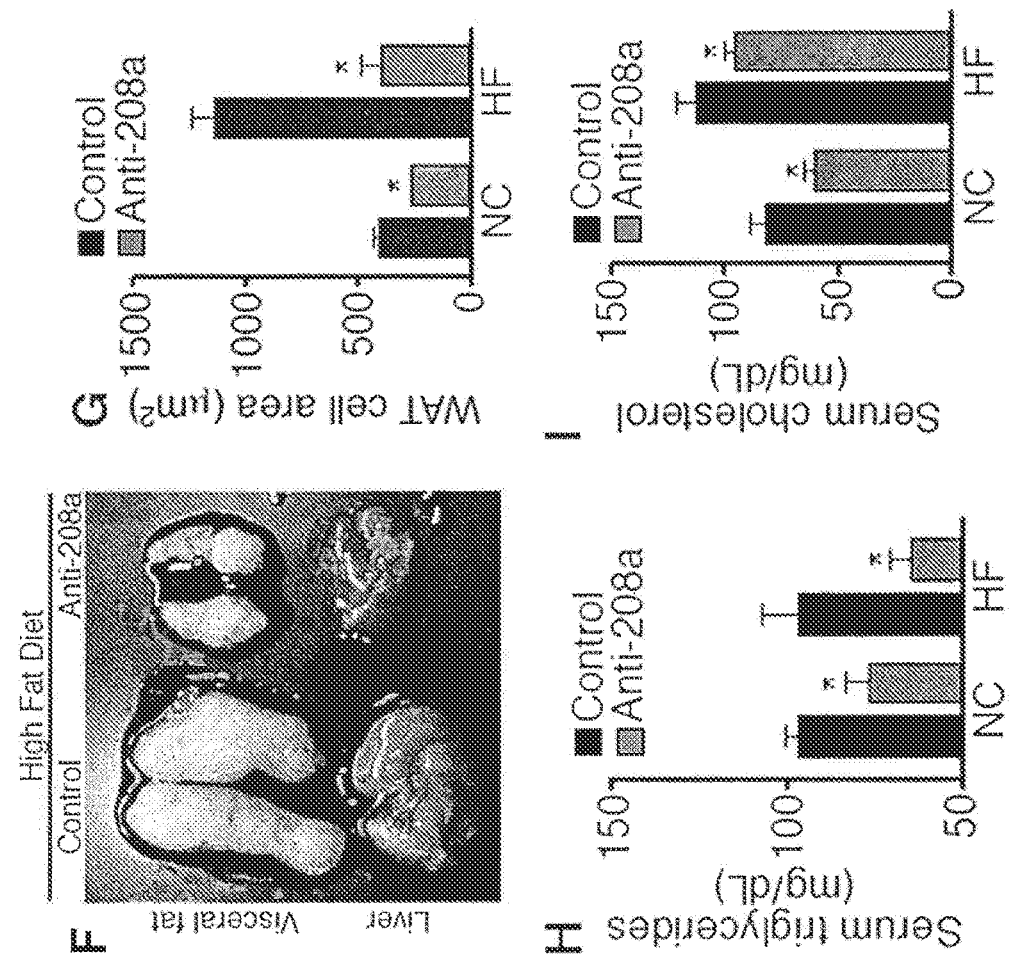
FIGURE 4F-I

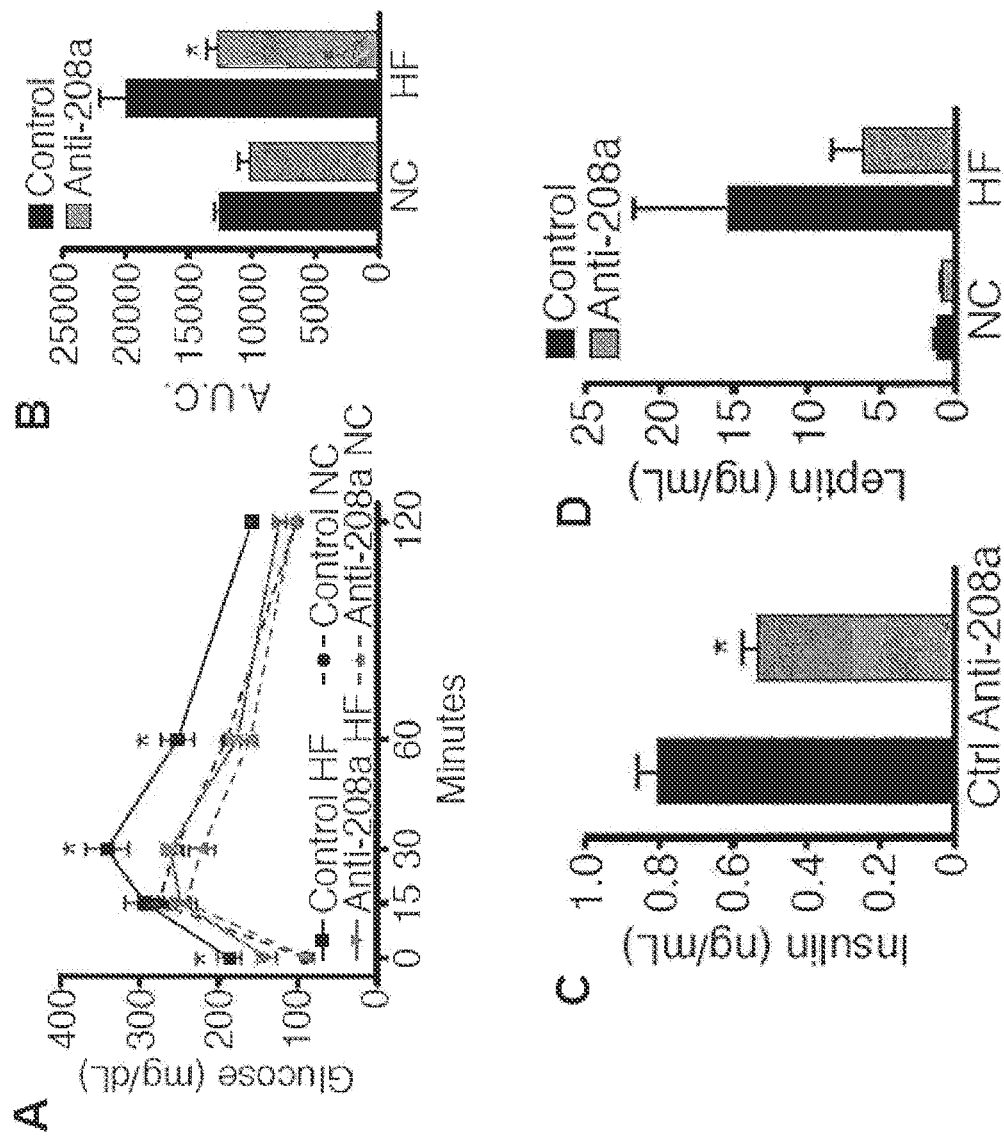
FIGURE 5A-D

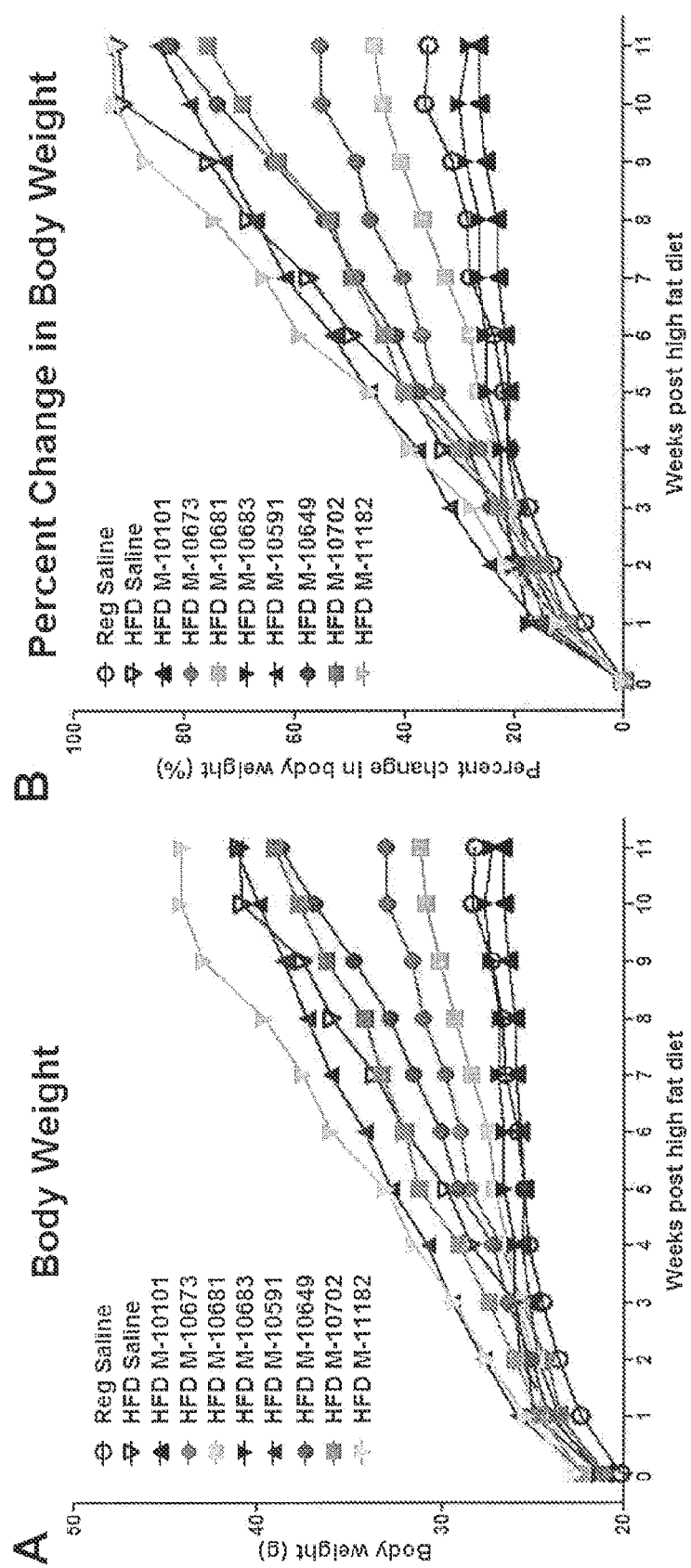
FIGURE 6A-B

SEQUENCE LISTING

```
<160> NUMBER OF SEQ ID NOS: 99

<210> SEQ ID NO 1
<211> LENGTH: 11
<212> TYPE: DNA
<213> ORGANISM: Unknown
<220> FEATURE:
<223> OTHER INFORMATION: miR-208a or miR-208b antisense oligonucleotide

<400> SEQUENCE: 1
tgctcgtctt a                                                        11

<210> SEQ ID NO 2
<211> LENGTH: 11
<212> TYPE: DNA
<213> ORGANISM: Unknown
<220> FEATURE:
<223> OTHER INFORMATION: miR-208a or miR-208b antisense oligonucleotide

<400> SEQUENCE: 2
tgttcgtctt a                                                        11

<210> SEQ ID NO 3
<211> LENGTH: 16
<212> TYPE: DNA
<213> ORGANISM: Unknown
<220> FEATURE:
<223> OTHER INFORMATION: miR-208a or miR-208b antisense oligonucleotide

<400> SEQUENCE: 3 cttttgctc gtctta                                                   16

<210> SEQ ID NO 4
<211> LENGTH: 16
<212> TYPE: DNA
<213> ORGANISM: Unknown
<220> FEATURE:
<223> OTHER INFORMATION: miR-208a or miR-208b antisense oligonucleotide

<400> SEQUENCE: 4
ccttttgttc gtctta                                                  16
```

```
<210> SEQ ID NO 5
<211> LENGTH: 71
<212> TYPE: DNA
<213> ORGANISM: Homo sapiens

<400> SEQUENCE: 5
acgggcgagc ttttggcccg ggttatacct gatgctcacg tataagacga gcaaaaagct    60
tgttggtcag a                                                         71

<210> SEQ ID NO 6
<211> LENGTH: 71
<212> TYPE: DNA
<213> ORGANISM: Mus sp.

<400> SEQUENCE: 6
acgggtgagc ttttggcccg ggttatacct gactctcacg tataagacga gcaaaaagct    60
tgttggtcag a                                                         71

<210> SEQ ID NO 7
<211> LENGTH: 71
<212> TYPE: DNA
<213> ORGANISM: Rattus sp.

<400> SEQUENCE: 7
acgggtgagc ttttggcccg ggttatacct gactctcacg tataagacga gcaaaaagct    60
tgttggtcag a                                                         71

<210> SEQ ID NO 8
<211> LENGTH: 71
<212> TYPE: DNA
<213> ORGANISM: Canis sp.

<400> SEQUENCE: 8
acgcatgagc ttttggctcg ggttatacct gatgctcacg tataagacga gcaaaaagct    60
tgttggtcag a                                                         71

<210> SEQ ID NO 9
<211> LENGTH: 22
<212> TYPE: RNA
<213> ORGANISM: Unknown
<220> FEATURE:
<223> OTHER INFORMATION: mature miR-208a

<400> SEQUENCE: 9
auaagacgag caaaaagcuu gu                                              22

<210> SEQ ID NO 10
<211> LENGTH: 43
<212> TYPE: DNA
<213> ORGANISM: Unknown
<220> FEATURE:
<223> OTHER INFORMATION: pre-miR-208b

<400> SEQUENCE: 10
tttctgatcc gaatataaga cgaacaaaag gtttgtctga ggg                      43

<210> SEQ ID NO 11
<211> LENGTH: 22
<212> TYPE: RNA
<213> ORGANISM: Unknown
<220> FEATURE:
<223> OTHER INFORMATION: mature miR-208b
```

<400> SEQUENCE: 11
auaagacgaa caaaagguuu gu                                          22

<210> SEQ ID NO 12
<211> LENGTH: 16
<212> TYPE: DNA
<213> ORGANISM: Caenorhabditis elegans

<400> SEQUENCE: 12
tcctagaaag agtaga                                                 16

<210> SEQ ID NO 13
<211> LENGTH: 16
<212> TYPE: DNA
<213> ORGANISM: Artificial Sequence
<220> FEATURE:
<223> OTHER INFORMATION: 208a_DNA_LNA_16_PS oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate -continued

```
         cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 13 cttttgctc gtctta                                                    16

<210> SEQ ID NO 14
<211> LENGTH: 11
<212> TYPE: DNA
<213> ORGANISM: Artificial Sequence
<220> FEATURE:
<223> OTHER INFORMATION: 208fam_optdes1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      cytidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 14
```
tgctcgtctt a                                                                    11

<210> SEQ ID NO 15
<211> LENGTH: 11
<212> TYPE: DNA
<213> ORGANISM: Artificial Sequence
<220> FEATURE:
<223> OTHER INFORMATION: 208fam_optdes2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      cytidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 15
tgctcgtctt a                                                                    11

<210> SEQ ID NO 16
<211> LENGTH: 11
<212> TYPE: DNA
<213> ORGANISM: Artificial Sequence
<220> FEATURE:
<223> OTHER INFORMATION: 208fam_optdes3 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES -continued

```
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      cytidine
<220> FEATURE:
<221> NAME/KEY: MOD_RES
<222> LOCATION: (4)..(4)
<223> OTHER INFORMATION: May be a phosphorothioate adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 16
tgcacgtctt a                                                          11

<210> SEQ ID NO 17
<211> LENGTH: 11
<212> TYPE: DNA
<213> ORGANISM: Artificial Sequence
<220> FEATURE:
<223> OTHER INFORMATION: 208fam_optdes4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      guanosine
<220> FEATURE:
<221> NAME/KEY: MOD_RES
<222> LOCATION: (3)..(3)
<223> OTHER INFORMATION: May be a phosphorothioate cytidine
<220> FEATURE:
<221> NAME/KEY: MOD_RES
<222> LOCATION: (4)..(4)
<223> OTHER INFORMATION: May be a phosphorothioate adenosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
```

<221> NAME/KEY: MOD_RES
<222> LOCATION: (6)..(6)
<223> OTHER INFORMATION: May be a locked nucleic acid phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 17
tgcacgtctt a                                                          11

<210> SEQ ID NO 18
<211> LENGTH: 16
<212> TYPE: DNA
<213> ORGANISM: Artificial Sequence
<220> FEATURE:
<223> OTHER INFORMATION: 208a LNA C_T_DNA_16_1 oligonucleotide
<220> FEATURE:
<221> NAME/KEY: MOD_RES
<222> LOCATION: (1)..(1)
<223> OTHER INFORMATION: May be a locked nucleic acid phosphorothioate cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate thymidine
<220> FEATURE:
<221> NAME/KEY: MOD_RES
<222> LOCATION: (4)..(4)
<223> OTHER INFORMATION: May be a locked nucleic acid phosphorothioate thymidine
<220> FEATURE:
<221> NAME/KEY: MOD_RES
<222> LOCATION: (5)..(5)
<223> OTHER INFORMATION: May be a locked nucleic acid phosphorothioate thymidine
<220> FEATURE:
<221> NAME/KEY: MOD_RES
<222> LOCATION: (6)..(6)
<223> OTHER INFORMATION: May be a locked nucleic acid phosphorothioate thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate cytidine
<220> FEATURE:
<221> NAME/KEY: MOD_RES
<222> LOCATION: (9)..(9)

```
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 18 cttttgctc gtctta                                                    16

<210> SEQ ID NO 19
<211> LENGTH: 16
<212> TYPE: DNA
<213> ORGANISM: Artificial Sequence
<220> FEATURE:
<223> OTHER INFORMATION: 208a_ LNA C_T_DNA_16_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
```

```
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 19 cttttttgctc gtctta                                                      16

<210> SEQ ID NO 20
<211> LENGTH: 16
<212> TYPE: DNA
<213> ORGANISM: Artificial Sequence
<220> FEATURE:
<223> OTHER INFORMATION: 208a_ LNA C_T_DNA_16_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
```

```
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 20 cttttttgctc gtctta                                                      16

<210> SEQ ID NO 21
<211> LENGTH: 16
<212> TYPE: DNA
<213> ORGANISM: Artificial Sequence
<220> FEATURE:
<223> OTHER INFORMATION: 208_LNA_opt_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
```

```
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 21 cttttttgctc gtctta                                                 16

<210> SEQ ID NO 22
<211> LENGTH: 16
<212> TYPE: DNA
<213> ORGANISM: Artificial Sequence
<220> FEATURE:
<223> OTHER INFORMATION: 208_LNA_opt_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
```

<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 22 cttttgctc gtctta                                               16

<210> SEQ ID NO 23
<211> LENGTH: 16
<212> TYPE: DNA
<213> ORGANISM: Artificial Sequence
<220> FEATURE:
<223> OTHER INFORMATION: 208_LNA_opt_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:

```
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 23 cttttttgctc gtctta                                                      16

<210> SEQ ID NO 24
<211> LENGTH: 16
<212> TYPE: DNA
<213> ORGANISM: Artificial Sequence
<220> FEATURE:
<223> OTHER INFORMATION: 208_LNA_opt_4 oligonucleotide
```

```
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a phosphorothioate cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 24 cttttgctc gtctta                                                      16

<210> SEQ ID NO 25
```

```
<211> LENGTH: 16
<212> TYPE: DNA
<213> ORGANISM: Artificial Sequence
<220> FEATURE:
<223> OTHER INFORMATION: 208_LNA_opt_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      guanosine
<220> FEATURE:
<221> NAME/KEY: MOD_RES
<222> LOCATION: (8)..(8)
<223> OTHER INFORMATION: May be a phosphorothioate cytidine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 25
``` cttttttgctc gtctta                                          16

<210> SEQ ID NO 26
<211> LENGTH: 16
<212> TYPE: DNA
<213> ORGANISM: Artificial Sequence
<220> FEATURE:
<223> OTHER INFORMATION: 208b_DNA_LNA_16_PS oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:

<221> NAME/KEY: MOD_RES
<222> LOCATION: (16)..(16)
<223> OTHER INFORMATION: May be a locked nucleic acid adenosine

<400> SEQUENCE: 26
ccttttgttc gtctta                                                   16

<210> SEQ ID NO 27
<211> LENGTH: 15
<212> TYPE: DNA
<213> ORGANISM: Artificial Sequence
<220> FEATURE:
<223> OTHER INFORMATION: 208a like_15_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate

```
              thymidine
<220> FEATURE:
<221> NAME/KEY: MOD_RES
<222> LOCATION: (15)..(15)
<223> OTHER INFORMATION: May be a deoxy adenosine

<400> SEQUENCE: 27
tttttgctcg tctta                                                          15

<210> SEQ ID NO 28
<211> LENGTH: 15
<212> TYPE: DNA
<213> ORGANISM: Artificial Sequence
<220> FEATURE:
<223> OTHER INFORMATION: 208a like_15_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
```

<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 28
tttttgctcg tctta                                                            15

<210> SEQ ID NO 29
<211> LENGTH: 15
<212> TYPE: DNA
<213> ORGANISM: Artificial Sequence
<220> FEATURE:
<223> OTHER INFORMATION: 208a like_15_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:

```
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 29
tttttgctcg tctta                                                      15

<210> SEQ ID NO 30
<211> LENGTH: 15
<212> TYPE: DNA
<213> ORGANISM: Artificial Sequence
<220> FEATURE:
<223> OTHER INFORMATION: 208a like_15_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a locked nucleic acid phosphorothioate
```

```
            thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 30
tttttgctcg tctta                                                          15

<210> SEQ ID NO 31
<211> LENGTH: 15
<212> TYPE: DNA
<213> ORGANISM: Artificial Sequence
<220> FEATURE:
<223> OTHER INFORMATION: 208a like_15_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
```

-continued

```
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 31
tttttgctcg tctta                                                          15

<210> SEQ ID NO 32
<211> LENGTH: 15
<212> TYPE: DNA
<213> ORGANISM: Artificial Sequence
<220> FEATURE:
<223> OTHER INFORMATION: 208a like_15_6 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
```

```
           cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 32
tttttgctcg tctta                                                      15

<210> SEQ ID NO 33
<211> LENGTH: 15
<212> TYPE: DNA
<213> ORGANISM: Artificial Sequence
<220> FEATURE:
<223> OTHER INFORMATION: 208b like_15_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
```

```
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 33
cttttgctcg tctta                                                        15

<210> SEQ ID NO 34
<211> LENGTH: 15
<212> TYPE: DNA
<213> ORGANISM: Artificial Sequence
<220> FEATURE:
<223> OTHER INFORMATION: 208b like_15_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
```

```
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 34
cttttgctcg tctta                                                          15

<210> SEQ ID NO 35
<211> LENGTH: 15
<212> TYPE: DNA
<213> ORGANISM: Artificial Sequence
<220> FEATURE:
<223> OTHER INFORMATION: 208b like_15_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
```

```
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 35
cttttgctcg tctta                                                     15

<210> SEQ ID NO 36
<211> LENGTH: 15
<212> TYPE: DNA
<213> ORGANISM: Artificial Sequence
<220> FEATURE:
<223> OTHER INFORMATION: 208b like_15_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
```

```
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 36
cttttgctcg tctta                                                    15

<210> SEQ ID NO 37
<211> LENGTH: 15
<212> TYPE: DNA
<213> ORGANISM: Artificial Sequence
<220> FEATURE:
<223> OTHER INFORMATION: 208b like_15_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
```

<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 37
cttttgctcg tctta                                                        15

<210> SEQ ID NO 38
<211> LENGTH: 15
<212> TYPE: DNA
<213> ORGANISM: Artificial Sequence
<220> FEATURE:
<223> OTHER INFORMATION: 208b like_15_6 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES

```
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 38
cttttgctcg tctta                                                     15

<210> SEQ ID NO 39
<211> LENGTH: 15
<212> TYPE: DNA
<213> ORGANISM: Artificial Sequence
<220> FEATURE:
<223> OTHER INFORMATION: 208b_15_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
```

```
            cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 39
cttttgttcg tctta                                                      15

<210> SEQ ID NO 40
<211> LENGTH: 15
<212> TYPE: DNA
<213> ORGANISM: Artificial Sequence
<220> FEATURE:
<223> OTHER INFORMATION: 208b _15_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
```

<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 40
cttttgttcg tctta                                                      15

<210> SEQ ID NO 41
<211> LENGTH: 15
<212> TYPE: DNA
<213> ORGANISM: Artificial Sequence
<220> FEATURE:
<223> OTHER INFORMATION: 208b_15_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate thymidine

```
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a phosphorothioate guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a deoxy adenosine

<400> SEQUENCE: 41
cttttgttcg tctta                                                        15

<210> SEQ ID NO 42
<211> LENGTH: 15
<212> TYPE: DNA
<213> ORGANISM: Artificial Sequence
<220> FEATURE:
<223> OTHER INFORMATION: 208a like_15_7 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
<222> LOCATION: (8)..(8)
<223> OTHER INFORMATION: May be a phosphorothioate thymidine
```

```
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 42
tttttgctcg tctta                                                          15

<210> SEQ ID NO 43
<211> LENGTH: 15
<212> TYPE: DNA
<213> ORGANISM: Artificial Sequence
<220> FEATURE:
<223> OTHER INFORMATION: 208b like_15_7 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate cytidine
<220> FEATURE:
<221> NAME/KEY: MOD_RES
```

```
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 43
cttttgctcg tctta                                                  15

<210> SEQ ID NO 44
<211> LENGTH: 15
<212> TYPE: DNA
<213> ORGANISM: Artificial Sequence
<220> FEATURE:
<223> OTHER INFORMATION: 208b_15_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
```

```
<220> FEATURE:
<221> NAME/KEY: MOD_RES
<222> LOCATION: (8)..(8)
<223> OTHER INFORMATION: May be a phosphorothioate thymidine
<220> FEATURE:
<221> NAME/KEY: MOD_RES
<222> LOCATION: (9)..(9)
<223> OTHER INFORMATION: May be a locked nucleic acid phosphorothioate
      cytidine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid adenosine

<400> SEQUENCE: 44
cttttgttcg tctta                                                   15

<210> SEQ ID NO 45
<211> LENGTH: 14
<212> TYPE: DNA
<213> ORGANISM: Artificial Sequence
<220> FEATURE:
<223> OTHER INFORMATION: 208a like_14_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      cytidine
```

```
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a deoxy adenosine

<400> SEQUENCE: 45
ttttgctcgt ctta                                                       14

<210> SEQ ID NO 46
<211> LENGTH: 14
<212> TYPE: DNA
<213> ORGANISM: Artificial Sequence
<220> FEATURE:
<223> OTHER INFORMATION: 208a like_14_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
```

```
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 46
ttttgctcgt ctta                                                        14

<210> SEQ ID NO 47
<211> LENGTH: 14
<212> TYPE: DNA
<213> ORGANISM: Artificial Sequence
<220> FEATURE:
<223> OTHER INFORMATION: 208a like_14_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
```

```
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 47
ttttgctcgt ctta                                                         14

<210> SEQ ID NO 48
<211> LENGTH: 14
<212> TYPE: DNA
<213> ORGANISM: Artificial Sequence
<220> FEATURE:
<223> OTHER INFORMATION: 208a like_14_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
```

```
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 48
ttttgctcgt ctta                                                         14

<210> SEQ ID NO 49
<211> LENGTH: 14
<212> TYPE: DNA
<213> ORGANISM: Artificial Sequence
<220> FEATURE:
<223> OTHER INFORMATION: 208a like_14_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate cytidine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
```

```
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a phosphorothioate cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a deoxy adenosine

<400> SEQUENCE: 49
ttttgctcgt ctta                                                      14

<210> SEQ ID NO 50
<211> LENGTH: 14
<212> TYPE: DNA
<213> ORGANISM: Artificial Sequence
<220> FEATURE:
<223> OTHER INFORMATION: 208a like_14_6 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      cytidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      guanosine
<220> FEATURE:
<221> NAME/KEY: MOD_RES
<222> LOCATION: (10)..(10)
```

```
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 50
ttttgctcgt ctta                                                           14

<210> SEQ ID NO 51
<211> LENGTH: 14
<212> TYPE: DNA
<213> ORGANISM: Artificial Sequence
<220> FEATURE:
<223> OTHER INFORMATION: 208b_14_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
```

```
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a deoxy adenosine

<400> SEQUENCE: 51
ttttgttcgt ctta                                                            14

<210> SEQ ID NO 52
<211> LENGTH: 14
<212> TYPE: DNA
<213> ORGANISM: Artificial Sequence
<220> FEATURE:
<223> OTHER INFORMATION: 208b_14_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
```

<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 52
ttttgttcgt ctta                                                        14

<210> SEQ ID NO 53
<211> LENGTH: 14
<212> TYPE: DNA
<213> ORGANISM: Artificial Sequence
<220> FEATURE:
<223> OTHER INFORMATION: 208b_14_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES -continued

```
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 53
ttttgttcgt ctta                                                    14

<210> SEQ ID NO 54
<211> LENGTH: 14
<212> TYPE: DNA
<213> ORGANISM: Artificial Sequence
<220> FEATURE:
<223> OTHER INFORMATION: 208b_14_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
```

<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid adenosine

<400> SEQUENCE: 54
ttttgttcgt ctta                                                        14

<210> SEQ ID NO 55
<211> LENGTH: 14
<212> TYPE: DNA
<213> ORGANISM: Artificial Sequence
<220> FEATURE:
<223> OTHER INFORMATION: 208b_14_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a phosphorothioate cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)

<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a deoxy adenosine

<400> SEQUENCE: 55
ttttgttcgt ctta                                                       14

<210> SEQ ID NO 56
<211> LENGTH: 14
<212> TYPE: DNA
<213> ORGANISM: Artificial Sequence
<220> FEATURE:
<223> OTHER INFORMATION: 208b_14_6 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      thymidine

```
<220> FEATURE:
<221> NAME/KEY: MOD_RES
<222> LOCATION: (14)..(14)
<223> OTHER INFORMATION: May be a locked nucleic acid adenosine

<400> SEQUENCE: 56
ttttgttcgt ctta                                                        14

<210> SEQ ID NO 57
<211> LENGTH: 13
<212> TYPE: DNA
<213> ORGANISM: Artificial Sequence
<220> FEATURE:
<223> OTHER INFORMATION: 208a like_13_1 oligonucleotide
<220> FEATURE:
<221> NAME/KEY: MOD_RES
<222> LOCATION: (1)..(1)
<223> OTHER INFORMATION: May be a locked nucleic acid phosphorothioate
     thymidine
<220> FEATURE:
<221> NAME/KEY: MOD_RES
<222> LOCATION: (2)..(2)
<223> OTHER INFORMATION: May be a locked nucleic acid phosphorothioate
     thymidine
<220> FEATURE:
<221> NAME/KEY: MOD_RES
<222> LOCATION: (3)..(3)
<223> OTHER INFORMATION: May be a locked nucleic acid phosphorothioate
     thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
     cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
     cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
     cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
     thymidine
<220> FEATURE:
<221> NAME/KEY: MOD_RES
<222> LOCATION: (13)..(13)
<223> OTHER INFORMATION: May be a deoxy adenosine

<400> SEQUENCE: 57
tttgctcgtc tta                                                         13
```

```
<210> SEQ ID NO 58
<211> LENGTH: 13
<212> TYPE: DNA
<213> ORGANISM: Artificial Sequence
<220> FEATURE:
<223> OTHER INFORMATION: 208a like_13_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 58
tttgctcgtc tta                                                        13

<210> SEQ ID NO 59
<211> LENGTH: 13
<212> TYPE: DNA
<213> ORGANISM: Artificial Sequence
<220> FEATURE:
<223> OTHER INFORMATION: 208a like_13_3 oligonucleotide
```

```
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 59
tttgctcgtc tta                                                          13

<210> SEQ ID NO 60
<211> LENGTH: 13
<212> TYPE: DNA
<213> ORGANISM: Artificial Sequence
<220> FEATURE:
<223> OTHER INFORMATION: 208a like_13_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
```

```
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 60
tttgctcgtc tta                                                          13

<210> SEQ ID NO 61
<211> LENGTH: 13
<212> TYPE: DNA
<213> ORGANISM: Artificial Sequence
<220> FEATURE:
<223> OTHER INFORMATION: 208b_13_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
```

```
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a deoxy adenosine

<400> SEQUENCE: 61
tttgttcgtc tta                                                           13

<210> SEQ ID NO 62
<211> LENGTH: 13
<212> TYPE: DNA
<213> ORGANISM: Artificial Sequence
<220> FEATURE:
<223> OTHER INFORMATION: 208b_13_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
```

```
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 62
tttgttcgtc tta                                                        13

<210> SEQ ID NO 63
<211> LENGTH: 13
<212> TYPE: DNA
<213> ORGANISM: Artificial Sequence
<220> FEATURE:
<223> OTHER INFORMATION: 208b_13_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
```

-continued

```
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 63
tttgttcgtc tta                                                        13

<210> SEQ ID NO 64
<211> LENGTH: 13
<212> TYPE: DNA
<213> ORGANISM: Artificial Sequence
<220> FEATURE:
<223> OTHER INFORMATION: 208b_13_4 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
```

```
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid adenosine

<400> SEQUENCE: 64
tttgttcgtc tta                                                              13

<210> SEQ ID NO 65
<211> LENGTH: 11
<212> TYPE: DNA
<213> ORGANISM: Artificial Sequence
<220> FEATURE:
<223> OTHER INFORMATION: 208a like_11_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      cytidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
```

<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a deoxy adenosine

<400> SEQUENCE: 65
tgctcgtctt a                                                            11

<210> SEQ ID NO 66
<211> LENGTH: 11
<212> TYPE: DNA
<213> ORGANISM: Artificial Sequence
<220> FEATURE:
<223> OTHER INFORMATION: 208a like_11_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      cytidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 66
tgctcgtctt a                                                            11

<210> SEQ ID NO 67

```
<211> LENGTH: 11
<212> TYPE: DNA
<213> ORGANISM: Artificial Sequence
<220> FEATURE:
<223> OTHER INFORMATION: 208b_11_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a deoxy adenosine

<400> SEQUENCE: 67
tgttcgtctt a                                                              11

<210> SEQ ID NO 68
<211> LENGTH: 11
<212> TYPE: DNA
<213> ORGANISM: Artificial Sequence
<220> FEATURE:
<223> OTHER INFORMATION: 208b_11_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate guanosine
<220> FEATURE:
<221> NAME/KEY: MOD_RES
<222> LOCATION: (3)..(3)
<223> OTHER INFORMATION: May be a locked nucleic acid phosphorothioate
```

```
                thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      cytidine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid adenosine

<400> SEQUENCE: 68
tgttcgtctt a                                                              11

<210> SEQ ID NO 69
<211> LENGTH: 16
<212> TYPE: DNA
<213> ORGANISM: Artificial Sequence
<220> FEATURE:
<223> OTHER INFORMATION: 208b_16_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
```

```
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 69 cctttgttc gtctta                                                   16

<210> SEQ ID NO 70
<211> LENGTH: 16
<212> TYPE: DNA
<213> ORGANISM: Artificial Sequence
<220> FEATURE:
<223> OTHER INFORMATION: 208b_16_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
```

```
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 70 cctttgttc gtctta                                                   16

<210> SEQ ID NO 71
<211> LENGTH: 16
<212> TYPE: DNA
<213> ORGANISM: Artificial Sequence
<220> FEATURE:
<223> OTHER INFORMATION: 208b_16_3 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
```

```
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 71 cctttttgttc gtctta                                                      16

<210> SEQ ID NO 72
<211> LENGTH: 16
<212> TYPE: DNA
<213> ORGANISM: Artificial Sequence
<220> FEATURE:
<223> OTHER INFORMATION: 208b like_16_1 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
```

```
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 72 cctttttgctc gtctta                                                       16

<210> SEQ ID NO 73
<211> LENGTH: 16
<212> TYPE: DNA
<213> ORGANISM: Artificial Sequence
<220> FEATURE:
<223> OTHER INFORMATION: 208b like_16_2 oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
```

```
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate cytidine
<220> FEATURE:
<221> NAME/KEY: MOD_RES
<222> LOCATION: (14)..(14)
<223> OTHER INFORMATION: May be a locked nucleic acid phosphorothioate
      thymidine
<220> FEATURE:
<221> NAME/KEY: MOD_RES
<222> LOCATION: (15)..(15)
<223> OTHER INFORMATION: May be a locked nucleic acid phosphorothioate
      thymidine
<220> FEATURE:
<221> NAME/KEY: MOD_RES
<222> LOCATION: (16)..(16)
<223> OTHER INFORMATION: May be a deoxy adenosine

<400> SEQUENCE: 73 cctttttgctc gtctta                                                     16

<210> SEQ ID NO 74
<211> LENGTH: 16
<212> TYPE: DNA
<213> ORGANISM: Artificial Sequence
<220> FEATURE:
<223> OTHER INFORMATION: 208b like_16_3 oligonucleotide
<220> FEATURE:
<221> NAME/KEY: MOD_RES
```

```
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      cytidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a phosphorothioate thymidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 74 cctttgctc gtctta                                                      16

<210> SEQ ID NO 75
<211> LENGTH: 15
<212> TYPE: DNA
```

```
<213> ORGANISM: Artificial Sequence
<220> FEATURE:
<223> OTHER INFORMATION: 208b_15_5 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate adenosine
<220> FEATURE:
<221> NAME/KEY: MOD_RES
<222> LOCATION: (15)..(15)
<223> OTHER INFORMATION: May be a locked nucleic acid thymidine

<400> SEQUENCE: 75
ttttgttcgt cttat                                                  15

<210> SEQ ID NO 76
<211> LENGTH: 15
```

```
<212> TYPE: DNA
<213> ORGANISM: Artificial Sequence
<220> FEATURE:
<223> OTHER INFORMATION: 208b_15_6 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a locked nucleic acid thymidine

<400> SEQUENCE: 76
ttttgttcgt cttat                                                       15
```

```
<210> SEQ ID NO 77
<211> LENGTH: 15
<212> TYPE: DNA
<213> ORGANISM: Artificial Sequence
<220> FEATURE:
<223> OTHER INFORMATION: 208b_15_7 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate adenosine
<220> FEATURE:
<221> NAME/KEY: MOD_RES
<222> LOCATION: (15)..(15)
<223> OTHER INFORMATION: May be a locked nucleic acid thymidine

<400> SEQUENCE: 77
ttttgttcgt cttat                                                    15
```

```
<210> SEQ ID NO 78
<211> LENGTH: 15
<212> TYPE: DNA
<213> ORGANISM: Artificial Sequence
<220> FEATURE:
<223> OTHER INFORMATION: 208b_15_8 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a locked nucleic acid thymidine
```

-continued

```
<400> SEQUENCE: 78
ttttgttcgt cttat                                                          15

<210> SEQ ID NO 79
<211> LENGTH: 15
<212> TYPE: DNA
<213> ORGANISM: Artificial Sequence
<220> FEATURE:
<223> OTHER INFORMATION: 208b_15_9 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
```

<223> OTHER INFORMATION: May be a deoxy thymidine

<400> SEQUENCE: 79
ttttgttcgt cttat                                                    15

<210> SEQ ID NO 80
<211> LENGTH: 15
<212> TYPE: DNA
<213> ORGANISM: Artificial Sequence
<220> FEATURE:
<223> OTHER INFORMATION: 208b_15_10 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a phosphorothioate thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      adenosine

```
<220> FEATURE:
<221> NAME/KEY: MOD_RES
<222> LOCATION: (15)..(15)
<223> OTHER INFORMATION: May be a deoxy thymidine

<400> SEQUENCE: 80
ttttgttcgt cttat                                                          15

<210> SEQ ID NO 81
<211> LENGTH: 15
<212> TYPE: DNA
<213> ORGANISM: Artificial Sequence
<220> FEATURE:
<223> OTHER INFORMATION: 208b_15_11 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a phosphorothioate thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a locked nucleic acid phosphorothioate
      guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
```

```
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a deoxy thymidine

<400> SEQUENCE: 81
ttttgttcgt cttat                                                       15

<210> SEQ ID NO 82
<211> LENGTH: 15
<212> TYPE: DNA
<213> ORGANISM: Artificial Sequence
<220> FEATURE:
<223> OTHER INFORMATION: 208b_15_12 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
      cytidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
``` thymidine
<220> FEATURE:
<221> NAME/KEY: MOD_RES
<222> LOCATION: (14)..(14)
<223> OTHER INFORMATION: May be a phosphorothioate adenosine
<220> FEATURE:
<221> NAME/KEY: MOD_RES
<222> LOCATION: (15)..(15)
<223> OTHER INFORMATION: May be a locked nucleic acid thymidine

<400> SEQUENCE: 82
ttttgttcgt cttat                                                    15

<210> SEQ ID NO 83
<211> LENGTH: 15
<212> TYPE: DNA
<213> ORGANISM: Artificial Sequence
<220> FEATURE:
<223> OTHER INFORMATION: 208b_15_13 oligonucleotide
<220> FEATURE:
<221> NAME/KEY: MOD_RES
<222> LOCATION: (1)..(1)
<223> OTHER INFORMATION: May be a locked nucleic acid phosphorothioate
    thymidine
<220> FEATURE:
<221> NAME/KEY: MOD_RES
<222> LOCATION: (2)..(2)
<223> OTHER INFORMATION: May be a locked nucleic acid phosphorothioate
    thymidine
<220> FEATURE:
<221> NAME/KEY: MOD_RES
<222> LOCATION: (3)..(3)
<223> OTHER INFORMATION: May be a locked nucleic acid phosphorothioate
    thymidine
<220> FEATURE:
<221> NAME/KEY: MOD_RES
<222> LOCATION: (4)..(4)
<223> OTHER INFORMATION: May be a locked nucleic acid phosphorothioate
    thymidine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
    cytidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a phosphorothioate thymidine
<220> FEATURE:
<221> NAME/KEY: MOD_RES
<222> LOCATION: (11)..(11)
<223> OTHER INFORMATION: May be a locked nucleic acid phosphorothioate
    cytidine
<220> FEATURE:
<221> NAME/KEY: MOD_RES
<222> LOCATION: (12)..(12)
<223> OTHER INFORMATION: May be a locked nucleic acid phosphorothioate
    thymidine
<220> FEATURE:
<221> NAME/KEY: MOD_RES
<222> LOCATION: (13)..(13)

```
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a deoxy thymidine

<400> SEQUENCE: 83
ttttgttcgt cttat                                                     15

<210> SEQ ID NO 84
<211> LENGTH: 14
<212> TYPE: DNA
<213> ORGANISM: Artificial Sequence
<220> FEATURE:
<223> OTHER INFORMATION: 208b_14_7 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
```

```
<221> NAME/KEY: MOD_RES
<222> LOCATION: (13)..(13)
<223> OTHER INFORMATION: May be a phosphorothioate adenosine
<220> FEATURE:
<221> NAME/KEY: MOD_RES
<222> LOCATION: (14)..(14)
<223> OTHER INFORMATION: May be a locked nucleic acid thymidine

<400> SEQUENCE: 84
tttgttcgtc ttat                                                      14

<210> SEQ ID NO 85
<211> LENGTH: 14
<212> TYPE: DNA
<213> ORGANISM: Artificial Sequence
<220> FEATURE:
<223> OTHER INFORMATION: 208b_14_8 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
```

<220> FEATURE:
<221> NAME/KEY: MOD_RES
<222> LOCATION: (14)..(14)
<223> OTHER INFORMATION: May be a locked nucleic acid thymidine

<400> SEQUENCE: 85
tttgttcgtc ttat                                                             14

<210> SEQ ID NO 86
<211> LENGTH: 14
<212> TYPE: DNA
<213> ORGANISM: Artificial Sequence
<220> FEATURE:
<223> OTHER INFORMATION: 208b_14_9 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate adenosine
<220> FEATURE:
<221> NAME/KEY: MOD_RES
<222> LOCATION: (14)..(14)

<223> OTHER INFORMATION: May be a locked nucleic acid thymidine

<400> SEQUENCE: 86
tttgttcgtc ttat                                                    14

<210> SEQ ID NO 87
<211> LENGTH: 14
<212> TYPE: DNA
<213> ORGANISM: Artificial Sequence
<220> FEATURE:
<223> OTHER INFORMATION: 208b_14_10 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
<220> FEATURE:
<221> NAME/KEY: MOD_RES
<222> LOCATION: (14)..(14)
<223> OTHER INFORMATION: May be a locked nucleic acid thymidine

<400> SEQUENCE: 87
tttgttcgtc ttat                    14

<210> SEQ ID NO 88
<211> LENGTH: 14
<212> TYPE: DNA
<213> ORGANISM: Artificial Sequence
<220> FEATURE:
<223> OTHER INFORMATION: 208b_14_11 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
<220> FEATURE:
<221> NAME/KEY: MOD_RES
<222> LOCATION: (14)..(14)
<223> OTHER INFORMATION: May be a deoxy thymidine

<400> SEQUENCE: 88
tttgttcgtc ttat                    14

```
<210> SEQ ID NO 89
<211> LENGTH: 14
<212> TYPE: DNA
<213> ORGANISM: Artificial Sequence
<220> FEATURE:
<223> OTHER INFORMATION: 208b_14_12 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
<220> FEATURE:
<221> NAME/KEY: MOD_RES
<222> LOCATION: (14)..(14)
<223> OTHER INFORMATION: May be a deoxy thymidine

<400> SEQUENCE: 89
tttgttcgtc ttat                                                      14
```

```
<210> SEQ ID NO 90
<211> LENGTH: 14
<212> TYPE: DNA
<213> ORGANISM: Artificial Sequence
<220> FEATURE:
<223> OTHER INFORMATION: 208b_14_13 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a locked nucleic acid phosphorothioate
      guanosine
<220> FEATURE:
<221> NAME/KEY: MOD_RES
<222> LOCATION: (9)..(9)
<223> OTHER INFORMATION: May be a locked nucleic acid phosphorothioate
      thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
<220> FEATURE:
<221> NAME/KEY: MOD_RES
<222> LOCATION: (14)..(14)
<223> OTHER INFORMATION: May be a deoxy thymidine

<400> SEQUENCE: 90
tttgttcgtc ttat                                                        14

<210> SEQ ID NO 91
```

```
<211> LENGTH: 14
<212> TYPE: DNA
<213> ORGANISM: Artificial Sequence
<220> FEATURE:
<223> OTHER INFORMATION: 208b_14_14 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate adenosine
<220> FEATURE:
<221> NAME/KEY: MOD_RES
<222> LOCATION: (14)..(14)
<223> OTHER INFORMATION: May be a locked nucleic acid thymidine

<400> SEQUENCE: 91
tttgttcgtc ttat                                                    14

<210> SEQ ID NO 92
<211> LENGTH: 14
<212> TYPE: DNA
<213> ORGANISM: Artificial Sequence
<220> FEATURE:
```

<223> OTHER INFORMATION: 208b_14_15 oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a locked nucleic acid phosphorothioate
      thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate guanosine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a phosphorothioate thymidine
<220> FEATURE:
<221> NAME/KEY: MOD_RES
<222> LOCATION: (7)..(7)
<223> OTHER INFORMATION: May be a locked nucleic acid phosphorothioate
      cytidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      cytidine
<220> FEATURE:
<221> NAME/KEY: MOD_RES
<222> LOCATION: (11)..(11)
<223> OTHER INFORMATION: May be a locked nucleic acid phosphorothioate
      thymidine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a locked nucleic acid phosphorothioate
      adenosine
<220> FEATURE:
<221> NAME/KEY: MOD_RES
<222> LOCATION: (14)..(14)
<223> OTHER INFORMATION: May be a deoxy thymidine

<400> SEQUENCE: 92
tttgttcgtc ttat                                                    14

<210> SEQ ID NO 93
<211> LENGTH: 16
<212> TYPE: DNA
<213> ORGANISM: Artificial Sequence
<220> FEATURE:
<223> OTHER INFORMATION: 208b_16_4 oligonucleotide
<220> FEATURE:
<221> NAME/KEY: MOD_RES

```
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      guanosine
<220> FEATURE:
<221> NAME/KEY: MOD_RES
<222> LOCATION: (7)..(7)
<223> OTHER INFORMATION: May be a phosphorothioate thymidine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate cytidine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a phosphorothioate thymidine
<220> FEATURE:
<221> NAME/KEY: MOD_RES
<222> LOCATION: (12)..(12)
<223> OTHER INFORMATION: May be a phosphorothioate cytidine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate thymidine
<220> FEATURE:
<221> NAME/KEY: MOD_RES
<222> LOCATION: (15)..(15)
<223> OTHER INFORMATION: May be a locked nucleic acid phosphorothioate
      adenosine
<220> FEATURE:
<221> NAME/KEY: MOD_RES
<222> LOCATION: (16)..(16)
<223> OTHER INFORMATION: May be a deoxy thymidine

<400> SEQUENCE: 93
cttttgttcg tcttat                                                     16

<210> SEQ ID NO 94
<211> LENGTH: 16
```

```
<212> TYPE: DNA
<213> ORGANISM: Artificial Sequence
<220> FEATURE:
<223> OTHER INFORMATION: Trunc 16mer_UnivMM oligonucleotide
<220> FEATURE:
<221> NAME/KEY: MOD_RES
<222> LOCATION: (1)..(1)
<223> OTHER INFORMATION: May be a locked nucleic acid phosphorothioate
      thymidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a phosphorothioate cytidine
<220> FEATURE:
<221> NAME/KEY: MOD_RES
<222> LOCATION: (4)..(4)
<223> OTHER INFORMATION: May be a locked nucleic acid phosphorothioate
      thymidine
<220> FEATURE:
<221> NAME/KEY: MOD_RES
<222> LOCATION: (5)..(5)
<223> OTHER INFORMATION: May be a locked nucleic acid phosphorothioate
      adenosine
<220> FEATURE:
<221> NAME/KEY: MOD_RES
<222> LOCATION: (6)..(6)
<223> OTHER INFORMATION: May be a phosphorothioate guanosine
<220> FEATURE:
<221> NAME/KEY: MOD_RES
<222> LOCATION: (7)..(7)
<223> OTHER INFORMATION: May be a locked nucleic acid phosphorothioate
      adenosine
<220> FEATURE:
<221> NAME/KEY: MOD_RES
<222> LOCATION: (8)..(8)
<223> OTHER INFORMATION: May be a locked nucleic acid phosphorothioate
      adenosine
<220> FEATURE:
<221> NAME/KEY: MOD_RES
<222> LOCATION: (9)..(9)
<223> OTHER INFORMATION: May be a phosphorothioate adenosine
<220> FEATURE:
<221> NAME/KEY: MOD_RES
<222> LOCATION: (10)..(10)
<223> OTHER INFORMATION: May be a locked nucleic acid phosphorothioate
      guanosine
<220> FEATURE:
<221> NAME/KEY: MOD_RES
<222> LOCATION: (11)..(11)
<223> OTHER INFORMATION: May be a locked nucleic acid phosphorothioate
      adenosine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a phosphorothioate thymidine
<220> FEATURE:
<221> NAME/KEY: MOD_RES
<222> LOCATION: (14)..(14)
<223> OTHER INFORMATION: May be a locked nucleic acid phosphorothioate
      adenosine
<220> FEATURE:
<221> NAME/KEY: MOD_RES
<222> LOCATION: (15)..(15)
<223> OTHER INFORMATION: May be a phosphorothioate guanosine
<220> FEATURE:
<221> NAME/KEY: MOD_RES
<222> LOCATION: (16)..(16)
<223> OTHER INFORMATION: May be a locked nucleic acid adenosine

<400> SEQUENCE: 94
```
tcctagaaag agtaga    16

<210> SEQ ID NO 95
<211> LENGTH: 15
<212> TYPE: DNA
<213> ORGANISM: Artificial Sequence
<220> FEATURE:
<223> OTHER INFORMATION: Trunc 15mer_Univ oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate adenosine
<220> FEATURE:
<221> NAME/KEY: MOD_RES
<222> LOCATION: (5)..(5)
<223> OTHER INFORMATION: May be a phosphorothioate guanosine
<220> FEATURE:
<221> NAME/KEY: MOD_RES
<222> LOCATION: (6)..(6)
<223> OTHER INFORMATION: May be a locked nucleic acid phosphorothioate
      adenosine
<220> FEATURE:
<221> NAME/KEY: MOD_RES
<222> LOCATION: (7)..(7)
<223> OTHER INFORMATION: May be a locked nucleic acid phosphorothioate
      adenosine
<220> FEATURE:
<221> NAME/KEY: MOD_RES
<222> LOCATION: (8)..(8)
<223> OTHER INFORMATION: May be a phosphorothioate adenosine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate adenosine
<220> FEATURE:
<221> NAME/KEY: MOD_RES
<222> LOCATION: (14)..(14)
<223> OTHER INFORMATION: May be a locked nucleic acid phosphorothioate
      guanosine
<220> FEATURE:
<221> NAME/KEY: MOD_RES
<222> LOCATION: (15)..(15)
<223> OTHER INFORMATION: May be a locked nucleic acid adenosine

<400> SEQUENCE: 95
cctagaaaga gtaga                                                       15

<210> SEQ ID NO 96
<211> LENGTH: 16
<212> TYPE: DNA
<213> ORGANISM: Artificial Sequence
<220> FEATURE:
<223> OTHER INFORMATION: UnivCont2_16mer oligonucleotide
<220> FEATURE:
<221> NAME/KEY: MOD_RES
<222> LOCATION: (1)..(1)
<223> OTHER INFORMATION: May be a locked nucleic acid phosphorothioate
      adenosine
<220> FEATURE:
<221> NAME/KEY: MOD_RES
<222> LOCATION: (2)..(2)
<223> OTHER INFORMATION: May be a phosphorothioate cytidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a locked nucleic acid phosphorothioate
      thymidine
<220> FEATURE:
<221> NAME/KEY: MOD_RES
<222> LOCATION: (6)..(6)
<223> OTHER INFORMATION: May be a locked nucleic acid phosphorothioate
      thymidine
<220> FEATURE:
<221> NAME/KEY: MOD_RES
<222> LOCATION: (7)..(7)
<223> OTHER INFORMATION: May be a phosphorothioate guanosine
<220> FEATURE:
<221> NAME/KEY: MOD_RES
<222> LOCATION: (8)..(8)
<223> OTHER INFORMATION: May be a locked nucleic acid phosphorothioate
      thymidine
<220> FEATURE:
<221> NAME/KEY: MOD_RES
<222> LOCATION: (9)..(9)
<223> OTHER INFORMATION: May be a phosphorothioate guanosine
<220> FEATURE:
<221> NAME/KEY: MOD_RES
<222> LOCATION: (10)..(10)
<223> OTHER INFORMATION: May be a locked nucleic acid phosphorothioate
      thymidine
<220> FEATURE:
<221> NAME/KEY: MOD_RES
<222> LOCATION: (11)..(11)
<223> OTHER INFORMATION: May be a locked nucleic acid phosphorothioate
      adenosine
<220> FEATURE:
<221> NAME/KEY: MOD_RES
<222> LOCATION: (12)..(12)
<223> OTHER INFORMATION: May be a phosphorothioate guanosine
<220> FEATURE:
<221> NAME/KEY: MOD_RES
<222> LOCATION: (13)..(13)
<223> OTHER INFORMATION: May be a locked nucleic acid phosphorothioate
      thymidine
<220> FEATURE:
<221> NAME/KEY: MOD_RES
<222> LOCATION: (14)..(14)
<223> OTHER INFORMATION: May be a phosphorothioate adenosine
<220> FEATURE:
<221> NAME/KEY: MOD_RES
<222> LOCATION: (15)..(15)
<223> OTHER INFORMATION: May be a phosphorothioate cytidine
<220> FEATURE:
<221> NAME/KEY: MOD_RES
<222> LOCATION: (16)..(16)
<223> OTHER INFORMATION: May be a locked nucleic acid adenosine

<400> SEQUENCE: 96
acttttgtgt agtaca                                                 16

<210> SEQ ID NO 97
<211> LENGTH: 15
<212> TYPE: DNA
<213> ORGANISM: Artificial Sequence
<220> FEATURE:
<223> OTHER INFORMATION: UnivCont2_15mer oligonucleotide
<220> FEATURE:
<221> NAME/KEY: MOD_RES
<222> LOCATION: (1)..(1)
<223> OTHER INFORMATION: May be a locked nucleic acid phosphorothioate
      cytidine
<220> FEATURE:
<221> NAME/KEY: MOD_RES
<222> LOCATION: (2)..(2)
<223> OTHER INFORMATION: May be a phosphorothioate thymidine
<220> FEATURE:
<221> NAME/KEY: MOD_RES
<222> LOCATION: (3)..(3)
<223> OTHER INFORMATION: May be a locked nucleic acid phosphorothioate
      thymidine
<220> FEATURE:
<221> NAME/KEY: MOD_RES
<222> LOCATION: (4)..(4)
<223> OTHER INFORMATION: May be a phosphorothioate thymidine
<220> FEATURE:
<221> NAME/KEY: MOD_RES
<222> LOCATION: (5)..(5)
<223> OTHER INFORMATION: May be a phosphorothioate thymidine
<220> FEATURE:
<221> NAME/KEY: MOD_RES
<222> LOCATION: (6)..(6)
<223> OTHER INFORMATION: May be a locked nucleic acid phosphorothioate
      guanosine
<220> FEATURE:
<221> NAME/KEY: MOD_RES
<222> LOCATION: (7)..(7)
<223> OTHER INFORMATION: May be a locked nucleic acid phosphorothioate
      thymidine
<220> FEATURE:
<221> NAME/KEY: MOD_RES
<222> LOCATION: (8)..(8)
<223> OTHER INFORMATION: May be a phosphorothioate guanosine
<220> FEATURE:
<221> NAME/KEY: MOD_RES
<222> LOCATION: (9)..(9)
<223> OTHER INFORMATION: May be a phosphorothioate thymidine
<220> FEATURE:
<221> NAME/KEY: MOD_RES
<222> LOCATION: (10)..(10)
<223> OTHER INFORMATION: May be a locked nucleic acid phosphorothioate
      adenosine
<220> FEATURE:
<221> NAME/KEY: MOD_RES
<222> LOCATION: (11)..(11)
<223> OTHER INFORMATION: May be a phosphorothioate guanosine
<220> FEATURE:
<221> NAME/KEY: MOD_RES
<222> LOCATION: (12)..(12)
<223> OTHER INFORMATION: May be a locked nucleic acid phosphorothioate
      thymidine
<220> FEATURE:
<221> NAME/KEY: MOD_RES
<222> LOCATION: (13)..(13)
<223> OTHER INFORMATION: May be a phosphorothioate adenosine
<220> FEATURE:
<221> NAME/KEY: MOD_RES
<222> LOCATION: (14)..(14)
<223> OTHER INFORMATION: May be a locked nucleic acid phosphorothioate
      cytidine
<220> FEATURE:
<221> NAME/KEY: MOD_RES

```
<222> LOCATION: (15)..(15)
<223> OTHER INFORMATION: May be a locked nucleic acid adenosine

<400> SEQUENCE: 97
cttttgtgta gtaca                                                    15

<210> SEQ ID NO 98
<211> LENGTH: 16
<212> TYPE: RNA
<213> ORGANISM: Unknown
<220> FEATURE:
<223> OTHER INFORMATION: miR-208a antisense oligonucleotide

<400> SEQUENCE: 98
uaagacgagc aaaaag                                                   16

<210> SEQ ID NO 99
<211> LENGTH: 16
<212> TYPE: RNA
<213> ORGANISM: Unknown
<220> FEATURE:
<223> OTHER INFORMATION: miR-208b antisense oligonucleotide

<400> SEQUENCE: 99
uaagacgaac aaaaag                                                   16
```

CONTROL OF WHOLE BODY ENERGY HOMEOSTASIS BY MICRORNA REGULATION

RELATED APPLICATIONS

This application is a national phase of International Application No. PCT/US2012/059349, which claims the benefit of U.S. Provisional Application Nos. 61/544,187, filed Oct. 6, 2011, and 61/638,345, filed Apr. 25, 2012, each of which are each is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_031_02US_SeqList_ST25.txt, date recorded: Apr. 4, 2014, file size 138 kilobytes).

FIELD OF THE INVENTION

The present invention relates to the treatment and prevention of metabolic disorders by administering agents that modulate the activity or expression of a microRNA (miRNA). In particular, the invention provides a method for treating or preventing metabolic disorders by inhibiting the expression or activity of miR-208a and/or miR-208b in cells of a subject. In addition, the invention provides a method for regulating fatty acid metabolism in a cell by contacting the cell with a modulator of miR-208a and/or miR-208b expression or activity. The present invention also provides a method for enhancing or elevating mitochondrial function, improving fuel metabolism, and/or maintenance of redox-homeostasis by inhibiting the expression or activity of miR-208a and/or miR-208b in cells of a subject.

BACKGROUND

Maintaining energy homeostasis requires a balance between energy consumption and energy expenditure. In Western societies, excess food consumption has led to a shift in energy balance resulting in a dramatic increase in obesity (Van et al., (2006) Nature 444, 875-880), a multi-organ disorder that enhances the risk of type 2 diabetes (T2D), hypertension, hyperlipidemia and cardiovascular disease (Mathieu et al., (2008) The International Journal of Biochemistry & Cell Biology 40, 821-836). Impaired metabolism of energy-providing substrates and myocardial lipid accumulation are early abnormalities found in obese and insulin-resistant individuals (Harmancey et al., (2008) Hypertension 5, 181-187). Mitochondrial dysfunction in metabolically active tissues (e.g. adipose, liver and skeletal muscle) is commonly associated with metabolic diseases including metabolic syndrome (MS), insulin resistance (IR) and T2D (Muoio and Newgard, (2008) Nat Rev Mol Cell Biol, 2008. 9, 193-205).

Accordingly, there is a growing need to identify effective therapies to treat and prevent obesity and related metabolic diseases, such as by enhancing mitochondrial function.

SUMMARY OF THE INVENTION

The present invention is based, in part, on the surprising discovery that miR-208 inhibition reduces age-induced weight gain and high fat-induced weight gain and improves glucose tolerance, fuel metabolism, mitochondrial function, and redox-homeostasis. Accordingly, the present invention provides methods of treating or preventing metabolic disorders, such as obesity and diabetes, and/or by modulating the expression or activity of miR-208a and/or miR-208b in cells (e.g. cardiac and/or skeletal muscle cells) in a subject in need thereof. The present invention also provides methods of enhancing mitochondrial function, redox-homeostasis, and fuel metabolism by modulating the expression or activity of miR-208a and/or miR-208b in cells in a subject in need thereof.

In one embodiment, the method of the present invention comprises administering to the subject an inhibitor of miR-208a and/or miR-208b (e.g. an antisense oligonucleotide inhibitor), wherein the expression or activity of miR-208a and/or miR-208b is reduced in the cells of the subject following administration. Administration of the inhibitor may be for treating or preventing a metabolic disorder in a subject in need thereof. In one embodiment, administration of the inhibitor is for enhancing mitochondrial function in a subject in need thereof.

The metabolic disorder to be treated can include metabolic syndrome, obesity, diabetes mellitus, diabetic nephropathy, insulin resistance, atherosclerosis, a lipid storage disorder, a glycogen storage disease, medium-chain acyl-coenzyme A dehydrogenase deficiency, lipid oxidation, high cholesterol, or aberrant glucose uptake and/or utilization. Secondary diseases or conditions resulting from these metabolic disorders can also be prevented or treated with the methods of the invention. For example, in one embodiment, the invention provides a method of preventing or treating secondary diseases or disorders resulting from obesity, such as sleep apnea, cancer, stroke, and osteoarthritis, by administering an inhibitor of miR-208a and/or miR-208b. Disorders due to mitochondrial dysfunction can also be treated by the methods disclosed herein. For example, the subject can suffer from, or be at risk for muscle weakness, frailty, sarcopenia, muscular dystrophy, muscle atrophy, amyotrophic lateral sclerosis, or a mitochondrial myopathy.

The miR-208a and miR-208b inhibitors suitable for use in the methods of the present invention can be antisense oligonucleotides. In one embodiment, the antisense oligonucleotide comprises a sequence that is at least partially complementary to a mature sequence of miR-208a and/or miR-208b. In certain embodiments, the antisense oligonucleotides comprise one or more sugar or backbone modifications, such as locked nucleic acids, bicyclic nucleosides, phosphonoformates, 2' O-alkyl modifications, and phosphorothioate linkages. In one embodiment, the antisense oligonucleotides comprise a 2' O-alkyl modification or a 2'-halo modification, such as a 2'-fluoro modification. In other embodiments, the miR-208a and/or miR-208b inhibitor is an antisense oligonucleotide of about 6 to about 22 nucleotides in length.

In another embodiment, the present invention provides a method of regulating fatty acid metabolism in a cell comprising contacting the cell with a modulator of miR-208a and/or miR-208b expression or activity. The modulator can be an inhibitor or agonist of miR-208a and/or miR-208b expression or activity. In certain embodiments, fatty acid metabolism is increased in the cell following contact with a miR-208a and/or miR-208b inhibitor as compared to a cell not exposed to the inhibitor. In other embodiments, fatty acid metabolism is decreased in the cell following contact with a miR-208a and/or miR-208b agonist as compared to a cell not exposed to the agonist. The cell may be in vitro or in vivo. In some embodiments, the cell is a cardiomyocyte, a skeletal muscle cell, a preadipocyte, an adipocyte, a hepatocyte, or a pancreatic cell.

The present invention encompasses the use of chemically modified antisense oligonucleotides capable of inhibiting the expression (e.g., abundance) of miR-208 family miR-NAs, including miR-208a and miR-208b, to affect energy homeostasis. The invention further provides pharmaceutical compositions comprising the antisense oligonucleotides, and methods of treating patients having conditions or disorders related to or affecting energy homeostasis such as metabolic disorders.

In another aspect, the invention provides pharmaceutical compositions and formulations comprising the antisense oligonucleotide inhibitors described herein for use in the methods of the invention. Such formulations and compositions may involve incorporation of the antisense oligonucleotide within a variety of macromolecular assemblies, micelle, or liposome compositions for cellular delivery. In certain embodiments, the compositions are suitable or formulated for intradermal, subcutaneous, intramuscular, intraperitoneal or intravenous injection, or by direct injection into target tissue (e.g., cardiac or skeletal muscle tissue).

Other aspects and embodiments of the invention will be apparent from the following detailed description of the invention.

BRIEF DESCRIPTION OF DRAWINGS

FIG. 4. AntimiR-208a (M-10101) treated mice are resistant to diet-induced obesity. A. Representative images comparing control (M-10591) and antimiR-208a (M-10101) treated mice on a normal diet (NC) and 6 weeks after a high-fat diet (HF). B. Growth curves and percent increase in body weight comparing control (M-10591) and antimiR-208a (M-10101) treated mice on a normal diet (NC) and 6 weeks after a high-fat diet (HF). C. Body composition measured by NMR comparing control (M-10591) and antimiR-208a (M-10101) treated mice on a normal diet (NC) and 6 weeks after a high-fat diet (HF). The white sections of each bar represent the fat weight. D. Weight of visceral white adipose tissue (WAT) and subscapular brown adipose tissue (BAT) from control (M-10591) and antimiR-208a (M-10101) treated mice on a normal diet (NC) and 6 weeks after a high-fat diet (HF). E. H&E stain of visceral WAT and subscapular BAT from control and antimiR-208-treated mice on normal diet or high-fat diet. Scale bar=40 µm. F. Pictures of visceral WAT and liver from antimiR-208a and control antimiR treated mice on high-fat diet for 6 weeks. G. Cell size of visceral WAT (n=5). Images from 3 sections 200 mm apart were analyzed from 7-8 mice in each group representing>500 cells. Serum triglyceride levels (H) and serum cholesterol levels (I) from control (M-10591) and antimiR-208a (M-10101) treated mice on a normal diet (NC) and 6 weeks after a high-fat diet (HF).

FIG. 5. AntimiR-208a (M-10101) treated mice are resistant to glucose intolerance. Glucose tolerance test (A) and area under the curve for the glucose tolerance test (B) from control antimiR (M-10591) and antimiR-208a (M-10101) treated mice on a normal diet (NC) and 6 weeks after a high-fat diet (HF). Fasting insulin (C) and leptin (D) levels from control antimiR and antimiR-208a treated mice on a normal diet (NC) and 6 weeks after a high-fat diet (HF).

FIG. 6. Growth curves (A) and percent increase in body weight (B) comparing saline, control antimiR (M-10591, M-10649, M-10702, M-11182), and antimiR-208a (M-10101, M-10673, M-10681, M-10683) treated mice on a normal diet (REG) and 12 weeks after a high-fat diet (HFD).

DETAILED DESCRIPTION OF THE INVENTION

Figure 1:
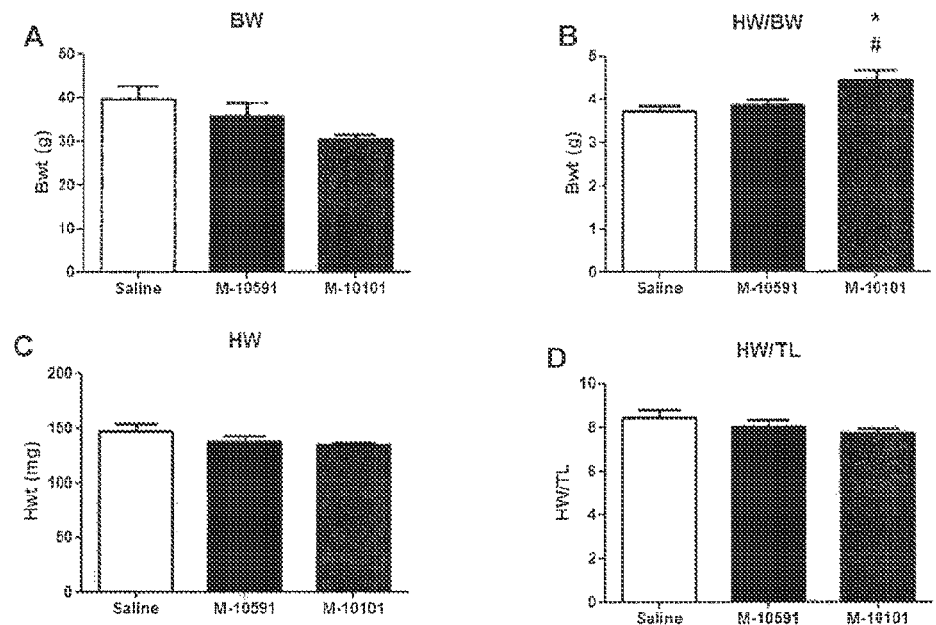
FIG. 1. AntimiR-208a (M-10101) reduces age-induced weight gain in mice. Mice treated with 3×25 mg/kg of antimiR-208a (M-10101) at day 1, 2 and 3 and a maintenance dose of 25 mg/kg every 2 weeks show a reduction in body weight (BW) increase with age, compared to either control (M-10591) or saline injected animals (A). While all groups started at a comparable weight at 8 weeks of age, saline and control injected animals show a significantly lower heart weight to body weight (HW/BW) ratio due to a decrease in age-induced body weight (B). Also shown are the heart weights (HW) and heart weights to total weights (HW/TL) of the different groups in panels C and D, respectively.

The present invention provides a method of treating or preventing a metabolic disorder in a subject in need thereof. Also provided herein is a method of enhancing mitochondrial function, redox-homeostasis, and/or fuel metabolism. MiRNAs represent novel therapeutic targets for the development of treatments for such diseases, including, obesity, diabetes, and other metabolic disorders.

In one embodiment, the method comprises administering to the subject an inhibitor of miR-208a and/or miR-208b as described herein, wherein the expression or activity of miR-208a and/or miR-208b is reduced in the cells of the subject following administration. As used herein, the term "patient" or "subject" refers to any vertebrate including, without limitation, humans and other primates (e.g., chimpanzees and other apes and monkey species), domestic mammals (e.g., dogs and cats), farm animals (e.g., cattle, sheep, pigs, goats and horses), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In certain embodiments, the subject is a human.

In certain embodiments, the subject in need thereof has been diagnosed with, is suffering from, and/or has exhibited symptoms of a metabolic condition or disorder. In other embodiments, the subject has not been diagnosed with, is not suffering from, and/or has not exhibited symptoms of a metabolic condition or disorder. The metabolic disorders include, but are not limited to, metabolic syndrome, obesity, diabetes mellitus, diabetic nephropathy, resistance, atherosclerosis, dyslipidemia (such as mixed or diabetic dyslipidemia), hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, claudication, stroke and others, kidney diseases, ketoacidosis, nephropathy, diabetic neuropathy, diabetic retinopathy, nonalcoholic fatty liver diseases such as steatosis or nonalcoholic steatohepatitis (NASH), a lipid storage disorder (e.g., Niemann-Pick disease, Gaucher's disease, Farber disease, Fabry disease, Wolman disease, and cholesteryl ester storage disease), polycystic ovarian syndrome (PCOS), high cholesterol, or aberrant glucose uptake and/or utilization. In certain embodiments, the metabolic disorder to be treated with the methods of the invention is obesity, hypercholesterolemia, type 2 diabetes, hepatic steatosis or hyperlipidemia.

In other embodiments, the subject has not been diagnosed with, is not suffering from, and/or has not exhibited symptoms of a cardiovascular disease or disorder, such as atherosclerosis and its sequelae including angina, heart attack, heart failure, coronary artery disease, myocardial infarction, congestive heart failure, and for cardiac hypertrophy. In some embodiments, the subject has not been diagnosed with, is not suffering from, and/or has not exhibited symptoms of a cardiovascular disease or disorder, and has been diagnosed with, is suffering from, and/or has exhibited symptoms of a metabolic condition or disorder.

In certain embodiments, the subject in need thereof has been diagnosed with, is suffering from, and/or has exhibited symptoms of a condition or disorder related to mitochondrial dysfunction. In other embodiments, the subject has not been diagnosed with, is not suffering from, and/or has not exhibited symptoms of a condition or disorder related to mitochondrial dysfunction. The disorder or condition can include, but are not limited to, muscle weakness, frailty, sarcopenia, muscular dystrophy, muscle atrophy, amyotrophic lateral sclerosis, or a mitochondrial, myopathy. In certain embodiments, the subject in need thereof has been diagnosed with, is suffering from, and/or has exhibited symptoms of a condition or disorder related to mitochondrial dysfunction, and has not been diagnosed with, is not suffering from, and/or has not exhibited symptoms of a cardiovascular disease or disorder In some embodiments, the metabolic disorder is a glycogen storage disease (GSD). For instance, the methods of the invention provide treating or preventing any of the types of GSD (e.g., GSD type 0 and GSD type I to GSD type XIII) in a subject in need thereof by administering to the subject a miR-208a and/or miR-208b inhibitor. GSDs include, but are not limited to, von Gierke's disease, Pompe's disease, Cori's disease or Forbes' disease, Andersen disease, McArdle disease, Hers' disease, Tarui's disease, Fanconi-Bickel syndrome, and red cell aldolase deficiency. In another embodiment, the metabolic disorder is medium-chain acylcoenzyme A dehydrogenase (MCAD) deficiency. Individuals having MCAD deficiency exhibit an impairment in fatty acid oxidation that can be fatal. In one embodiment of the invention, fatty acid metabolism is increased in subjects having MCAD deficiency following administration of a miR-208a and/or miR-208b inhibitor.

The inventors have surprisingly found that inhibition of miR-208a activity results in enhanced mitochondrial function in liver, skeletal muscle, and cardiac tissue. Accordingly, the present invention also provides a method of enhancing mitochondrial function or redox-homeostasis in a subject in need thereof. In one embodiment, the method comprises administering to the subject an antisense oligonucleotide comprising a sequence that is at least partially complementary to a miR-208a or miR-208b sequence, wherein the expression or activity of miR-208a or miR-208b is reduced in the cells of the subject following administration of the antisense oligonucleotide. In certain embodiments, the subject in need of enhanced mitochondrial function or redox-homeostasis is diagnosed with, suffers from, or is at risk for muscle weakness, frailty, sarcopenia, muscular dystrophy, muscle atrophy, amyotrophic lateral sclerosis, or a mitochondrial myopathy. Mitochondrial myopathies include, but are not limited to, mitochondrial encephalomyopathy, lactic acidosis, and stroke-like syndrome (MELAS), myoclonic epilepsy and ragged-red fibers (MERRF), Kearns-Sayre syndrome (KSS), or chronic progressive external ophthalmoplegia (CPEO).

In related embodiments, the present invention provides a method of treating muscle atrophy or sarcopenia in a subject in need thereof. Sarcopenia describes the slow but progressive loss of muscle mass with advancing age and is characterized by a deterioration of muscle quantity and quality leading to a gradual slowing of movement and a decline in strength (Ryall et al., Biogerontology (2008) 9:213-228). Sarcopenia is a component of frailty syndrome frequently observed in elderly populations. In one embodiment, the method of treating muscle atrophy or sarcopenia in a subject in need thereof comprises administering to the subject an antisense oligonucleotide comprising a sequence that is at least partially complementary to a miR-208a or miR-208b sequence, wherein the expression or activity of miR-208a or miR-208b is reduced in the cells of the subject following administration of the antisense oligonucleotide. In some embodiments, the method further comprises administering the anti-miR-208a/anti-miR-208b oligonucleotide in combination with one or more additional therapies to counteract muscle atrophy. Such suitable additional therapies include, but are not limited to, selective androgen receptor modulators (e.g., ostarine, BMS-564,929, and LGD-4033), anabolic steroids, human growth hormone, and dehydroepiandrosterone (DHEA). In certain embodiments, a subject in need of treatment for muscle atrophy or sarcopenia is an elderly patient, preferably an elderly human patient.

The present invention also includes a method of preventing or treating secondary diseases or conditions resulting from metabolic disorders or mitochondrial dysfunction by administering to a subject in need thereof an inhibitor of miR-208a and/or miR-208b as described herein. For example, in one embodiment, the invention provides a method of preventing or treating sleep apnea comprising administering to a subject in need thereof an inhibitor of miR-208a and/or miR-208b. In another embodiment, the invention provides a method of preventing or treating cancer by administering to a subject in need thereof an inhibitor of miR-208a and/or miR-208b. In still another embodiment, the invention provides a method of preventing or treating osteoarthritis by administering to a subject in need thereof an inhibitor of miR-208a and/or miR-208b. In one embodiment, the invention provides a method of preventing or treating a stroke by administering to a subject in need thereof an inhibitor of miR-208a and/or miR-208b.

In some embodiments, the methods of the present invention are used preventatively prior to the development of any metabolic disorder or secondary disease or condition resulting from a metabolic disorder or mitochondrial dysfunction. In these embodiments, subjects in need of preventative treatment may be identified on the basis of such factors as a family history of a metabolic disorder or secondary disease or condition.

In certain embodiments, the methods of treating or preventing a metabolic disorder in a subject in need thereof further comprises administering one or more conventional therapies for treating metabolic disorders. Thus, included within the scope of the present invention are embodiments comprising co-administration of, and compositions and medicaments which contain, in addition to an antisense oligonucleotide used in the present invention or a pharmaceutical composition or formulation containing such an antisense oligonucleotide, other therapeutic agents and/or active ingredients. Such multiple drug regimens, often referred to as combination therapies, may be used in the treatment and/or prevention of metabolic disorders.

Examples of conventional therapies that may be administered in combination with one or more antisense oligonucleotides described herein or a pharmaceutical composition or formulation containing such antisense oligonucleotides, and either administered separately or in the same pharmaceutical composition, include but are not limited to:

(a) PPARγ agonists and partial agonists, including both glitazones and non-glitazones (e.g. troglitazone, pioglitazone, englitazone, MCC-555, rosiglitazone, balaglitazone, netoglitazone, T-131, LY-30051.2 and LY-818;
(b) Biguanides such as metformin and phenformin;
(c) Protein tyrosine phosphatase-1B (PIP-1B) inhibitors,
(d) Dipeptidyl peptidase IV (DP-IV) inhibitor, such as MK-0431 and LAF-237;
(e) Insulin or insulin mimetics;
(f) Sulfonylureas such as tolbutamide and glipizide or related materials;
(g) α-glucosidase inhibitors (such as acarbose);
(h) agents which improve a patient's lipid profile such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors such as for example ezetimibe, (vi) acyl CoA:cholesterol acyltransferase (ACAT) inhibitors such as avasimibe, (vii) CETP inhibitors such as torcetrapib and (viii) phenolic anti-oxidants such as probucol;
(i) PPARα/γ dual agonists such as muraglitazar, tesaglitazar, farglitazar and JT-501;
(j) PPARδ agonists such those disclosed in WO97/28149;
(k) Antiobesity compounds such as fenfluramine, dextenfluramine, phentiramine, subitramine, orlistat, neuropeptide Y5 inhibitors, MC4R agonists, cannabinoid receptor 1 antagonists/inverse agonists and β3 adrenergic receptor agonists;
(l) Ileal bile acid transporter inhibitors;
(m) Agents intended for use in inflammatory conditions such as aspirin, non-steroidal, anti-inflammatory drugs, glucocorticoids, azulfidine and cyclo-oxygenase 2 selective inhibitors;
(n) Glucagon receptor antagonists;
(o) GLP-1 or GLP-1 analogs, such as exendins, for example exenitide;
(p) GIP-1; and
(q) Hydroxysterol dehydrogenase-1 (HSD-1) inhibitors.

One or more of any of the above conventional therapies can be co-administered with one or more antisense oligonucleotides described herein or a pharmaceutical composition or formulation containing such antisense oligonucleotides to treat or prevent a metabolic disorder in a subject in need thereof. Non-limiting examples of combination therapies include combinations of an antisense oligonucleotide targeting miR-208a and/or miR-208b with one or more conventional therapies selected from biguanides, sulfonylureas, HMG-CoA reductase inhibitors, other PPAR agonists, PIP-1B inhibitors, DP-IV inhibitors and anti-obesity compounds.

The antisense oligonucleotides described herein or a pharmaceutical composition or formulation containing such antisense oligonucleotides, and conventional therapies may be administered in the same dosage forms or in separate dosage forms. When administered in separate dosage forms, the antisense oligonucleotides may be administered simultaneously or serially (i.e. separated by some interval) with the conventional therapy. Thus, the administration of the antisense oligonucleotide may be prior to, concurrent with, or subsequent to the administration of the conventional therapy.

The inventors have found that the effects of miR-208 inhibition on metabolism are mediated in part through de-repression of its target MED13 (a.k.a THRAP1), such as in cardiac tissue. Cardiac-specific over-expression of MED13 in mice confers resistance to high fat diet-induced obesity and improves systemic insulin sensitivity and glucose tolerance, whereas genetic deletion of MED13, such as in cardiomyocytes, enhances Obesity in response to high fat diet and exacerbates metabolic syndrome (data not shown). Thus, the present invention also encompasses a method of treating or preventing a metabolic disorder in a subject in need thereof comprising enhancing MED13 expression, such as in cardiac cells. For example, provided herein is a method of administering a MED13 agonist, such as an expression vector encoding MED13. The polynucleotide encoding MED13 can be under the control of a cardiac-specific promoter, such as alpha-myosin heavy chain.

In another embodiment, the present invention encompasses a method of increasing glucose uptake and/or utilization in a subject in need thereof comprising administering to the subject an inhibitor of miR-208a and/or miR-208b activity or expression as described herein. In some embodiments, the subject is diagnosed with insulin resistance or diabetes mellitus. In one embodiment, the subject's blood glucose level is reduced following administration of the miR-208a and/or miR-208b inhibitor as compared to the blood glucose level of the subject prior to administration of the inhibitor. In another embodiment, the subject's blood glucose level is reduced to within normal levels as measured by the oral glucose tolerance test following administration of the miR-208a and/or miR-208b inhibitor. For instance, in certain embodiments, the subject's fasting blood glucose level is less than about 110 mg/dl. In other embodiments, the subject's blood glucose level 2 hours post glucose ingestion is less than about 140 mg/dl.

In another embodiment, the present invention encompasses a method of decreasing cholesterol in a subject in need thereof comprising administering to the subject an inhibitor of miR-208a and/or miR-208b activity or expression as described herein. In some embodiments, the subject is diagnosed with a disease associated with high cholesterol such as coronary heart disease, stroke, peripheral vascular disease, type 2 diabetes, and high blood pressure. In one embodiment, the subject's total cholesterol level is decreased and/or HDL cholesterol level is increased following administration of the miR-208a and/or miR-208b inhibitor as compared to the total cholesterol and HDL cholesterol levels of the subject prior to administration of the inhibitor. In another embodiment, the subject's cholesterol levels are restored to within normal levels as measured by a lipoprotein profile blood test following administration of the miR-208a and/or miR-208b inhibitor. For instance, in certain embodiments, the subject's total cholesterol level is reduced to less than about 200 mg/dL. In other embodiments, the subject's HDL cholesterol level is increased to greater than or equal to about 40 mg/dL.

In another embodiment, the present invention encompasses a method of treating obesity in a subject in need thereof comprising administering to the subject an inhibitor of miR-208a and/or miR-208b activity or expression as described herein. In some embodiments, the subject is diagnosed with obesity. In certain embodiments, the subject in need of treatment has a body mass index of 25 or greater. In other embodiments, the subject in need of treatment has a body mass index of 30 or greater. In one embodiment, the subject's body mass index and/or waist circumference is reduced following administration of the miR-208a and/or miR-208b inhibitor as compared to the body mass index and/or waist circumference of the subject prior to administration of the inhibitor. In another embodiment, the subject's body mass index and/or waist circumference is reduced to within normal levels adjusted for the sex and age of the subject following administration of the miR-208a and/or miR-208b inhibitor.

The present invention also provides a method of regulating fatty acid metabolism in a cell. Also provided herein is a method of regulating glucose metabolism, such as by regulating glycogen synthesis. A method of enhancing mitochondrial function and improving redox-homeostasis by administering a modulator of miR-208a and/or miR-208b expression or activity, such as an inhibitor of miR-208a and/or miR-208b expression or activity, is also provided.

In one embodiment, the methods disclosed herein comprise contacting a cell with a modulator of miR-208a and/or miR-208b expression or activity. As used herein, a "modulator" is a molecule that regulates the expression or activity of miR-208a and/or miR-208b. Modulators can be agonists of miR-208a and/or miR-208b function (i.e. enhance the activity or expression of miR-208a or miR-208b) or they can be inhibitors of miR-208a and/or miR-208b function (i.e. reduce the activity or expression of miR-208a or miR-208b). Modulators can include proteins, peptides, polypeptides, polynucleotides, antisense oligonucleotides, or small molecules. Modulators of miR-208a and/or miR-208b expression or activity include miR-208a and/or miR-208b inhibitors and agonists as described herein.

In certain embodiments, the modulator is an inhibitor of miR-208a and/or miR-208b expression or activity, and fatty acid metabolism is increased in the cell following contact with the miR-208a and/or miR-208b inhibitor as compared to a cell not exposed to the inhibitor. In other embodiments, the modulator is an agonist of miR-208a and/or miR-208b expression or activity, and fatty acid metabolism is decreased in the cell following contact with the miR-208a and/or miR-208b agonist as compared to a cell not exposed to the agonist.

In certain embodiments, the modulator is an inhibitor of miR-208a and/or miR-208b expression or activity, and glucose metabolism is increased in the cell following contact with the miR-208a and/or miR-208b inhibitor as compared to a cell not exposed to the inhibitor. In other embodiments, the modulator is an agonist of miR-208a and/or miR-208b expression or activity, and glucose metabolism is decreased in the cell following contact with the miR-208a and/or miR-208b agonist as compared to a cell not exposed to the agonist. The cell can be in vitro or in vivo. In some embodiments, the cell is, but is not limited to, a cardiomyocyte, a skeletal muscle cell, a preadipocyte, an adipocyte, a hepatocyte, or a pancreatic cell.

In some embodiments, the modulator is an inhibitor of miR-208a and/or miR-208b expression or activity, and mitochondrial function is increased in the cell following contact with the miR-208a and/or miR-208b inhibitor as compared to a cell not exposed to the inhibitor. In other embodiments, the modulator is an agonist of miR-208a and/or miR-208b expression or activity, and mitochondrial function is decreased in the cell following contact with the miR-208a and/or miR-208b agonist as compared to a cell not exposed to the agonist. The cell can be in vitro or in vivo. In some embodiments, the cell is, but is not limited to, a cardiomyocyte, a skeletal muscle cell, a preadipocyte, an adipocyte, a hepatocyte, or a pancreatic cell.

In some embodiments, the modulator is an inhibitor of miR-208a and/or miR-208b expression or activity, and redox-homeostasis is improved in the cell following contact with the miR-208a and/or miR-208b inhibitor as compared to a cell not exposed to the inhibitor. In other embodiments, the modulator is an agonist of miR-208a and/or miR-208b expression or activity, and redox-homeostasis is impaired in the cell following contact with the miR-208a and/or miR-208b agonist as compared to a cell not exposed to the agonist. The cell can be in vitro or in vivo. In some embodiments, the cell is, but is not limited to, a cardiomyocyte, a skeletal muscle cell, a preadipocyte, an adipocyte, a hepatocyte, or a pancreatic cell.

In one particular embodiment, the cell is a cardiomyocyte. Thus, the present invention also encompasses a method of regulating cardiac metabolism by contacting a cardiomyocyte with a modulator of miR-208a and/or miR-208b expression or activity. In one embodiment, contacting the cardiomyocyte with a miR-208a and/or miR-208b inhibitor prevents or reduces the metabolic shift from oxidative metabolism to glycolytic metabolism induced by a stressor. In another embodiment, contacting the cardiomyocyte with a miR-208a and/or miR-208b inhibitor reduces carbohydrate metabolism in the cardiomyocyte. In still another embodiment, contacting the cardiomyocyte with a miR-208a and/or miR-208b inhibitor increases fatty acid metabolism in the cardiomyocyte. In yet another embodiment, contacting the cardiomyocyte with a miR-208a and/or miR-208b inhibitor increases glucose metabolism in the cardiomyocyte. In one embodiment, contacting the cardiomyocyte with a miR-208a and/or miR-208b inhibitor enhances mitochondrial function in the cardiomyocyte. In another embodiment, contacting the cardiomyocyte with a miR-208a and/or miR-208b inhibitor improves redox-homeostasis in the cardiomyocyte. The cardiomyocyte can be in vitro or in vivo.

In another particular embodiment, the cell is a skeletal muscle cell. Thus, the present invention also encompasses a method of regulating metabolism in skeletal muscle by contacting a skeletal muscle cell with a modulator of miR-208a and/or miR-208b expression or activity. In one embodiment, contacting the skeletal muscle cell with a miR-208a and/or miR-208b inhibitor prevents or reduces the metabolic shift from oxidative metabolism to glycolytic metabolism induced by a stressor. In another embodiment, contacting the skeletal muscle cell with a miR-208a and/or miR-208b inhibitor reduces carbohydrate metabolism in the skeletal muscle cell. In still another embodiment, contacting the skeletal muscle cell with a miR-208a and/or miR-208b inhibitor increases fatty acid metabolism in the skeletal muscle cell. In yet another embodiment, contacting the skeletal muscle cell with a miR-208a and/or miR-208b inhibitor increases glucose metabolism in the skeletal muscle cell. In one embodiment, contacting the skeletal muscle cell with a miR-208a and/or miR-208b inhibitor enhances mitochondrial function in the skeletal muscle cell. In another embodiment, contacting the skeletal muscle cell with a miR-208a and/or miR-208b inhibitor improves redox-homeostasis in the skeletal muscle cell. In still another embodiment, contacting the skeletal muscle cell with a miR-208a and/or miR-208b inhibitor increases the level of dipeptides in the skeletal muscle cell. In still yet another embodiment, contacting the skeletal muscle cell with a miR-208a and/or miR-208b inhibitor inhibits skeletal muscle cell growth. The skeletal muscle cell can be in vitro or in vivo.

In another particular embodiment, the cell is a liver cell or hepatocyte. Thus, the present invention also encompasses a method of regulating metabolism in a liver cell by contacting a liver cell with a modulator of miR-208a and/or miR-208b expression or activity. In one embodiment, contacting the liver cell with a miR-208a and/or miR-208b inhibitor prevents or reduces the metabolic shift from oxidative metabolism to glycolytic metabolism induced by a stressor. In another embodiment, contacting the liver cell with a miR-208a and/or miR-208b inhibitor reduces carbohydrate metabolism in the liver cell. In still another embodiment, contacting the liver cell with a miR-208a and/or miR-208b inhibitor increases fatty acid metabolism in the liver cell. In yet another embodiment, contacting the liver cell with a miR-208a and/or miR-208b inhibitor increases glucose metabolism in the liver cell. In one embodiment, contacting the liver cell with a miR-208a and/or miR-208b inhibitor enhances mitochondrial function in the liver cell. In another embodiment, contacting the liver cell with a miR-208a and/or miR-208b inhibitor improves redox-homeostasis in the liver cell. The liver cell can be in vitro or in vivo.

The present invention also provides a method for preventing or treating disorders or diseases associated with a deficiency in glycolytic or fatty acid metabolism. For instance, in one embodiment, the present invention provides a method for preventing or treating hypoglycemia or hyperinsulinism in a subject in need thereof by administering to the subject a miR-208a and/or miR-208b agonist described herein. Subjects at risk of developing hypoglycemia or hyperinsulinism include diabetic patients who overdose on insulin or certain diabetes medications chlorpropamide, tolazamide, acetohexamide, glipizide, or tolbutamide), subjects who have an insulin secreting tumor (insulinoma), patients diagnosed with liver disease or genetic conditions that cause hyperinsulinism. Other disorders or conditions that may be treated or prevented with agonists of miR-208a and/or miR-208b described herein are those in which patients have difficulty maintaining a normal body weight or experience unintentional weight loss. For instance, in one embodiment, the present invention includes a method of treating or preventing hyperthyroidism (Graves' Disease) in a subject in need thereof by administering to the subject a miR-208a and/or miR-208b agonist.

miR-208a, including its structure and processing, is described in WO 2008/816924, which is hereby incorporated by reference in its entirety.

miR-208a is located within an intron of the α-MHC gene. The precise intron location is dependent on the particular species and specific transcript. For example, in humans, miR-208a is encoded within the 28th intron of the α-MHC gene, while in mice, it is encoded within the 29th intron. The pre-miRNA encoding sequences for miR-208a for human, mouse, rat, and canine are shown below as SEQ ID NO: 5, SEQ ID NO: 6, SEQ ID NO: 7, and SEQ ID NO: 8, respectively. The mature miR-208a sequence is provided in SEQ ID NO: 9. Like α-MHC, miR-208a is expressed solely in the heart.

```
Human pre-miR-208a
                                            (SEQ ID NO: 5)
ACGGGCGAGC TTTTGGCCCG GGTTATACCT GATGCTCACG

TATAAGACGA GCAAAAAGCT TGTTGGTCAG A

Mouse pre-miR-208a
                                            (SEQ ID NO: 6)
ACGGGTGAGC TTTTGGCCCG GGTTATACCT GACTCTCACG

TATAAGACGA GCAAAAAGCT TGTTGGTCAG A

Rat pre-miR-208a
                                            (SEQ ID NO: 7)
ACGGGTGAGC TTTTGGCCCG GGTTATACCT GACTCTCACG

TATAAGACGA GCAAAAAGCT TGTTGGTCAG A

Canine pre-miR-208a
                                            (SEQ ID NO: 8)
ACGCATGAGC TTTTGGCTCG GGTTATACCT GATGCTCACG

TATAAGACGA GCAAAAAGCT TGTTGGTCAG A

Mature miR-208a
                                            (SEQ ID NO: 9)
AUAAGACGAGCAAAAAGCUUGU
```

The genome contains another microRNA related to miR-208a, called miR-208b, which is located within the β-MHC gene at intron 31, and like β-MHC, miRNA 208b is expressed solely in the heart and slow skeletal muscle (e.g. soleus). Genes regulated by miR-208b include, for example, Sp3, Myostatin, PURbeta, THRAP1, and fast skeletal muscle protein genes. The sequence of this miRNA is largely overlapping with miR-208a with a 100% homology in the "seed region," the region that defines mRNA targets of a certain miRNA. The pre-miR-208b sequence is conserved across several mammalian species (e.g. human, mouse, rat, and canine). The pre-miR-208b sequence as well as the mature miR-208b sequence is shown below:

```
pre-miR-208b
                                           (SEQ ID NO: 10)
TTTCTGATCC GAATATAAGA CGAACAAAAG GTTTGTCTGA GGG Mature miR-208b
                                           (SEQ ID NO: 11)
AUAAGACGAA CAAAAGGUUU GU
```

The structure and processing of miR-208b is also described in WO 2009/018492, which is hereby incorporated by reference in its entirety. The sequences for the various forms of miR-208a and miR-208b may be used to design complementary inhibitors in accordance with the invention.

It is understood that all ribonucleic acid sequences disclosed herein can be converted to deoxyribonucleic acid sequences by substituting a thymidine base for a uridine base in the sequence. Likewise, all deoxyribonucleic acid sequences disclosed herein can be converted to ribonucleic acid sequences by substituting a uridine base for a thymidine base in the sequence. Deoxyribonucleic acid sequences, ribonucleic acid sequences, and sequences containing mixtures of deoxyribonucleotides and ribonucleotides of all sequences disclosed herein are included in the invention.

In some embodiments, an inhibitor of miR-208a and/or miR-208b suitable for use in any of the methods of the invention is an antisense oligonucleotide. The antisense oligonucleotides can include ribonucleotides or deoxyribonucleotides or a combination thereof. Preferably, the antisense oligonucleotides have at least one chemical modification (e.g., sugar or backbone modification). For instance, suitable antisense oligonucleotides can be comprised of one or more "conformationally constrained" or bicyclic sugar nucleoside modifications (BSN) that confer enhanced thermal stability to complexes formed between the antisense oligonucleotide containing BSN and their complementary microRNA target strand. For example, in one embodiment, the antisense oligonucleotide of the invention contains one or more locked nucleic acid (LNAs) residues, or "locked nucleotides." LNAs are described, for example, in U.S. Pat. No. 6,268,490, U.S. Pat. No. 6,316,198, U.S. Pat. No. 6,403,566, U.S. Pat. No. 6,770,748, U.S. Pat. No. 6,998,484, U.S. Pat. No. 6,670,461, and U.S. Pat. No. 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In exemplary embodiments, the locked nucleotides have a 2' to 4' methylene bridge, as shown in structure A, for example. In one embodiment, the antisense oligonucleotide contains the 2'-O,4'C-methylene ribonucleoside (structure A) wherein the ribose sugar moiety is in a "locked" conformation. In yet another embodiment, the antisense oligonucleotides contains a 2'-O, 4% C-ethylene-bridged nucleic acid (ENA), such as 2'-O,4'-C-ethylene ribonucleoside. Alternatively or in addition, the antisense oligonucleotide may contain at least one 2',4'-C-bridged 2' deoxyribonucleoside (cDNA, structure B). Alternatively or in addition, the antisense oligonucleotide contains one or more LNAs having the structure shown by structure C below.

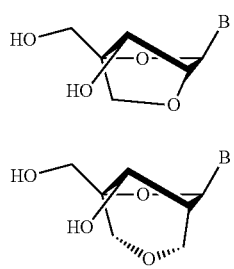

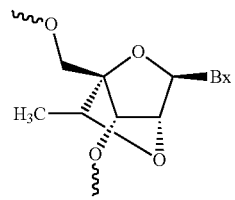

The antisense oligonucleotides targeting miR-208a and/or miR-208b can contain a BSN (LNA, ENA, cDNA and the like) and other modified nucleotides, and ribonucleotides or deoxyribonucleotides. In one embodiment, the antisense oligonucleotides targeting miR-208a and/or miR-208b contain a BSN (LNA, ENA, cDNA and the like) and a 2'-O-alkyl modification and/or 2' halo modification, such as 2'-fluoro modification. In yet another embodiment, the antisense oligonucleotides targeting miR-208a and/or miR-208b contain combinations of BSN (LNA, ENA, cDNA and the like) or other modified nucleotides, and ribonucleotides or deoxyribonucleotides. In one embodiment, the antisense oligonucleotides targeting miR-208a and/or miR-208b contain a combination of BSN (LNA, ENA, cDNA and the like) and a 2'-O-alkyl modification and/or 2' halo modification, such as 2'-fluoro modification.

In one embodiment, the antisense oligonucleotides comprise a 2'-O,4'-C-ethylene-bridged nucleic acid, such as 2'-O,4'-C-ethylene ribonucleoside, and a 2'-O,4'-C-methylene ribonucleoside. In another embodiment, the antisense oligonucleotides comprise a 2'-O,4'-C-ethylene-bridged nucleic acid, such as 2'-O, 4'-C-ethylene ribonucleoside, 2'-O,4'C-methylene ribonucleoside, and a 2'-O-alkyl modification and/or 2'-halo modification, such as 2'-fluoro modification.

Other suitable locked nucleotides that can be incorporated in the antisense oligonucleotides of the invention include those described in U.S. Pat. No. 6,403,566 and U.S. Pat. No. 6,833,361, both of which are hereby incorporated by reference in their entireties.

The antisense oligonucleotide may comprise, consist essentially of, or consist of, a sequence that is at least partially complementary to a full length or truncated miR-208a or miR-208b sequence. As used herein, the term "full length" in reference to a miRNA sequence refers to the length of the mature miRNA. Thus, the inhibitors described herein may be truncated or full-length, antisense to mature miRNA sequences, or may comprise these sequences in combination with other polynucleotide sequences. In certain embodiments, the specific chemical modification motifs described herein render frill length antisense miRNA (mature) sequences unnecessary. In these embodiments, the antisense oligonucleotide is from 8 to 20 nucleotides in length, or is from 10 to 18 nucleotides in length, or is from 11 to 16 nucleotides in length. The antisense oligonucleotide in some embodiments is about 12, about 13, about 14, about 15, about 16, about 17, or about 18 nucleotides in length. The truncated antisense oligonucleotide may have a sequence that targets, by antisense inhibition, a miR-208a sequence within 5'-UAAGACGAGCAAAAAG-3' (SEQ ID NO:7) or a miR-208b sequence within UAAGAC-GAACAAAAAG-3' (SEQ ID NO:8).

The antisense oligonucleotide generally has a nucleotide sequence designed to target mature miR-208a and/or miR-208b. The antisense oligonucleotide may, in these or other embodiments, also or alternatively be designed to target the pre-miRNA or pri-miRNA forms. In certain embodiments, the antisense oligonucleotide may be designed to have a sequence containing from 1 to 5 (e.g., 1, 2, 3, or 4) mismatches relative to the fully complementary (mature) miR-208 sequence.

In certain embodiments, the antisense oligonucleotide comprises a nucleotide sequence that is completely complementary to a nucleotide sequence of miR-208a or miR-208b. For example, the antisense oligonucleotide may comprise the nucleotide sequence of 5' TGCTCGTCTTA-3' (SEQ ID NO:1) or may comprise the nucleotide sequence of 5'-TGT-TCGTCTTA 3' (SEQ ID NO:2). In particular embodiments, the antisense oligonucleotide comprises, consists essentially of, or consists of the nucleotide sequence 5'-CTTTTT-GCTCGTCTTA-3' (SEQ ID NO:3) or '5-CCTTTTGT-TCGTCTTA (SEQ ID NO:4). In this context, "consists essentially of" includes the optional addition of nucleotides (e.g., one or two) on either or both of the 5' and 3' ends, so long as the additional nucleotide(s) do not substantially affect the antisense oligonucleotide's inhibition of the target miRNA. In one embodiment, the antisense oligonucleotide has the structure of Compound 10101, 10673, 10674, 10677, 10679, 10707, 10680, 10681, or 10683 shown in Table 1. In another embodiment, the antisense oligonucleotide has the structure of Compound 10101, 10673, 10681, or 10683 shown in Table 1. In certain embodiments, the antisense oligonucleotide has the structure of Compound 10101 or 10683 shown in Table 1.

The antisense oligonucleotide may contain at least 3, at least 5, or at least 7 locked nucleotides, but in various embodiments is not fully comprised of locked nucleotides. Generally, the number and position of locked nucleotides is such that the antisense oligonucleotide reduces miR-208a and/or miR-208b activity as determined in vitro or in vivo as described in the Examples or other methods known to those of skill in the art. In certain embodiments, the antisense oligonucleotide does not contain a stretch of nucleotides with more than four, or more than three, contiguous non-locked nucleotides. In certain embodiments, the antisense oligonucleotide does not contain a stretch of nucleotides with more than two contiguous non-locked nucleotides. For example, the antisense oligonucleotide may have just one occurrence of contiguous non-locked nucleotides. In these or other embodiments, the region complementary to the miR-208a and/or miR-208b seed region comprises at least three or at least four locked nucleotides. These embodiments may, for example, employ a nucleotide sequence of SEQ ID NO:3 or SEQ ID NO:4.

Thus, in various embodiments, the antisense oligonucleotide contains at least nine locked nucleotides, or at least eleven locked nucleotides. The antisense oligonucleotide may contain at least three non-locked nucleotides. For example, the antisense oligonucleotide may contain nine locked nucleotides and seven non-locked nucleotides, or may contain eleven locked nucleotides and five non-locked nucleotides.

The pattern of locked nucleotides may be such that at least positions 1, 6, 10, 13, and 15 are locked nucleotides. In certain embodiments, positions 1, 5, 6, 8, 10, 11, 13, 15, and 16 are locked nucleotides, and the remaining positions are non-locked nucleotides. In other embodiments, positions 1, 3, 4, 5, 6, 8, 10, 13, 15, and 16 are locked nucleotides, with the remaining positions being non-locked nucleotides. In still other embodiments, positions 1, 4, 5, 7, 9, 10, 12, 14, and 16 are locked nucleotides, with the remaining positions being non-locked nucleotides. In exemplary embodiments, such patterns find use with an antisense oligonucleotide having the sequence of SEQ ID NO:3 or SEQ ID NO:4.

For non-locked nucleotides, the nucleotide may contain a 2' modification with respect to a 2' hydroxyl. For example, the 2' modification may be 2' deoxy. Incorporation of 2'-modified nucleotides in antisense oligonucleotides may increase both resistance of the antisense oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro or in vivo.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo fluoro), and deoxy (H). For example, the 2' modifications may each be independently selected from O-methyl and fluoro. In exemplary embodiments, purine nucleotides each have a 2' OMe and pyrimidine nucleotides each have a 2'-F. In certain embodiments, from one to about five 2' positions, or from about one to about three 2' positions are left unmodified (e.g., as 2' hydroxyls).

2' modifications in accordance with the invention also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylamino-ethyloxyethyl (2'-O-DMAEOE), or 2'-O—N-methylacet-amido (2'-O—NMA) substitutions.

In certain embodiments, the antisense oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The antisense oligonucleotide may contain from 1 to about 5 2'-halo modifications (e.g., fluoro), or from 1 to about 3 2'-halo modifications (e.g., fluoro). In some embodiments, the antisense oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The antisense oligonucleotide may have one or more 2'-deoxy modifications (e.g., H for 2' hydroxyl), and in some embodiments, contains from 2 to about 10 2'-deoxy modifications at non-locked positions, or contains 2' deoxy at all non-locked positions.

In exemplary embodiments, the antisense oligonucleotide contains 2' positions modified as 2'OMe in non-locked positions. Alternatively, non-locked purine nucleotides are modified at the 2' position as 2'OMe, with non-locked pyrimidine nucleotides modified at the 2' position as 2'-fluoro.

In certain embodiments, the antisense oligonucleotide further comprises at least one terminal modification or "cap". The cap may be a 5' and/or a 3'-cap structure. The terms "cap" or "end-cap" include chemical modifications at either terminus of the antisense oligonucleotide (with respect to terminal ribonucleotides), and including modifications at the linkage between the last two nucleotides on the 5' end and the last two nucleotides on the 3' end. The cap structure as described herein may increase resistance of the antisense oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the antisense oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the antisense oligonucleotide. A phosphorothioate monophosphate is defined by the following structures, where B is base, and R is a 2' modification as described above:

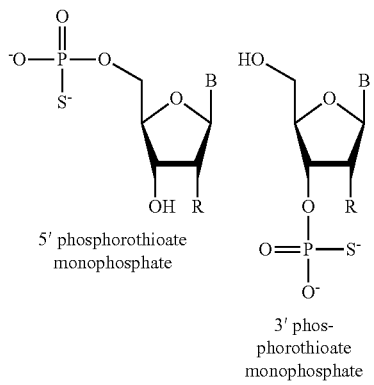

Where the cap structure can support the chemistry of a locked nucleotide, the cap structure may incorporate a locked nucleotide as described herein.

Phosphorothioate linkages may be present in some embodiments, such as between the last two nucleotides on the 5' and the 3' end as part of a cap structure), or as alternating with phosphodiester bonds. In these or other embodiments, the antisense oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

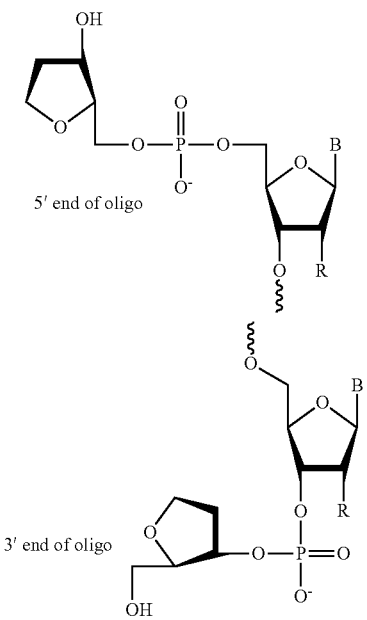

The antisense oligonucleotide may contain one or more phosphorothioate linkages. Phosphorothioate linkages have been used to render antisense oligonucleotides more resistant to nuclease cleavage. For example, the polynucleotide may be partially phosphorothioate-linked, for example, phosphorothioate linkages may alternate with phophodiester linkages. In certain embodiments, however, the antisense oligonucleotide is fully phosphorothioate-linked. In other embodiments, the antisense oligonucleotide has from one to five or one to three phosphate linkages.

In one embodiment, the invention provides a method of using chemically modified antisense oligonucleotides to inhibit the expression e.g., abundance) of miR-208 family miRNAs, including miR-208a and miR-208b. The invention provides in some embodiments, a method of using antisense oligonucleotides to inhibit, in a specific fashion, the expression or abundance of each of miR-208a and miR-208b in cardiac and/or skeletal muscle tissue. The invention further provides methods of treating patients having conditions or disorders relating to or involving a miR-208 family miRNA, such as a metabolic disorder. The invention further provides for a method of regulating fatty acid metabolism with a modulator or inhibitor of miR-208a and/or miR-208b expression or activity.

Antisense oligonucleotides used in the present invention can comprise a sequence that is at least partially complementary to a miR-208a and/or miR-208b sequence, e.g. at least about 75%, 80%, 85%, 90%, 95%, 96%, 97%, 98%, or 99% complementary to a miR-208a and/or miR-208b sequence. In some embodiments, the antisense oligonucleotide can be substantially complementary to a miR-208a and/or miR-208b sequence, that is at least about 90%, 95%, 96%, 97%, 98%, or 99% complementary to a miR-208a and/or miR-208b sequence. In one embodiment, the antisense oligonucleotide comprises a sequence that is completely complementary (i.e., 100% complementary) to a miR-208a and/or miR-208b sequence.

In some embodiments, the inhibitor of miR-208a and/or miR-208b used in the methods of the present invention is an antisense oligonucleotide that is at least partially complementary to a miR-208a or miR-208b nucleotide sequence. In other embodiments, the inhibitor of miR-208a and/or miR-208b used in the methods of the present invention is an antisense oligonucleotide that is substantially complementary to a nucleotide sequence of human miR-208a and/or miR-208b (or corresponding pre-miRNA or pri-miRNA), and may contain a mixture of locked and non-locked nucleotides optionally with a phosphorothioate backbone. For example, the antisense oligonucleotide may contain at least three, at least five or at least seven locked nucleotides, and at least one non-locked nucleotide. A substantially complementary antisense oligonucleotide may have from 1 to 4 mismatches (e.g., 1, 2, 3 or 4 mismatches) with respect to its target sequence of miR-208a or miR-208b. In exemplary embodiments, the locked nucleotides may have a 2' to 4' methylene bridge. In some embodiments, such antisense oligonucleotides having one or more locked nucleotides has a full phosphorothioate backbone.

The antisense oligonucleotide may comprise, consist essentially of or consist of a sequence at least partially complementary to a full length or truncated miR-208a or miR-208b. In these embodiments, the antisense oligonucleotide is from about 6 to 22 nucleotides in length, or is from about 10 to 18 nucleotides in length, or is about 11 to about 16 nucleotides in length. The antisense oligonucleotide in some embodiments is about 14, 15, 16, or 17 nucleotides in length. The antisense oligonucleotide may comprise the nucleotide sequence of 5'-TGCTCGTCTTA-3' (SEQ ID NO:1) or may comprise the nucleotide sequence of 5'-TGTTCGTCTTA-3' (SEQ ID NO:2). In particular embodiments, the antisense oligonucleotide comprises, consists essentially of, or consists of the nucleotide sequence 5'-CTTTTTGCTCGTCTTA-3' (SEQ ID NO:3) or 5'-CCTTTTGTTCGTCTTA-3' (SEQ ID NO:4).

The antisense oligonucleotide may also contain one or more phosphorothioate linkages. For example, the antisense oligonucleotide may be fully phosphorothioate-linked.

Exemplary inhibitors for use in the methods of the invention are antisense oligonucleotides having the structure of a compound listed in Table 1, below. Antisense oligonucleotides that reduce miR-208a and miR-208b activity are described in International Application No. PCT/US2011/065121 (published as WO2012/083005), which is hereby incorporated by reference in its entirety.

TABLE 1

Exemplary Antisense Oligonucleotide Inhibitors

| Cmpd# (M) | Alias | Sequence (5' to 3') | SEQ ID NO: | Length |
|---|---|---|---|---|
| 10101 | 208a_DNA_LNA_16_PS | lCs;dTs;dTs;dTs;lTs;lTs;dGs;lCs;dTs;lCs;lGs;dTs;lCs;dTs;lTs;lA | 13 | 16 |
| 10570 | 208fam_optdes1 | lTs;dGs;lCs;lTs;lCs;dGs;lTs;lCs;dTs;lTs;lA | 14 | 11 |
| 10571 | 208fam_optdes2 | lTs;dGs;lCs;lTs;lCs;dGs;dTs;lCs;dTs;lTs;lA | 15 | 11 |
| 10572 | 208fam_optdes3 | lTs;dGs;lCs;dAs;lCs;dGs;lTs;dCs;lTs;lTs;lA | 16 | 11 |
| 10573 | 208fam_optdes4 | lTs;lGs;dCs;dAs;lCs;lGs;dTs;lCs;dTs;lTs;lA | 17 | 11 |
| 10673 | 208a_LNA_C_T_DNA_16_1 | lCs;dTs;lTs;lTs;lTs;lTs;dGs;lCs;dTs;lCs;dGs;dTs;lCs;dTs;lTs;dA | 18 | 16 |
| 10674 | 208a_LNA_C_T_DNA_16_2 | lCs;dTs;dTs;lTs;lTs;lTs;dGs;lCs;lTs;lCs;dGs;lTs;lCs;lTS;lTs;dA | 19 | 16 |
| 10677 | 208a_LNA_C_T_DNA_16_3 | lCs;lTs;lTs;lTs;lTs;lTs;dGs;lCs;lTs;lCs;dGs;lTs;lCs;lTs;lTs;dA | 20 | 16 |
| 10679 | 208_LNA_opt_1 | lCs;dTs;lTs;dTs;lTs;lTs;dGs;lCs;dTs;lCs;dGs;lTs;dCs;lTs;lTs;dA | 21 | 16 |
| 10680 | 208_LNA_opt_2 | lCs;dTs;lTs;lTs;lTs;lTs;dGs;lCs;dTs;lCs;dGs;dTs;lCs;dTs;dTs;lA | 22 | 16 |
| 10681 | 208_LNA_opt_3 | lCs;dTs;lTs;lTs;dTs;lTs;dGs;lCs;lTs;lCs;dGs;dTs;lCs;dTs;lTs;dA | 23 | 16 |
| 10682 | 208_LNA_opt_4 | lCs;dTs;lTs;dTs;lTs;dTs;lGs;dCs;lTs;dCs;lGs;dTs;lCs;lTs;lA | 24 | 16 |
| 10683 | 208_LNA_opt_5 | lCs;dTs;dTs;lTs;lTs;dTs;lGs;dCs;lTs;lCs;dGs;lTs;dCs;lTs;dTs;lA | 25 | 16 |
| 10707 | 208b_DNA_LNA_16_PS | lCs;dCs;dTs;dTs;lTs;lTs;dGs;lTs;lGs;dTs;lCs;dTs;lCs;dTs;lTs;lA | 26 | 16 |
| 10718 | 208a_like_15_1 | lTs;lTs;lTs;lTs;lTs;dGs;lCs;dTs;lCs;dGs;dTs;lCs;dTs;lTs;dA | 27 | 15 |

TABLE 1-continued

Exemplary Antisense Oligonucleotide Inhibitors

| Cmpd# (M) | Alias | Sequence (5' to 3') | SEQ ID NO: | Length |
|---|---|---|---|---|
| 10719 | 208a like_15_2 | lTs;lTs;dTs;lTs;lTs;dGs;lCs;dts;lCs;dGs;dTs;lCs;dTs;lTs;dA | 28 | 15 |
| 10720 | 208a like_15_3 | lTs;lTs;lTs;lTs;lTs;dGs;dCs;dTs;lCs;dGs;lTs;lCs;dTs;lTs;dA | 29 | 15 |
| 10721 | 208a like_15_4 | lTs;dTs;lTs;lTs;lTs;dGs;dCs;dTs;lCs;dGs;dTs;lCs;lTs;lTs;dA | 30 | 15 |
| 10722 | 208a like_15_5 | lTs;lTs;lTs;lTs;lTs;dGs;lCs;dTs;lCs;dGs;dTs;lCs;lTs;lTs;lA | 31 | 15 |
| 10723 | 208a like_15_6 | lTs;dTs;lTs;lTs;lTs;dGs;lCs;dTs;lCs;dGs;dTs;lCs;lTs;lTs;lA | 32 | 15 |
| 10724 | 208b like_15_1 | lCs;lTs;lTs;lTs;lTs;dGs;lCs;dTs;lCs;dGs;dTs;lCs;dTs;lTs;dA | 33 | 15 |
| 10725 | 208b like_15_2 | lCs;lTs;dTs;lTs;lTs;dGs;lCs;dTs;lCs;lCs;dGs;dTs;lCs;dTs;lTs;dA | 34 | 15 |
| 10726 | 208b like_15_3 | lCs;dTs;lTs;lTs;lTs;dGs;lCs;dTs;lCs;dGs;dTs;lCs;lTs;lTs;dA | 35 | 15 |
| 10727 | 208b like_15_4 | lCs;lTs;lTs;lTs;lTs;dGs;lCs;dTs;lCs;dGs;dTs;lCs;dTs;lTs;lA | 36 | 15 |
| 10728 | 208b like_15_5 | lCs;dTs;lTs;lTs;lTs;dGs;lCs;dTs;lCs;dGs;dTs;lCs;dTs;lTs;lA | 37 | 15 |
| 10729 | 208b like_15_6 | lCs;lTs;lTs;lTs;lTs;dGs;dCs;dTs;lCs;dGs;lTs;lCs;dTs;lTs;dA | 38 | 15 |
| 10730 | 208b_15_1 | lCs;lTs;lTs;lTs;lTs;dGs;lTs;dTs;lCs;dGs;dTs;lCs;dTs;lTs;dA | 39 | 15 |
| 10731 | 208b_15_2 | lCs;lTs;lTs;lTs;lTs;dGs;lTs;dTs;lCs;dGs;dTs;lCs;dTs;lTs;lA | 40 | 15 |
| 10732 | 208b_15_3 | lCs;lTs;lTs;lTs;lTs;dGs;lTs;dTs;lCs;dGs;dTs;lCs;dTs;lTs;dA | 41 | 15 |
| 10733 | 208a like_15_7 | lTs;dTs;lTs;dTs;lTs;dGs;dCs;dTs;lCs;lGs;lTs;lCs;lTs;lTs;lA | 42 | 15 |
| 10734 | 208b like_15_7 | lCs;dTs;lTs;dTs;lTs;dGs;dCs;dTs;lCs;lGs;lTs;lCs;lTs;lTs;lA | 43 | 15 |
| 10735 | 208b_15_4 | lCs;dTs;lTs;dTs;lTs;dGs;dTs;dTs;lCs;lGs;lTs;lCs;lTs;lTs;lA | 44 | 15 |
| 10736 | 208a like_14_1 | lTs;lTs;lTs;lTs;dGs;lCs;dTs;lCs;dGs;dTs;lCs;dTs;lTs;dA | 45 | 14 |
| 10737 | 208a like_14_2 | lTs;lTs;lTs;lTs;dGs;lCs;dTs;lCs;dGs;dTs;lCs;dTs;lTs;lA | 46 | 14 |
| 10738 | 208a like_14_3 | lTs;lTs;lTs;lTs;dGs;dCs;dTs;lCs;dGs;dTs;lCs;dTs;lTs;lA | 47 | 14 |
| 10739 | 208a like_14_4 | lTs;lTs;lTs;lTs;dGs;dCs;dTs;lCs;dGs;lTs;lCs;dTs;lTs;lA | 48 | 14 |
| 10740 | 208a like_14_5 | lTs;lTs;lTs;lTs;dGs;dCs;lTs;lCs;dGs;lTs;dCs;lTs;lTs;dA | 49 | 14 |
| 10741 | 208a like_14_6 | lTs;dTs;lTs;dTs;dGs;lCs;dTs;lCs;lGs;lTs;lCs;lTs;lTs;lA | 50 | 14 |
| 10742 | 208b_14_1 | lTs;lTs;lTs;lTs;dGs;lTs;dTs;lCs;dGs;dTs;lCs;dTs;lTs;dA | 51 | 14 |
| 10743 | 208b_14_2 | lTs;lTs;lTs;lTs;dGs;lTs;dTs;lCs;dGs;dTs;lCs;dTs;lTs;lA | 52 | 14 |

TABLE 1-continued

Exemplary Antisense Oligonucleotide Inhibitors

| Cmpd# (M) | Alias | Sequence (5' to 3') | SEQ ID NO: | Length |
|---|---|---|---|---|
| 10744 | 208b_14_3 | lTs;lTs;lTs;lTs;dGs;dTs;dTs;lCs;dGs;dTs;lCs;dTs;lTs;lA | 53 | 14 |
| 10745 | 208b_14_4 | lTs;lTs;lTs;lTs;dGs;dTs;dTs;lCs;dGs;lTs;lCs;dTs;lTs;lA | 54 | 14 |
| 10746 | 208b_14_5 | lTs;lTs;lTs;lTs;dGs;dTs;lTs;lCs;dGs;lTs;dCs;lTs;lTs;dA | 55 | 14 |
| 10747 | 208b_14_6 | lts;dTs;lTs;dTs;dGs;lTs;dTs;lCs;lGs;lTs;lCs;lTs;lTs;lA | 56 | 14 |
| 10748 | 208a like_13_1 | lTs;lTs;lTs;dGs;lCs;dTs;lCs;dGs;dTs;lCs;dTs;lTs;dA | 57 | 13 |
| 10749 | 208a like_13_2 | lTs;lTs;lTs;dGs;lCs;dTs;lCs;dGs;dTs;lCs;dTs;lTs;lA | 58 | 13 |
| 10750 | 208a like_13_3 | lTs;lTs;lTs;dGs;lCs;dTs;lCs;lGs;lTs;lCs;lTs;lTs;lA | 59 | 13 |
| 10751 | 208a like_13_4 | lTs;dTs;lTs;dGs;lCs;dTs;lCs;lGs;lTs;lCs;lTs;lTs;lA | 60 | 13 |
| 10752 | 208b_13_1 | lTs;lTs;lTS;dGs;lTs;dTs;lCs;dGs;dTs;lCs;dTs;lTs;dA | 61 | 13 |
| 10753 | 208b_13_2 | lTs;lTs;lTs;dGs;lTs;dTs;lCs;dGs;dTs;lCs;dTs;lTs;lA | 62 | 13 |
| 10754 | 208b_13_3 | lTs;lTs;lTs;dGs;lTs;dTs;lCs;lGs;lTs;lCs;lTs;lTs;lA | 63 | 13 |
| 10755 | 208b_13_4 | lTs;dTs;lTs;dGs;lTs;dTs;lCs;lGs;lTs;lCs;lTs;lTs;lA | 64 | 13 |
| 10756 | 208a like_11_1 | lTs;dGs;lCs;dTs;lCs;dGs;dTs;lCs;dTs;lTs;dA | 65 | 11 |
| 10757 | 208a like_11_2 | lTs;dGs;lCs;dTs;lCs;dGs;dTs;lCs;dTs;lTs;lA | 66 | 11 |
| 10758 | 208b_11_1 | lTs;dGs;lTs;dTs;lCs;dGs;dTs;lCs;dTs;lTs;dA | 67 | 11 |
| 10759 | 208b_11_2 | lTs;dGs;lTs;dTs;lCs;dGs;dTs;lCs;dTs;lTs;lA | 68 | 11 |
| 10760 | 208b_16_1 | lCs;dCs;lTs;lTs;lTs;lTs;dGs;lTs;dTs;lCs;dGs;dTs;lCs;dTs;lTs;dA | 69 | 16 |
| 10761 | 208b_16_2 | lCs;dCs;lTs;lTs;lTs;lTs;dGs;lTs;dTs;lCs;dGs;lTs;dCs;lTs;lTs;dA | 70 | 16 |
| 10762 | 208b_16_3 | lCs;dCs;lTs;lTs;lTs;lTs;dGs;lTs;dTs;lCs;dGs;dTs;lCs;dTs;dTS;lA | 71 | 16 |
| 10763 | 208b like_16_1 | lCs;dCs;lTs;lTs;lTS;dGs;lTs;dTs;lCs;dGs;dTs;lCs;lTs;dA | 72 | 16 |
| 10764 | 208b like_16_2 | lCs;dCs;lTs;lTs;lTs;lTs;dGs;lTs;dTs;lCs;dGs;lTs;dCs;lTs;lTs;dA | 73 | 16 |
| 10765 | 208b like_16_3 | lCs;dCs;lTs;lTs;lTs;lTs;dGs;lTs;dTs;lCs;dGs;dTs;lCs;dTs;dTs;lA | 74 | 16 |
| 10775 | 208b_15_5 | lTs;lTs;lTs;lTs;dGs;lTs;dTs;lCs;dGs;dTs;lCs;dTs;lTs;dAs;lT | 75 | 15 |
| 10776 | 208b_15_6 | lTs;lTs;lTs;lTs;dGs;lTs;dTs;lCs;dGs;dTs;lCs;dTs;lTs;lAs;lT | 76 | 15 |
| 10777 | 208b_15_7 | lTs;lTs;lTs;lTs;dGs;lTs;dTs;lCs;dGs;lTs;lCs;dTs;lTs;dAs;lT | 77 | 15 |
| 10778 | 208b_15_8 | lTs;lTs;dTs;lTs;dGs;dTs;dTs;lCs;lGs;lTs;lCs;lTs;lTs;lAs;lT | 78 | 15 |

TABLE 1-continued

Exemplary Antisense Oligonucleotide Inhibitors

| Cmpd# (M) | Alias | Sequence (5' to 3') | SEQ ID NO: | Length |
|---|---|---|---|---|
| 10779 | 208b_15_9 | lTs;lTs;lTs;lTs;dGs;lTs;dTs;lCs;dGs;dTs;lCs;dTs;lTs;lAs;dT | 79 | 15 |
| 10780 | 208b_15_10 | lTs;lTs;lTs;lTs;dGs;lTs;dTs;lCs;dGs;lTs;lCs;dTs;lTs;lAs;dT | 80 | 15 |
| 10781 | 208b_15_11 | lTs;lTs;dTs;lTs;dGs;lTs;dTs;lCs;lGs;lTs;lCs;lTs;lTs;lAs;dT | 81 | 15 |
| 10782 | 208b_15_12 | lTs;lTs;lTs;lTs;dGs;dTs;dTs;lCs;dGs;dTs;lCs;lTs;lTs;dAs;lT | 82 | 15 |
| 10783 | 208b_15_13 | lTs;lTs;lTs;lTs;dGs;dTs;dTs;lCs;dGs;dTs;lCs;lTs;lTs;lAs;dT | 83 | 15 |
| 10784 | 208b_14_7 | lTs;lTs;lTs;dGs;lTs;dTs;lCs;dGs;dTs;lCs;dTs;lTs;dAs;lT | 84 | 14 |
| 10785 | 208b_14_8 | lTs;lTs;lTs;dGs;lTs;dTs;lCs;dGs;dTs;lCs;dTs;lTs;lAs;lT | 85 | 14 |
| 10786 | 208b_14_9 | lTs;lTs;lTs;dGs;lTs;dTs;lCs;dGs;lTs;lCs;dTs;lTs;dAs;lT | 86 | 14 |
| 10787 | 208b_14_10 | lTs;dTs;lTs;dGs;dTs;dTs;lCs;lGs;lTs;lCs;lTs;lTs;lAs;lT | 87 | 14 |
| 10788 | 208b_14_11 | lTs;lTs;lTs;dGs;lTs;dTs;lCs;dGs;dTs;lCs;dTs;lTs;lAs;dT | 88 | 14 |
| 10789 | 208b_14_12 | lTs;lTs;lTs;dGs;lTs;dTs;lCs;dGs;lTs;lCs;dTs;lTs;lAs;dT | 89 | 14 |
| 10790 | 208b_14_13 | lTs;dTs;lTs;dGs;lTs;dTs;lCs;lGs;lTs;lCs;lTs;lTs;lAs;dT | 90 | 14 |
| 10791 | 208b_14_14 | lTs;lTs;lTs;dGs;dTs;dTs;lCs;dGs;dTs;lCs;lTs;lTs;dAs;lT | 91 | 14 |
| 10792 | 208b_14_15 | lTs;lTs;lTs;dGs;dTs;dTs;lCs;dGs;dTs;lCs;lTs;lTs;lAs;dT | 92 | 14 |
| 10793 | 208b_16_4 | lCs;dTs;lTs;lTs;lTs;lGs;dTs;lTs;dCs;lGs;dTs;dCs;lTs;dTs;lAs;dT | 93 | 16 |

TABLE 2

Description of Notations in Table 1

| | |
|---|---|
| deoxy A | dA |
| deoxy G | dG |
| deoxy C | dC |
| deoxy T | dT |
| lna A | lA |
| lnaG | lG |
| lna C | lC |
| lna T | lT |
| deoxy A P = S | dAs |
| deoxy G P = S | dGs |
| deoxy C P = S | dCs |
| deoxy T P = S | dTs |
| lna A P = S | lAs |
| lnaG P = S | lGs |
| lna C P = S | lCs |
| lna T P = S | lTs |

In particular embodiments, the antisense oligonucleotide is 10101, 10673, 10674, 10677, 10679, 10707, 10680, 10681, or 10683, or other antisense oligonucleotide described in Table 1.

The synthesis of antisense oligonucleotides, including modified polynucleotides, by solid phase synthesis is well known and is reviewed in *New Chemical Methods for Synthesizing Polynucleotides*. Caruthers M H, Beaucage S L, Efcavitch J W, Fisher E F, Matteucci M D, Stabinsky Y. Nucleic Acids Symp. Ser. 1980; (7):215-23.

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides can contain include, but are not limited to, sugar modifications, such as 2'-O-alkyl 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In one embodiment, antisense oligonucleotides targeting miR-208a and/or miR-208b contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5 and 3' ends with at least ten deoxyribonucleotides in the center. These "gapmers" are capable of triggering RNase dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

In some embodiments, the antisense oligonucleotides are antagomirs. "Antagomirs" are single-stranded, chemically-modified ribonucleotides that are at least partially complementary to a miR-208a and/or miR-208b sequence. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting miR-208a and/or miR-208b can be about from 8 to 20 nucleotides in length, or is from 10 to 18 nucleotides in length, or is from 11 to 16 nucleotides in length. The antagomirs can be at least about 75%, 80%, 85%, 90%, 95%, 96%, 97%, 98%, or 99% complementary to a miR-208a or miR-208b sequence. In some embodiments, the antagomir may be substantially complementary to a miR-208a or miR-208b sequence, that is at least about 95%, 96%, 97%, 98%, or 99% complementary to a target polynucleotide sequence. In other embodiments, the antagomirs are 100% complementary to a miR-208a or miR-208b sequence. Antagomirs may comprise a sequence that is substantially complementary to a precursor miRNA sequence (pre-miRNA) or primary miRNA sequence (pri-miRNA) for miR-208a or miR-208b.

Also provided herein are agonists of miR-208a and miR-208b. An agonist of miR-208a and/or miR-208b expression or activity can be a polynucleotide comprising a miR-208a and/or miR-208b sequence. For instance, in one embodiment the miR-208a agonist is a polynucleotide comprising a miR-208a sequence, such as SEQ ID NO: 5-9. In one embodiment, the agonist is a polynucleotide comprising a mature miR-208a sequence, such as SEQ ID NO: 9. In still another embodiment, the miR-208a agonist can be a polynucleotide comprising the pre-miRNA sequence for miR-208a, such as SEQ ID NO: 5. In another embodiment, the miR-208b agonist is a polynucleotide comprising a miR-208b sequence. In one embodiment, the agonist is a polynucleotide comprising a mature miR-208b sequence, such as SEQ ID NO: 11. In still another embodiment, the miR-208b agonist can be a polynucleotide comprising the pre-miRNA sequence for miR-208b, such as SEQ ID NO: 10.

The polynucleotide comprising a miR-208a and/or miR-208b sequence can be from about 18 to about 2000 nucleotides in length, about 70 to about 200 nucleotides in length, about 20 to about 50 nucleotides in length, or about 18 to about 25 nucleotides in length. The polynucleotides comprising the mature miR-208a, mature miR-208b, pre-miR-208a, or pre-miR-208b sequence can be single stranded or double-stranded. The polynucleotides can contain one or more chemical modifications, such as locked nucleic acids, peptide nucleic acids, sugar modifications, such as 2%0-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-208 sequence (e.g., mature miR-208a, mature miR-208b, pre-miR-208a, or pr2-miR-208b) is conjugated to a steroid, such as cholesterol, a vitamin, a fatty acid, a carbohydrate or glycoside, a peptide, or another small molecule ligand.

Any of the inhibitors or agonists of miR-208a and/or miR-208b described herein can be delivered to the target cell (e.g. heart or skeletal muscle cell) by delivering to the cell an expression vector encoding the miR-208a and/or miR-208b inhibitors or agonists or by delivering the inhibitor or agonist itself directly to the target cell. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor or agonist of miR-208a and/or miR-208b comprises a promoter operably linked to a polynucleotide encoding an antisense oligonucleotide or agonist oligonucleotide. In one embodiment, an expression vector for expressing an inhibitor of miR-208a and/or miR-208b comprises a promoter operably linked to a polynucleotide encoding an antisense oligonucleotide, wherein the sequence of the expressed antisense oligonucleotide is partially or perfectly complementary to a mature sequence of miR-208a (e.g., SEQ ID NO: 9) or a mature sequence of miR-208b (SEQ ID NO: 11). In another embodiment, an expression vector for expressing a polynucleotide comprising a miR-208a sequence comprises a promoter operably linked to a polynucleotide comprising a human pre-miR-208a sequence (e.g., SEQ ID NO: 5). In another embodiment, an expression vector for expressing a polynucleotide comprising a miR-208b sequence comprises a promoter operably linked to a polynucleotide comprising a pre-miR-208b sequence (e.g., SEQ ID NO: 10). The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol III, and viral promoters (e.g. human cytomegalovirus (CMV) immediate early gene promoter, the SV40 early promoter, and the Rous sarcoma virus long terminal repeat). In one embodiment, the promoter is a tissue-specific promoter. Of particular interest are muscle specific promoters, and more particularly, cardiac specific promoters. These include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49):31688-31694), the troponin 1 promoter (Bhavsar et al. (1996) *Genomics*, Vol. 35(1):11-23); the Na+/Ca2+ exchanger promoter (Barnes et al. (1997) *J. Biol. Chem.*, Vol; 272(17): 11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem.*, Vol. 271(37):22915-22), the brain natriuretic peptide promoter (LaPointe et al. (1996) *Hypertension*, Vol. 27(3 Pt 2):715-22) and the alpha B-crystallin/small heat shock protein promoter (Gopal-Srivastava (1995) *J. Cell. Biol.*, Vol. 15(147081-7090), alpha myosin heavy chain promoter (Yamauchi-Takihara et al. (1989) *Proc. Natl. Acad. Sci. USA*, Vol. 86(10):3504-3508) and the ANF promoter (LaPointe et al., (1988) *J. Biol. Chem.*, Vol. 263(19):9075-9078). In one embodiment, the tissue-specific promoter is an adipocyte-specific promoter, such as an adipocyte protein 2 (ap2)/fatty acid binding protein 4 (FABP4) promoter or a PPARγ promoter.

In certain embodiments, the promoter operably linked to a polynucleotide encoding a miR-208a and/or miR-208b inhibitor or a polynucleotide encoding a miR-208a or miR-208b sequence can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes methods for scavenging or clearing miR-208a and/or miR-208b inhibitors following treatment. The method may comprise overexpressing binding sites for the miR-208a and/or miR-208b inhibitors in cardiac or skeletal muscle tissue. The binding site regions preferably contain a sequence of the seed region for miR-208a and/or 208b. The seed region is the 5' portion of a miRNA spanning bases 2-8, which is important for target recognition. In some embodiments, the binding site may contain a sequence from the 3'UTR of one or more targets of miR-208a and/or miR-208b, such as thyroid hormone receptor associated protein 1 (THRAP1, a.k.a MED13), Sox6, Sp3, Myostatin, PURbeta, and the fast skeletal muscle protein genes.

The inhibitors (such as antisense oligonucleotides) or agonists of the present invention may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

The composition or formulation may employ a plurality of therapeutic antisense oligonucleotides, including at least one described herein. For example, the composition or formulation may employ at least 2, 3, 4, or 5 miRNA inhibitors or agonists described herein.

The inhibitors (such as antisense oligonucleotides) or agonists of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are hereby incorporated by reference in their entireties.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor antisense oligonucleotide or agonist (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac or skeletal muscle tissue). The stability and/or potency of the antisense oligonucleotides disclosed herein allows for convenient routes of administration, including subcutaneous, intradermal, and intramuscular. Pharmaceutical compositions comprising miRNA inhibitors may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416, 510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

In certain embodiments, the antisense oligonucleotide is administered at a dose of 25 mg/kg or less, or a dose of 10 mg/kg or less, or a dose of 5 mg/kg or less. In these embodiments, the antisense oligonucleotide or composition may be administered by intramuscular or subcutaneous injection, or intravenously.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

All publications, patents and patent applications, including any drawings and appendices, herein are incorporated by reference to the same extent as if each individual publication or patent application was specifically and individually indicated to be incorporated by reference.

This invention is further illustrated by the following additional examples that should not be construed as limiting. Those of skill in the art should, in light of the present disclosure, appreciate that many changes can be made to the specific embodiments which are disclosed and stilt obtain a like or similar result without departing from the spirit and scope of the invention.

EXAMPLES

Example 1

AntimiR-208 Inhibits Age-Induced Weight Gain

While studying the potential therapeutic effects of miR-208 inhibitors in mice, we observed that animals treated for long term studies with antimiR-208 did not show the age-induced increase in body weight that mice normally show, while control treated (M-10591), or mice treated with saline did. Treatment was started at 8 weeks of age (body weight between 20-25 grams) and continued for up to 6 months, during which the mice received a loading dose of 3×25 mg/kg at day 1, 2 and 3 and 25 mg/kg every other week of either antimiR-208 (M-10101), non-targeting control (M-10591), or a comparable volume of saline. M-10591 targets a *C. elegans*-specific miRNA and has the following sequence: TCCTAGAAAGAGTAGA (SEQ ID NO: 12). Like M-10101, M-10591 also contains 9 LNA-modified nucleotides and is 16 nucleotides in length. Mice treated with M-10101 showed a significantly higher heart-to-body weight ratio compared to either control treated or saline injected animals. This difference was not due to an increase in heart weight (HW), hut rather due to a smaller increase in body weight (BW) during the course of the study (FIG. 1).

Figure 2:
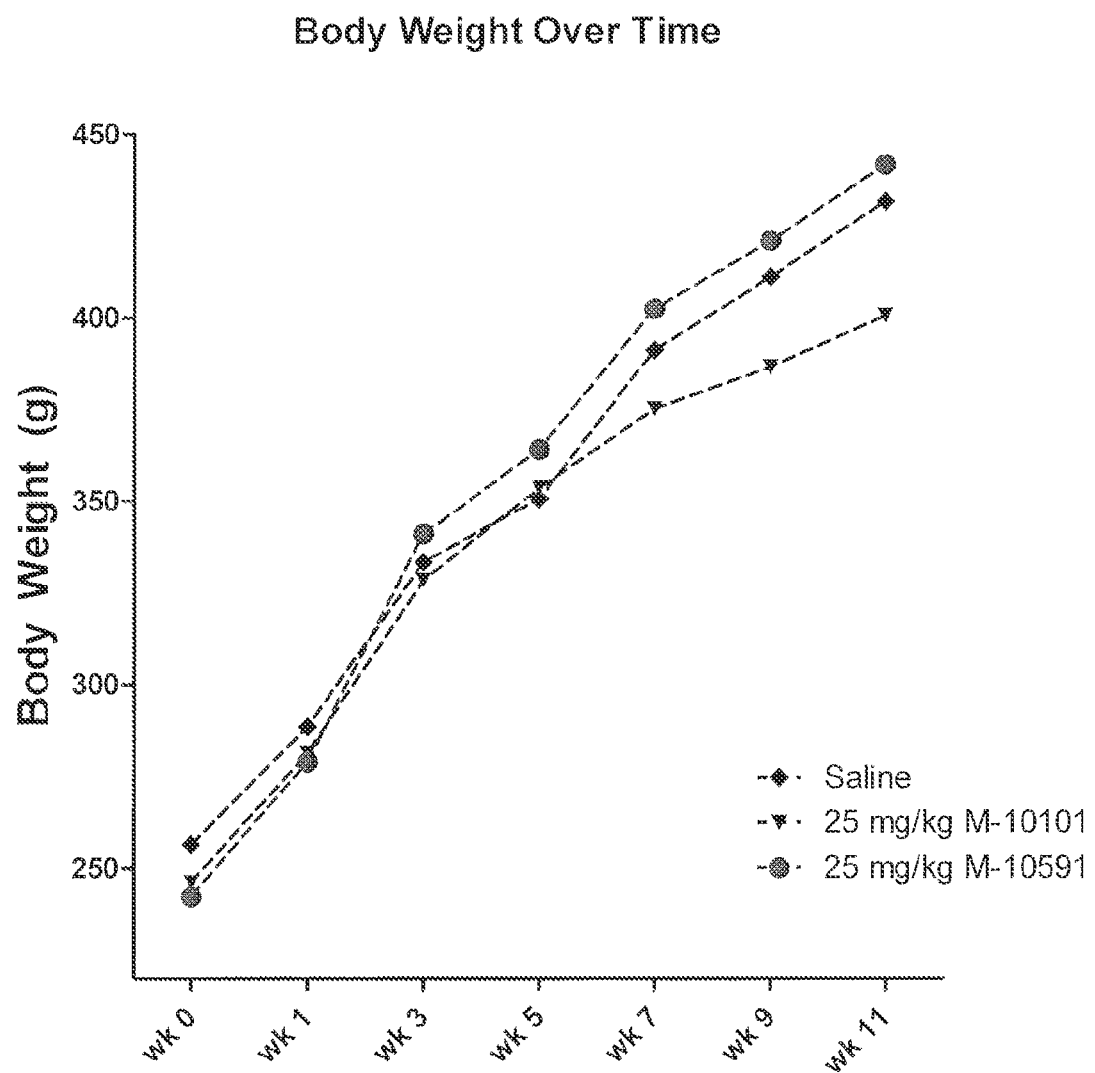
FIG. 2. AntimiR-208a (M-10101) reduces age-induced weight gain in rats. Dosing male adult rats with either antimiR-208a (M-10101), control (M-10591) or saline every 2 weeks for 11 weeks shows that antimiR-208a reduces age-induced increase in body weight.

A comparable observation was made when we dosed 8 week old male Wistar rats for an extended period of time with 25 mg/kg of M-10101 every 2 weeks, while this effect was not observed in the M-10591-treated groups (FIG. 2).

Example 2

AntimiR-208 Confers Resistance to High Fat Diet-Induced Obesity

Figure 3:
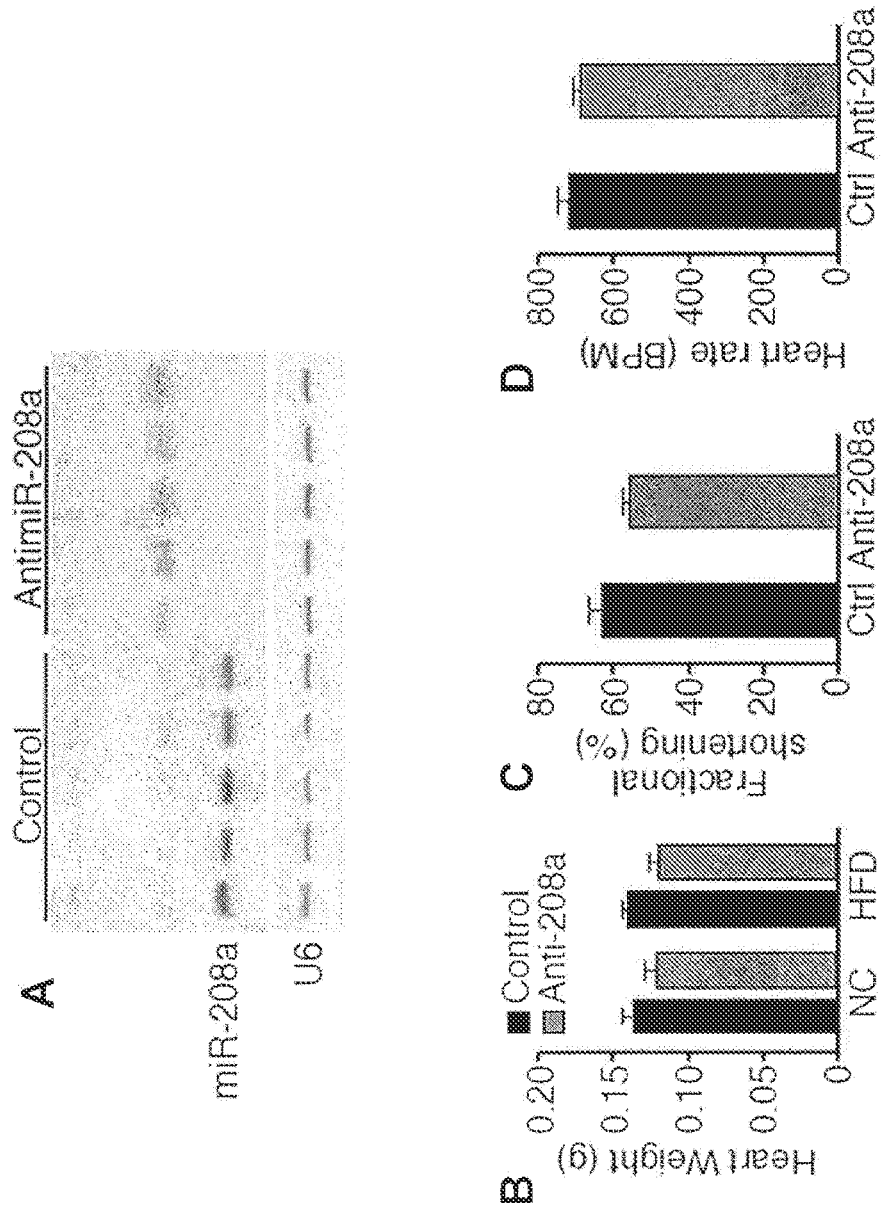
FIG. 3. A. Northern blot analysis of mice treated for 6 weeks with antimiR-208a or control antimiR (control). U6 RNA was detected as a loading control. Hearts from 5 mice from each treatment were analyzed. Note the absence of miR-208a in antimiR-208a-treated hearts. B. Heart weight from antimiR-208a and control antimiR treated mice on normal chow (NC) or high fat diet (HF) for 6 weeks. (n=5-13). C. Fractional shortening for antimiR-208a and control antimiR treated mice on NC for 6 weeks. (n=5), D. Heart rate in beats per minute for antimiR-208a and control antimiR treated mice on NC for 6 weeks. (n=5).

To determine the effects of long-term treatment with an antimiR-208a oligonucleotide, six week old, male C57Bl6 mice were injected subcutaneously with 10 mg/kg of an INA modified antimiR-208a (M-10101) dissolved in saline or a control oligonucleotide directed against a *C. elegans*-specific miRNA (M-10591). The mice were injected for three consecutive days and then given a weekly maintenance injection throughout the experiment. Subcutaneous delivery of antimiR-208a (M-10101) efficiently inhibited miR-208a levels in the heart, as detected by Northern blot analysis (FIG. 3A). Treatment of mice for 6 weeks with antimiR-208a or the control antimiR had no effect on heart weight, cardiac contractility or heart rate (FIG. 3 B-D).

To further investigate the role of miR-208a in regulating body weight and metabolism, we tested the effect of anti-miR-208a on weight gain in response to high fat (HF) diet. Six week-old male C57Bl6 mice were injected subcutaneously with 10 mg/kg body weight of antimiR 208a (M-10101) or control antimiR (M-10591) for three consecutive days. On the third day, the mice were placed on either a HF diet (60% kcal/fat) or normal chow (NC; 10% kcal/fat). The mice were weighed and given maintenance doses of 10 mg/kg weekly throughout the study. Mice on HF diet and treated with the control antimiR increased their bodyweight by 75% within six weeks, whereas antimiR-208a-treated mice on HF diet showed only a 29% increase in body weight (FIG. 4A-B), which was comparable to mice maintained on normal chow and treated with the control antimiR or anti-miR-208a (28% and 25%, respectively).

NMR spectrometry revealed the difference in weight between the treatment groups was due to differences in fat weight represented by the white sections in each bar of FIG. 4C. Consistent with these findings, visceral white adipose and subscapular adipose tissue, containing both white and brown fat, were significantly smaller in antimiR-208a treatment groups on HF diet and NC compared to the control antimiR treated animals, based on fat mass and adipocyte size (FIG. 4D-G). Serum triglyceride and cholesterol levels were also reduced in antimiR-208a treated mice on HF diet (FIGS. 4H and 4I). Similarly, hepatic steatosis seen in control animals on HF diet was blunted by treatment with antimiR-208a (FIG. 4F).

HF diet-induced obesity causes glucose intolerance. Anti-miR-208a treated mice on NC showed a normal glucose response, as measured by glucose tolerance test (GTT) (FIG. 5A). Glucose tolerance tests were performed following overnight fasting. Baseline measurements were taken using an Accu-Chek Compact Plus glucometer (Roche). Mice were subsequently injected with 1 mg/g glucose intraperitoneally. Glucose levels were then measured at 15, 30, 60 and 120 minutes following glucose injection. On HF diet, control antimiR-treated, obese mice displayed an increase in fat mass and glucose intolerance (FIGS. 4D and 5A). In contrast, antimiR-208a treated mice showed a normal glucose response after 6 weeks of HF diet as revealed by GTT and the calculated area under the curve (FIGS. 5A and 5B).

Fasting insulin levels from antimiR-208a treated mice were significantly lower than those of control antimiR treated mice (FIG. 5C). Similarly, levels of leptin, an adipocyte-derived circulating hormone that reflects body lipid content (Frederich et al., Nat. Med., Vol. 1: 1311-1314, 1995), were reduced by antimiR-208a compared to control antimiR in animals on NC and HF diet (FIG. 5D). AntimiR-208a had no effect on physical activity or food consumption (data not shown). These findings suggest that miR-208a inhibition improves whole-body insulin sensitivity. Because miR-208a is only expressed in cardiomyocytes (Callis et al., J. Clin. Invest., Vol. 119: 2772-2786, 2009; van Rooij et al., Science, Vol. 316: 575-579, 2007), the beneficial metabolic effects of antimiR-208a suggest a potential influence of the heart on systemic metabolism.

The results of this series of experiments show that pharmacologic inactivation of miR-208a, which is cardiac-specific, through systemic delivery of an antimiR confers an enhanced metabolic phenotype, suggesting that miR-208a inhibitors may have therapeutic usefulness in a variety of metabolic disorders, such as obesity, hypercholesterolemia, type 2 diabetes, hepatic steatosis and hyperlipidemia.

Example 3

AntimiR-208 Compounds Regulate Metabolism

To identify other chemically-modified antisense oligonucleotide inhibitors of miR-208a that are efficacious for regulating metabolism, mice on a high-fat diet received one of four different antimiR-208 inhibitors, two of which previously exhibited target de-repression in vivo (M-10101 and M-10683) and two of which previously did not exhibit target de-repression in vivo (M-10673 and M-10681). Four other groups of mice received one of four control oligonucleotides (M-10591, M-10649, M-10702, and M-11182). C57Bl/6 mice at 6-8 weeks of age were fed a 60% high-fat (HF) diet or regular chow and received a 25 mg/kg subcutaneous dose of an antimiR oligonucleotide every week. The treatment groups are listed in Table 3:

TABLE 3

Treatment Groups for AntimiR-208 Compound Identification

| Group | Number of Animals | Diet | Chemistry | Sequence (5' to 3')[1] | Alias |
|---|---|---|---|---|---|
| 1 | 8 | Reg Chow | saline | | |
| 2 | 8 | High Fat | saline | | |
| 3 | 8 | High Fat | M-10101 | 1Cs;dTs;dTs;dTS;1Ts;1Ts;dGs;1Cs;dTs;1Cs; 1Gs;dTs;1Cs;dTs;1Ts;1A (SEQ ID NO: 13) | Trunc_208_PS |

TABLE 3-continued

Treatment Groups for AntimiR-208 Compound Identification

| Group | Number of Animals | Diet | Chemistry | Sequence (5' to 3')[1] | Alias |
|---|---|---|---|---|---|
| 4 | 8 | High Fat | M-10673 | lCs;dTs;lTs;lTs;lTs;lTs;dGs;lCs;dTs;lCs; dGs;dTs;lCs;dTs;lTs;dA (SEQ ID NO: 18) | 208a LNA C_T_DNA_16_1 |
| 5 | 8 | High Fat | M-10681 | lCs;dTs;lTs;lTs;dTs;lTs;dGs;lCs;lTs;lCs; dGs;dTs;lCs;dTs;lTs;dA (SEQ ID NO: 23) | 208_LNA_opt_3 |
| 6 | 8 | High Fat | M-10683 | lCs;dTs;dTs;lTs;lTs;dTs;lGs;dCs;lTs;lCs; dGs;lTs;dCs;lTs;dTs;lA (SEQ ID NO: 25) | 208_LNA_opt_5 |
| 7 | 8 | High Fat | M-10591 | lTs;dCs;dCs;lTs;lAs;dGs;lAs;lAs; dAs;lGs;lAs;dGs;dTs;lAs;dGs;lA (SEQ ID NO: 94) | Control; Trunc 16mer_UnivMM |
| 8 | 8 | High Fat | M-10649 | lCs;dCs;lTs;dAs;dGs;lAs;lAs;dAs;dGs; lAs;dGs;lTs;dAs;lGs;lGs;lA (SEQ ID NO: 95) | Control; trunc 15mer_Univ |
| 9 | 8 | High Fat | M-10702 | lAs;dCs;lTs;dTs;lTs;lTs;dGs;lTs;dGs;lTs; lAS;dGs;lTs;dAs;dCs;lA (SEQ ID NO: 96) | Control; UnivCont2_16mer |
| 10 | 8 | High Fat | M-11182 | lCs;dTs;lTs;dTs;dTS;lGS;lTs;dGs;dTs;lAs; dGs;lTs;dAs;lCs;lA (SEQ ID NO: 97) | Control; UnivCont2_15mer |

[1]Notations are defined in Table 2.

Figure 7:
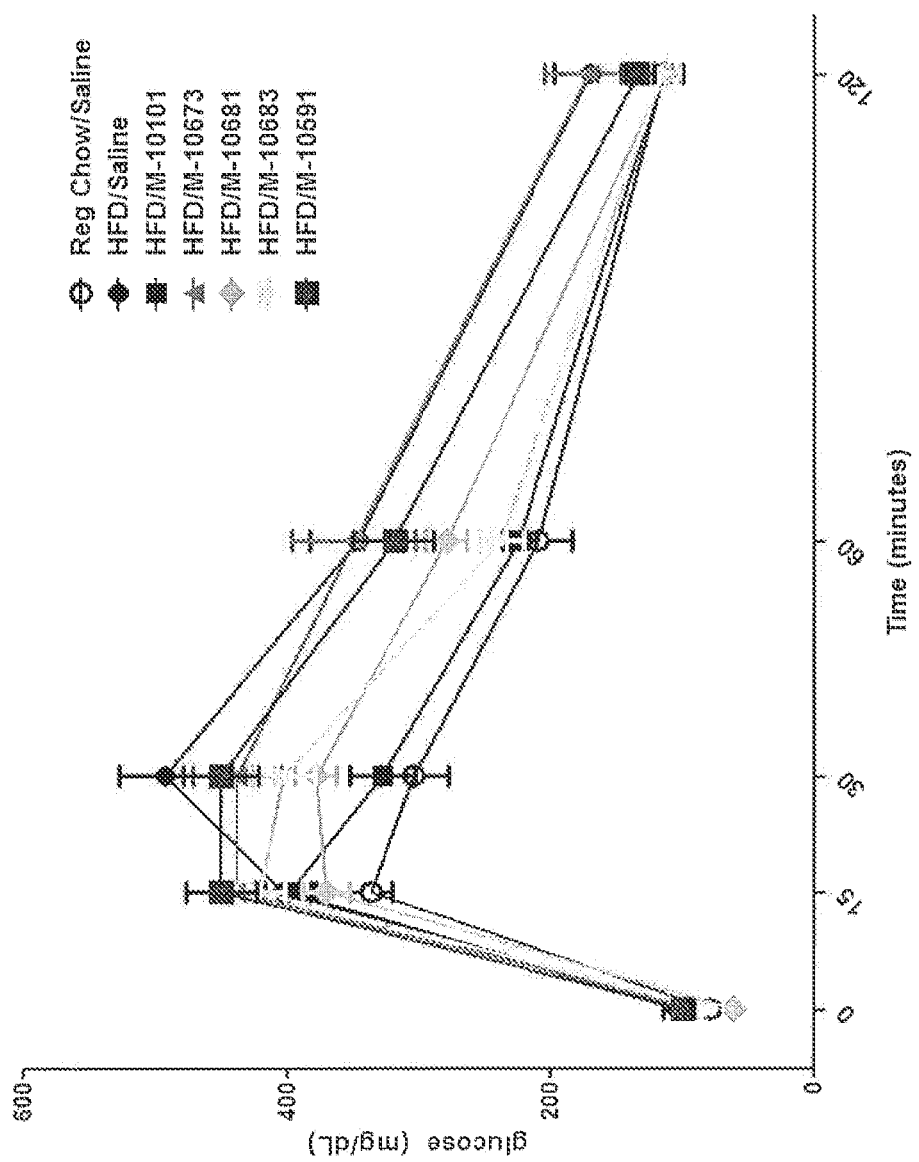
FIG. 7. miR-208a inhibition enhances glucose tolerance. Glucose tolerance test from control antimiR (M-10591) and antimiR-208a (M-10101, M-10673, M-10681, M-10683) treated mice on regular chow and 11 weeks after a high-fat diet (HFD).

All antimiR-208a compounds had an effect on reducing body weight (FIGS. 6A and 6B). M-10101 and M-10683 were the most efficacious and mice receiving these inhibitors exhibited body weights comparable to saline-treated mice on a normal diet. M-10673 and M-10681 appeared to have an intermediate effect on weight gain. A glucose tolerance test performed after 11 weeks of high fat diet and antimiR treatment with all antimiR-208a compounds showed that all antimiR-208a compounds had some effect on glucose tolerance with the M-10101 being the most efficacious (FIG. 7). Molecular analyses showed all antimiR-208a compound treated groups to have robust inhibition of miR-208a in the heart, and all antimiR-208a treated groups showed significant de-repression of Sox6, a validated miR-208a target (data not shown).

In summary, all antimiR-208a compounds reduced high fat diet-induced weight gain over time, with M-10101 and M-10683 being the most efficacious of the miR-208a inhibitors tested. These same two compounds showed the best target de-repression in rat cardiac tissue (data not shown).

In the next series of experiments, a reversal study was performed to determine whether antimiR-208a compounds could reduce body weight in animals who were already obese. Mice were subjected to a high fat diet until they reached ~45 grams. At this point, the mice received one of four antimiR-208a compounds (M-10101, M-10683, M-10673, and M-10681) subcutaneously at 25 mg/kg weekly. Mice were maintained on the high-fat diet during the experiment. The treatment groups are listed in Table 4:

TABLE 4

Treatment Groups for Reversal Study

| Group | Number of Animals | Diet | Chemistry | SEQ ID NO: | Alias |
|---|---|---|---|---|---|
| 1 | 7 | High Fat | M-10101 | 13 | Trunc_208_PS |
| 2 | 8 | High Fat | M-10673 | 18 | 208a LNA C_T_DNA_16_1 |
| 3 | 7 | High Fat | M-10681 | 23 | 208_LNA_cpt_3 |
| 4 | 7 | High Fat | M-10683 | 25 | 208_LNA_opt_5 |
| 5 | 8 | High Fat | M-10591 | 94 | Trunc 16mer_UnivMM |

Figure 8:
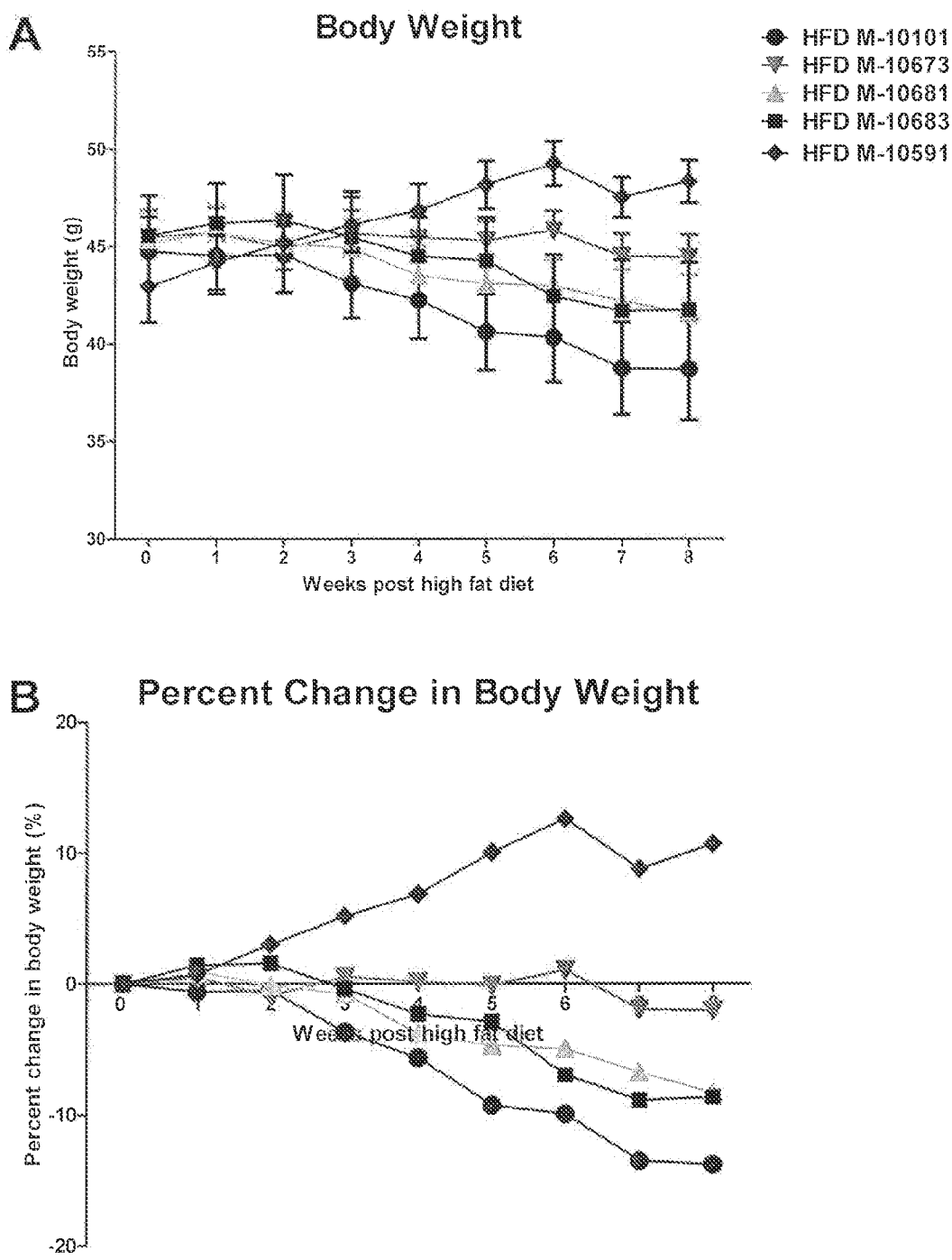
FIG. 8. Body weight over time (A) and percent change in body weight (B) of obese mice receiving control antimiR (M-10591) or one of four antimiR-208a compounds (M-10101, M-10673, M-10681, M-10683).

Weekly body weight measurements revealed that all antimiR-208a compounds reduced body weight in obese mice (FIG. 8). M-10101 was the most efficacious compound as treatment with this compound resulted in a ~10 percent loss of body weight in obese mice. This weight loss occurred while the mice continued on a high fat diet. Conversely, mice treated with a control oligo (M-10591) continued to gain weight on a high fat diet. The three other antimiR-208a compounds showed intermediate effects on weight loss, however, all compounds reduced further weight gain.

The data from the studies described in this Example demonstrate that antisense oligonucleotide inhibitors of miR-208a play an important role in regulating metabolism and can serve as an effective therapeutic for preventing and treating obesity and related metabolic disorders.

Example 4

AntimiR-208 Promotes Hepatic Energy Metabolism and Mitochondrial Function

Six mice per group were treated with high-fat diet (HFD) alone (control) or HFD in combination with the antimiR-208a M-10101. The samples were initially blinded in which following biochemical identification and data curation, the samples were "unblinded" for data analysis, revealing Group 1 as HFD+antimiR-208a and Group 2 as HFD only (control).

Following treatment, plasma, heart, skeletal muscle, liver and retroperitoneal fat were collected from each animal: snap frozen and sent to Metabolon (Durham, N.C.) for metabolomic analysis. A total of 60 samples were analyzed in this study. Samples consisted of 2 distinct treatment groups [HFD+antimiR-208a (Group1) vs. RFD Controls (Group2)] at one time point (1 week) with six replicates for each matrix (plasma, heart, skeletal muscle, liver and fat). The samples were extracted and split into equal parts for analysis on the GC/MS and LC/MS/MS platforms. Software was used to match ions to an in-house library of standards for metabolite identification and for metabolite quantitation by peak area integration. The identification and relative quantitation of metabolites for the samples was accomplished with Metaholon's technology platforms, which detected a total of 327, 275, 260, 314 and 234 biochemicals in plasma, heart, skeletal muscle, liver and retroperitoneal fat; respectively. Biochemical data were analyzed by Welch's two-sample t-tests. Welch's two-sample t-tests were used to identify biochemicals whose relative levels differed between the various treatment groups.

For quality control, a number of internal standards were added to each experimental and process standard sample prior to injection into the mass spectrometers. A measure of the platform variability was determined by calculating the median relative standard deviation (RSD) for these internal standards. Table 5 shows the median relative standard deviation (RSD) for the internal standards. Because these standards are added to the samples immediately prior to injection into the instrument, this value reflects instrument variation. In addition, the median relative standard deviation (RSD) for the biochemicals that were consistently measured in the CMTRX ("Client Matrix" samples, created from a separate aliquot of each experimental plasma sample and pooled. These CMTRX samples were injected throughout the platform run and served as technical replicates) represents the total variability within the process for the actual experimental samples and the variability in quantitation of the endogenous metabolites within these samples (Table 5). Results for the CMTRX and internal standards indicated that the platform produced data that met process specifications.

TABLE 5

Quality Control Statistics

| Quality Control | Median RSD | | | | |
|---|---|---|---|---|---|
| Sample (Matrix) | Heart | Retroperitoneal Fat | Liver | Skeletal Muscle | Plasma |
| Internal Standards | 6% | 6% | 5% | 6% | 5% |
| Endogenous Biochemicals | 11% | 11% | 10% | 14% | 9% |

For the liver samples, 36 of the 314 biochemicals identified showed a significant difference between HFD mice receiving antimiR-208a vs. HFD controls. For biochemicals involved in glucose metabolism and pyruvate incorporation into the TCA cycle, an increase in early intermediates of the glycolytic pathway with a concurrent maintenance of downstream metabolites was seen, as shown in Table 6, in which the relative fold of change for each metabolite is provided.

TABLE 6

Relative Fold Change for Metabolite in Hepatic Glucose Metabolism

| Sub Pathway | Biochemical | Group 1/Group 2 (relative fold of change) |
|---|---|---|
| Glycolysis, gluconegenesis, pyruvate metabolishm | 1,5-anhydroglucitol (1,5-AG) | 0.86 |
| | glycerate | 0.94 |
| | glucose-6-phosphate (G6P) | 1.62 |
| | glucose | 1.06 |
| | fructose-6-phosphate | 1.45 |
| | Isobar: fructose 1,6-diphosphate, glucose 1,6-diphosphate, myo-inositol 1,4, or 1,3-diphosphate | 2.09 |
| | 3-phosphoglycerate | 0.94 |
| | Dihydroxyacetone phosphate (DHAP) | 1.8 |
| | 1,3-dihydroxacetone | 0.97 |
| | pyruvate | 1.02 |
| | lactate | 1.04 |
| | glucuronate | 0.88 |

Glucose-6-phosphate (G6P), fructose-6-phosphate (F6P), fructose-1,6-phosphate (identification based on MS/MS fragmentation and other chemical properties), and dihydroxyacetone-phosphate (DHAP) were all shown to be elevated with treatment of antimiR-208a vs. controls (G6P and F6P showed trending significance, $0.05 < p < 0.10$). This pattern is consistent with an increase in hepatic glucose metabolism following anti-miR treatment and an efficient utilization of pyruvate feeding into the tri-carboxylic acid (TCA, Krebs) cycle. A lack of change in the glycolytic end product lactate further supports an increased utilization of glucose metabolism to supply TCA cycle energetics and indicates maintenance of oxidative glucose metabolism vs. HFD controls.

Consistent with increased use of glucose-related metabolites for TCA cycle energetics, a pattern of decreased TCA cycle intermediates was observed in antimiR-208a vs. control liver samples, including α-ketoglutarate (statistically significant, $p < 0.05$), succinyl CoA and fumarate (trending significance, $0.05 < p < 0.10$), and citrate and malate (Table 7).

TABLE 7

Relative Fold Change for Metabolites in Hepatic TCA Cycle

| Sub Pathway | Biochemical | Group 1/Group 2 (relative fold of change) |
|---|---|---|
| TCA/Krebs Cycle | citrate | 0.69 |
| | alpha-ketoglutarate | 0.73 |
| | succinate | 0.99 |
| | succinylcarnitine | 1.01 |
| | succinyl CoA | 0.51 |
| | fumarate | 0.76 |
| | malate | 0.77 |
| Pantothenate and CoA metabolism | pantothenate | 0.85 |
| | phosphopantetheine | 1.33 |
| | Coenzyme A | 1.25 |
| | 3'-dephosphocoenzyme A | 1.13 |

Collectively, a decrease in the majority of TCA cycle intermediates suggests an increase in energy metabolism efficiency in the HFD model with anti-miR treatment vs. no treatment. Additionally, as TCA pathway energy metabolism is inherent to mitochondria, these changes indicate an anti-miR-mediated improvement in mitochondrial function in the HFD mouse model. Increased glucose utilization in the HFD mouse model would be advantageous, particularly in the C57Bl/6 strain which is known to be more sensitive to diet-induced dysglycemia (Gallou-Kabani et al., (2007) Obesity, 15. p. 1996-2005). Furthermore, coenzyme A (CoA) is required for α-ketoglutarate dehydrogenase-mediated conversion of α-ketoglutarate to succinyl CoA, and a pattern of increased CoA with a decrease in the CoA precursor pantothenate was also observed in the liver of animals treated with antimiR-208a vs. HFD alone. This pattern of change may reflect anti-miR-dependent release of THRAP1 (a.k.a. MED13) and a subsequent increase in mitochondrial biogenesis related to thyroid receptor signaling.

Branched-chain amino acid (BCAA) metabolism appears to play a role in the development of insulin resistance and obesity (Newgard et al., (2009) Cell Metab. 9, 311-26; Altmaier et al., (2008) Endocrinology, 149, 3478-89; She et al. (2007) Am J Physiol Endocrinol Metab, 293, E1552-63). Elevated levels of the BCAA, isoleucine, leucine and valine, are often observed during conditions of insulin resistance with various short-chain metabolites derived from the metabolism of BCAA showing a distinctive pattern of expression in association with insulin sensitivity and/or IR (Newgard et al., Altmaier et al.). The BCAAs leucine and valine were shown to be significantly decreased with anti-miR-208a treatment vs. control (p<0.05), and isoleucine trended significant decrease (0.05<p<0.10) with treatment in the HFD model (Table 8). This pattern of relative decrease with anti-miR treatment was also observed with several BCAA metabolites.

TABLE 8

Relative Fold Change for Hepatic BBCA and Metabolites

| Sub Pathway | Biochemical | Group 1/Group 2 (relative fold of change) |
|---|---|---|
| Valine, leucine and isoleucine metabolism | isoleucine | 0.91 |
| | leucine | 0.90 |
| | valine | 0.89 |
| | 2-hydroxyisobutyrate | 0.95 |
| | alpha-hydroxyisovalerate | 1.01 |
| | hydroxyisovaleroyl carnitine | 0.63 |
| | methylglutaroylcarnitine | 0.77 |

In addition to the increase in glucose metabolism and improved TCA cycle efficiency observed in the liver, further indications of anti-diabetic/obese efficacy in this organ were evident with antimiR-208a treatment vs. control. Significant alterations in maltose-derived metabolites associated with aspects of glycogen metabolism presented an indication of increased hepatic glycogen deposition following treatment with antimiR-208a. In this instance, higher glucosaccharides (i.e. maltopentaose and maltohexaose) showed statistically significant elevations (p<0.05) in response to treatment in the HFD model at one week (Table 9).

TABLE 9

Relative Fold Change for Metabolites in Hepatic Glycogen Biosynthesis

| Biochemical | Group 1/Group 2 (relative fold of change) |
|---|---|
| maltose | 0.79 |
| maltotriose | 0.87 |
| maltopentaose | 1.89 |
| maltohexaose | 2.61 |

In combination with the concurrent decrease in the shorter glucosaccharide precursors maltose (significant) and maltotriose, the observed elevation in higher glucosaccharides are assumed to be intermediates in glycogen synthesis and their elevation in association with glycogen deposition. With the apparent anti-diabetic/obese efficacy of antimiR-208a treatment in terms of elevated liver glucose metabolism and enhanced mitochondrial function, increased hepatic glycogen synthesis is consistent with an advantageous antimiR-208a effect. Increasing glycogen deposition in liver represents an effective mechanism to reduce hyperglycemia in the management of diabetes/insulin resistance. While plasma glucose levels are not substantially altered at one week following HFD+antimiR-208a vs. HFD alone (not shown, 1.09-fold control), this finding provides insight into the possible mechanism of action whereby the anti-miR affects glycemic control as the HFD model progresses.

This example demonstrates that the liver from mice treated with antimiR-208a is utilizing its preferred energy source (e.g. glycolysis) and processing excess substrate more optimally (e.g. glycogen deposition), than control mice. Further, indications are that mitochondria of the mice treated with antimiR-208a are functioning more optimally as compared to control mice (e.g. TCA cycle, branched-chain amino acids). All of these effects could be consistent with an improvement in thyroid hormone signaling which potentially could be regulated through the effects of antimiR-208a on THRAP1 (MED13).

Example 5

AntimiR-208 Promotes Improved Skeletal Muscle Fuel Utilization and Mitochondrial Function Metabolomic analysis of skeletal muscle from mice treated with high-fat diet (HFD) alone or HFD in combination with antimiR-208a (M-10101) was performed as described in Example 4. Alterations in skeletal muscle metabolism are commonly associated with metabolic disease states such as IR, T2D and MS (Muoio and Newgard, (2008) Nat Rev Mol Cell Biol, 9, 193-205; Hulver et al., (2003) Am J Physiol Endocrinol Metab, 284, E741-7).

Table 10 shows that skeletal muscle glucose metabolism upstream intermediates are elevated with anti-miR treatment while downstream triosephosphate intermediates are maintained or slightly decreased.

TABLE 10

Relative Fold Change for Metabolite in Skeletal Muscle Glucose Metabolism

| Sub Pathway | Biochemical | Group 1/Group 2 (relative fold of change) |
|---|---|---|
| Glycolysis, gluconegenesis, pyruvate metabolishm | 1,5-anhydroglucitol (1,5-AG) | 0.88 |
| | glycerate | 1.09 |
| | glucose-6-phosphate (G6P) | 2.85 |
| | glucose 1-phosphate | 2.59 |
| | glucose | 1 |
| | fructose-6-phosphate | 2.76 |
| | Isobar: fructose 1,6-diphosphate, glucose 1,6-diphosphate, myo-inositol 1,4, or 1,3-diphosphate | 1.13 |
| | 2-phosphoglycerate | 0.96 |
| | 3-phosphoglycerate | 0.92 |
| | phosphoenolpyroruvate (PEP) | 0.83 |
| | pyruvate | 0.96 |
| | lactate | 0.9 |

This pattern is again consistent with an increased use of glucose that is efficiently fed into the TCA cycle energy metabolism pathway, a pattern that is notably similar to the pattern observed in the liver samples from animals treated with anti-miR therapy vs. HFD controls (Example 4). Although these differences did not reach statistical significance, the fact that the pattern so closely reflects those differences observed in the liver with treatment supports a similar mechanism of action affecting both liver and skeletal muscle that would convey a metabolic advantage in the setting of a HFD model.

Also consistent with the anti-miR-related effects observed in liver, skeletal muscle samples showed a decrease in multiple TCA cycle intermediates relative to HFD controls including citrate (statistically significant, p<0.05), fumarate and malate (statistically significant, p<0.05) (Table 11). Again, a uniform decrease in the TCA cycle intermediates suggests a relative increase in energy metabolism efficiency with anti-miR treatment when compared to HFD controls. This pattern of difference between treatment and control groups also supports the elevated increase in the efficient use of glucose-related triosephosphate intermediates to fuel TCA cycle energetics proposed above. The combined observation that both liver and skeletal muscle display elevated glucose metabolism and increased TCA cycle efficiency with anti-miR treatment indicates a drug-related effect that may improve or at least maintain mitochondrial function, which are consistent with anti-miR-mediated release of THRAP1 (MED13) and thyroid receptor signaling to elevate mitochondrial biogenesis.

TABLE 11

Relative Fold Change for Metabolites in Skeletal Muscle TCA Cycle

| Sub Pathway | Biochemical | Group 1/Group 2 (relative fold of change) |
|---|---|---|
| TCA/Krebs Cycle | citrate | 0.72 |
| | succinylcarnitine | 0.96 |
| | fumarate | 0.86 |
| | malate | 0.79 |

Obesity and overnutrition are associated with the intramuscular accumulation of lipids and lipid metabolites that negatively correlate with insulin sensitivity (Muoio and Newgard, (2008) Nat Rev Mol Cell Biol, 9, 193-205), although the role of bioactive lipids in skeletal muscle insulin resistance is not fully understood. Lysolipids derived from glycerophospholipids (GPL) possess bioactive properties and are known to interact at multiple sites in the insulin-signaling cascade ultimately resulting in insulin resistance (Wymann and Schneiter, (2008) Nat Rev Mol Cell Biol, 9, 162-76; Patti and Kahn, (2004) Nat Med, 10, 1049-50). In this example, several lipid species were decreased in the skeletal muscle from anti-miR-treated animals when compared to HFD control samples, as shown in Table 12.

TABLE 12

Relative Fold Change for Skeletal Muscle Lysophospholipids

| Sub Pathway | Biochemical | Group 1/Group 2 (relative fold of change) |
|---|---|---|
| Lysolipid | 1-palmitoylglycerophosphoethanolamine | 0.88 |
| | 2-palmitoylglycerophosphoethanolamine* | 0.98 |
| | 1-palmitoleoylglycerophosphoethanolamine* | 0.8 |
| | 1-stearoylglycerophosphoethanolamine | 0.96 |
| | 1-oleoylglycerophosphoethanolamine | 0.82 |

TABLE 12-continued

Relative Fold Change for Skeletal Muscle Lysophospholipids

| Sub Pathway | Biochemical | Group 1/Group 2 (relative fold of change) |
|---|---|---|
| | 2-oleoylglycerophosphoethanolamine* | 0.84 |
| | 1-linoleoylglycerophosphoethanolamine* | 0.99 |
| | 2-linoleoylglycerophosphoethanolamine* | 1.35 |
| | 1-arachidonoylglycerophosphoethanolamine* | 0.84 |
| | 2-arachidonoylglycerophosphoethanolamine* | 0.95 |
| | 2-docosapentaenoylglycerophosphoethanolamine* | 0.45 |
| | 2-docosahexaenoylglycerophosphoethanolamine* | 0.41 |
| | 1-myristoylglycerophosphocholine | 0.39 |
| | 1-palmitoylglycerophosphocholine | 0.32 |
| | 2-palmitoylglycerophosphocholine* | 0.39 |
| | 1-palmitoleoylglycerophosphocholine* | 0.48 |
| | 1-stearoylglycerophosphocholine | 0.3 |
| | 1-oleoylglycerophosphocholine | 0.84 |
| | 2-oleoylglycerophosphocholine* | 0.49 |
| | 1-linoleoylglycerophosphocholine | 0.9 |
| | 2-arachidonoylglycerophosphocholine* | 0.28 |
| | 1-plamitoylglycerophosphoinositol* | 0.8 |
| | 1-stearoylglycerophosphainositol | 0.81 |
| | 1-arachidonoylglycerophosphoinositol* | 0.95 |
| | 2-arachidonoylglycerophosphoinositol* | 0.89 |
| | 1-palmitoylplasmenylethanolamine* | 0.94 |

*identification based on MS/MS fragmentation and other chemical properties

GPL-derived lysolipids in particular were uniformly decreased in skeletal muscle with anti-miR treatment vs. controls and that both ethanolamine- and choline-conjugated species were affected similarly. This difference suggests anti-miR treatment blocks a general rise in lysolipids in the HFD model, as HFD likely induces an accumulation of GPL-derived lysolipids. Also the observed pattern of decrease was not different between the sn-1 and sn-2 variants of lysolipids, indicating that anti-miR treatment was not preferentially affecting phospholipase A1 or A2, further supporting anti-miR-induced changes in lysolipid uptake in the HFD model vs. biosynthetic changes.

Additionally, anti-miR treatment also decreased skeletal muscle mono- and di-acylglycerols as well as sphingolipids (Table 13), which is consistent with suggesting that HFD correlates with a general increase in skeletal muscle accumulation of lipids and lipid metabolites. Thus, as for glucose metabolism and increased TCA cycle efficiency (mitochondrial function), the uniform pattern of change observed in lysolipid levels following anti-miR treatment is indicative of therapeutic efficacy for conveying preservation of skeletal muscle insulin sensitivity.

TABLE 13

Relative Fold Change for Skeletal Muscle Mono- and Di-Acylglycerols

| Sub Pathway | Biochemical | Group 1/Group 2 (relative fold of change) |
|---|---|---|
| Monoacylglycerol | 1-palmitoylglycerol* (1-monopalmitin) | 0.75 |
| | 2-palmitoylglycerol (2-monopalmitin) | 0.79 |
| | 1-stearoglycerol (1-monostearin) | 0.8 |
| Diacylglycerol | 1,2-dipalmitoylglycerol | 0.71 |
| | 1,3-dipalmitoylglycerol | 0.51 |
| Sphingolipid | sphingosine | 0.51 |
| | palmitoyl sphingomyelin* | 0.79 |
| | stearoyl sphingomyelin | 0.85 |

*statistically significant (p < 0.05)

These results demonstrate anti-miR208a treatment concurrent with HFD resulted in improved skeletal muscle fuel utilization (glycolysis) and mitochondrial function (TCA cycle). In addition, there may be a decrease in intra-skeletal muscle fat deposition. Thus, administration of anti-miR208a can improve skeletal muscle metabolism which may also be mediated through increased thyroid hormone receptor signaling with anti-miR208a-facilitated THRAP1 (MED13) expression.

Example 6

AntimiR-208 Promotes Cardiac Metabolism

Metabolomic analysis of the hearts from mice treated with high-fat diet (HFD) alone or HFD in combination with antimiR-208a (M-10101) was performed as described in Example 4.

Cardiac muscle utilizes multiple fuel substrates, with fatty acids and glucose as predominant substrates, and fatty acids as its preferred fuel source. Concurrent treatment of mice with anti-miR208a at the start of diet administration over one week resulted in a pattern of elevated long-chain fatty acids (LCFA) when compared to HFD atone (Table 14), in which the change of vaccenate, eicosenoate, dihomolinoleate, and docosadienoate were statistically significant ($p<0.05$).

TABLE 14

Relative Fold Change for Cardiac Long Chain Fatty Acids

| Sub Pathway | Biochemical | Group 1/Group 2 (relative fold of change) |
|---|---|---|
| Long chain fatty acid | rnyristate (14:0) | 1.08 |
| | myristoleate (14:1n5) | 1.11 |
| | pentadecanoate (15:0) | 0.99 |
| | palmitate (16:0) | 1.09 |
| | palmitoleate (16:1n7) | 1.14 |
| | margarate (17:0) | 1.1 |
| | 10-heptadecenoate (17:1n7) | 1.1 |
| | stearate (18:0) | 1.14 |
| | oleate (18:1n9) | 1.11 |
| | cis-vaccenate (18:1n7) | 1.14 |
| | stearidonate (18:4n3) | 0.8 |
| | nonadecanoate (19:0) | 1.08 |
| | 10-nonadecenoate (19:1n9) | 1.08 |
| | eicosenoate (20:1n9 or 11) | 1.22 |
| | dihomolinoleate (20:2n6) | 1.18 |
| | mead acid (20:3n9) | 1.08 |
| | arachidonate (20:4n6) | 1.07 |
| | docosadienoate (22:2n6) | 1.21 |
| | docosatrienoate (22:3n3) | 1.31 |
| | adrenate (22:4n6) | 1.12 |

This difference suggests an increase in cardiac uptake of its preferred fuel source with anti-miR treatment. Unlike pathologic conditions where FA oxidation becomes overwhelmed and ketone body formation ensues, the increase in cardiac LCFA levels with anti-miR treatment correlated with a relative decrease in cardiac ketone body levels (an anti-miR-dependent decrease in the ketone body 3-hydroxybutyrate (BHBA)), when compared to controls. This may reflect a more efficient use of the preferred FA fuel substrates in heart with antimiR-208a treatment.

Unlike skeletal muscle which showed a general decrease in most lipid species, treatment with anti-miR was related to a general increase in several cardiac lipid species pith 2-stearoyl-GPC and 2-stearoylglycerol statistically significant ($p<0.05$), and 1-linoeoyl-GPE showing trending significance ($0.05<p<0.1$)) in addition to LCFAs including lysolipids, mono- and di-acylglycerols, and sphingolipids (Table 15). These data collectively would suggest an anti-miR-208a-related increase in cardiac lipids that relate to improved metabolic efficiency in the HFD model, perhaps secondary to THRAP1 (MED13)-mediated mitochondrial biogenesis.

TABLE 15

Relative Fold Change for Cardiac Lysolipids and Mono- and Di-Acylglycerols

| Sub Pathway | Biochemical | Group 1/Group 2 (relative fold of change) |
|---|---|---|
| Lyoslipid | 1-linoleoylglycerophos-phoethanolamine* | 1.49 |
| | 1-stearoylglycerophosphocholine* | 1.52 |
| | 1-linoleoylglycerophosphocholine | 1.45 |
| | 1-oleoylglycerophosphoinositol* | 1.22 |
| Monoacyl-glycerol | 1-palmitoylglycerol (1-monopalmitin) | 1.08 |
| | 2-palmitoylglycerol (2-monopalmitin) | 1.11 |
| | 1-stearoglycerol (1-monostearin) | 1.16 |
| | 2-stearoglycerol (2-monostearin) | 1.28 |
| | 1-oleoylglycerol (1-monoolein) | 1.1 |
| | 2-oleoylglycerol (2-monoolein) | 1.86 |
| | 2-linoleoylglycerol (2-monolinolein) | 1.15 |
| Diacylglycerol | 1,2-dipalmitoylglycerol | 1.12 |
| | 1,3-dipalmitoylglycerol | 1.08 |
| Sphingolipid | sphinganine | 1.16 |
| | sphingosine | 1.25 |
| | palmitoyl sphingomyelin | 0.99 |
| | stearoyl sphingomyelin | 0.99 |

*identification based on MS/MS fragmentation and other chemical properties

In addition to increased uptake of its preferred lipid fuel substrates, heart samples from anti-miR-treated animals also showed an elevation in several intermediates of the glycolytic pathway including glucose-6-phosphate, pyruvate and the end product of glycolysis lactate (statistically significant vs. control) (Table 16).

TABLE 16

Relative Fold Change for Metabolites in Cardiac Glucose Metabolism

| Sub Pathway | Biochemical | Group 1/Group 2 (relative fold of change) |
|---|---|---|
| Glycolysis, gluconegenesis, pyruvate metabolishm | glucose-l-phosphate | 1.91 |
| | glucose-6-phosphate (G6P) | 1.28 |
| | 2-phosphoglycerate | 0.9 |
| | 3-phosphoglycerate | 0.92 |
| | pyruvate | 1.3 |
| | lactate | 1.26 |

While this pattern is slightly different from that observed with liver and skeletal muscle, which showed no elevation in lactate, these differences are not surprising given the differences in preferred fuel sources that exist between cardiac muscle, skeletal muscle and liver and alternative lactate producing pathways in the heart. Collectively, however, these data support an increase in the metabolism of primary fuel sources utilized by the heart (lipids and glucose) that may also be related to improved metabolic efficiency associated with elevate THRAP1 (MED13)-induced mitochondrial biogenesis with antimiR-208a treatment vs. HFD controls.

Another biochemical signature that distinguished cardiac glucose metabolism from that of the liver is a significant increase in the glycogen breakdown product glucose-1-phosphate, which is produced via phosphorylase activity and shuttles glycogen metabolites into the glycolytic pathway (Salway, *Metabolism at a glance*. Third Edition ed. 2004, Malden, Mass.: Blackwell Publishing. 125; Stryer, L., *Biochemistry*. Fourth Edition ed, 1995, New York, N.Y.: W.H. Freeman and Co. 1064.) This is in contrast to what would be expected in a HFD, where in the fed state glycogen synthesis would preferentially occur over glycogenolysis, suggesting a unique metabolic impact of anti-miR in the HFD model heart. Overall, however, these data indicate an increase in cardiac fuel metabolism associated with antimiR-208a efficacy that suggests improved carbon handling in the context of the HFD model.

As with the liver and skeletal muscle, which both displayed differences in TCA cycle intermediates consistent with improved metabolic efficiency, the heart from animals treated with anti-miR also showed changes in TCA cycle intermediates vs. HFD controls. Not surprisingly, the differences observed in cardiac fuel metabolism vs. the other tissues were extended to differences observed in cardiac TCA cycle changes, in relation to those observed in liver or skeletal muscle (Table 17).

TABLE 17

Relative Fold Change for Metabolites in Cardiac TCA Cycle

| Sub Pathway | Biochemical | Group 1/Group 2 (relative fold of change) |
|---|---|---|
| TCA/Krebs Cycle | citrate | 1.55 |
| | succinate | 0.77 |
| | succinylcarnitine | 1.06 |
| | fumarate | 1.3 |
| | malate | 1.09 |
| Pantothenate and CoA metabolism | pantothenate | 0.93 |
| | phosphopantetheine | 0.94 |
| | coenzyme A | 1.53 |
| | 3'-dephosphocoenzyme A | 1.4 |
| | acetyl CoA | 1.51 |

Citrate was significantly elevated in heart tissues from anti-miR-treated animals vs. controls, as was fumarate. Citrate, which can be exported from the mitochondria by the tricarboxylate carrier, can subsequently be used as a fatty acid synthesis precursor via acetyl- and malonyl-CoA intermediates (Salway, *Metabolism at a glance*. Third Edition ed. 2004, Malden, Mass.: Blackwell Publishing. 125). Fatty acid uptake appeared to be elevated in the heart of antimiR-208a-treated animals, and an increase in FA uptake may offset the need for FA synthesis resulting in an accumulation of FA precursors like citrate. Additionally, the conversion of succinate to fumarate is coupled with complex II production of $FADH_2$ in the electron transport chain. A significant decrease in succinate (statistically significant, $p<0.05$) and a concordant significant increase in fumarate (statistically significant, $p<0.05$) in the hearts of animals treated with anti-miR vs. controls indicate a more efficient utilization of this biochemical correlating with more efficient electron transport and oxidative phosphorylation, and thus, mitochondrial function. The fatty acid oxidation end product acetyl CoA and coenzyme A, both increased in the hearts of animals treated with antimiR-208a as compared to controls, as shown in Table 17, which correlate with increased FA metabolism and mitochondrial function.

As inhibition of miR-208a with M-10101 releases the inhibitory effects of miR-208a on THRAP1 (MED13), and hence TR signaling, oxidative phosphorylation would increase. Which is consistent with the antimiR-208a-related changes described herein. Inhibition of complex II of the electron transport chain is associated with increased reactive oxygen species (ROS) and autophagic cell death, suggesting that improved efficiency of complex II may be related to improved redox balance in the hearts of HFD animals treated with antimiR-208a (Chen et al., (2007) J Cell Sci, 120, 4155-66).

Example 7

Plasma Analysis Shows antimiR-208 Promotes Increased Fuel Utilization, Lipid Handling and Mitochondrial Function Metabolomic analysis of plasma from the mice treated with high-fat diet (HFD) alone or HFD in combination with antimiR-208a (M-10101) was performed as described in Example 4.

Plasma provides biochemical signatures of endogenous metabolism within the blood compartment, as well as metabolites altered or produced from events occurring throughout the host. The detection of multi-source metabolites provides a highly informative data set reflective of systemic events related to a given treatment or process being studied. While metabolite changes detected in plasma alone typically do not reveal precisely what is occurring in a specific tissue or organ system, they can provide additional support as to organ-specific biochemical events.

Consistent with the early signs of increased FA metabolism resulting from anti-miR treatment of the HFD model, several medium-Chain fatty acids (MCFA) were elevated, such as heptanoate and undecanoate, both statistically significant ($p<0.05$) and caprylate and pelargonate, both showing trending significance ($0.05<p<0.10$), in the serum of antimiR-208a-treated animals vs. untreated controls (Table 18).

TABLE 18

Relative Fold Change for MCFA in Plasma

| Sub Pathway | Biochemical | Group 1/Group 2 (relative fold of change) |
|---|---|---|
| Medium chain fatty acid | isocaproate | 1.27 |
| | caproate (6:0) | 0.93 |
| | heptanoate (7:0) | 1.22 |
| | caprylate (8:0) | 1.23 |
| | pelargonate (9:0) | 1.21 |
| | caprate (10:0) | 1.21 |
| | undecanoate (11:0) | 1.41 |
| | laurate (12:0) | 1.17 |

Unlike long-chain fatty acids (LCFA) which typically require acylcarnitine conjugation to facilitate their entry into the mitochondria via palmitoyl-carnitine transferase I (CPT-I), MCFA are able to translocate into the mitochondria without this conjugation step making them more readily available fuel substrates than their LCFA counterparts. An increase in plasma MCFA is thought to correlate with the earliest signs of lipolysis. The observed changes in plasma MCFA likely reflect a beneficial biochemical trend of FA mobilization and increased metabolism related to anti-miR efficacy in the mouse HFD model.

Postprandial elevations of plasma bile acids (BA), particularly with high-fat meals, are known to occur in normal weight subjects, which has been shown to improve glycemic control and energy metabolism through BA-mediated activation of multiple receptors (Glicksman et al., (2010) Ann Clin Biochem. 47, 482-4). Although it is not possible to discern BA changes associated with the HFD in this example, when compared to HFD alone the addition of anti-miR to HFD for one week caused a uniform decrease in plasma bile acids for all species detected (Table 19).

TABLE 19

Relative Fold Change for Bile Acid Metabolites in Plasma

| Sub Pathway | Biochemical | Group 1/Group 2 (relative fold of change) |
|---|---|---|
| Bile acid metabolism | cholate | 0.91 |
| | taurocholate | 0.13 |
| | taurochenodeoxycholate | 0.11 |
| | deoxycholate | 0.2 |
| | taurodeoxycholate | 0.22 |
| | beta-muicholate | 0.42 |
| | tauro-beta-muricholate | 0.11 |
| | alpha-murichoalte | 0.37 |
| | tauroursodeoxycholate | 0.1 |

All BA species were decreased in Group 1 (i.e. antimiR-208a+HFD). This result lends confidence to an antimiR-208a-specific effect in the HFD model. A uniform decrease in BA levels may correlate with an increased ability of the animals receiving drug to handle the elevated nutritional input (i.e. increased mitochondria metabolic capacity), thereby decreasing the need for elevated plasma BA as a means to eliminate FA from the system. Alternatively, as mentioned above, BA signaling is known to improve glycemic control and energy metabolism (Glicksman et al., (2010) Ann Clin Biochem. 47, 482-4). Hence, the anti-miR-related observations noted above with respect to increased glucose metabolism (liver, heart, skeletal muscle), hepatic glycogen synthesis, improve cardiac FA metabolism and broad improvement in mitochondrial function in multiple tissues would indicate a decreased need for BA signaling to resolve impaired metabolic issues related to the early HFD phenotype (or developing issues, as the case may be).

One of the hallmarks of mitochondrial dysfunction is an elevation in acylcarnitine intermediates of FA oxidation (FA-AC), particularly in the face of overnutrition where elevated FA substrates overwhelm the ability mitochondria to efficiently handle FA metabolically (Muoio and Newgard, (2008) Nat Rev Mol Cell Biol., 9, 193-205). Several lines of evidence presented thus far indicate an improvement in mitochondrial function in the liver, skeletal muscle and heart (Examples 4-7). Plasma FA-AC levels were decreased in animals receiving anti-miR treatment while on HFD when compared to those on HFD alone (Table 20), further supporting a drug-related improvement in mitochondrial function in the HFD model.

TABLE 20

Relative Fold Change for Carnitine Metabolites in Plasma

| Sub Pathway | Biochemical | Group 1/Group 2 (relative fold of change) |
|---|---|---|
| Carnitine metabolism | deoxycarnitine | 1.21 |
| | carnitine | 1.18 |
| | 3-dehydrocarnitine* | 1.03 |

TABLE 20-continued

Relative Fold Change for Carnitine Metabolites in Plasma

| Sub Pathway | Biochemical | Group 1/Group 2 (relative fold of change) |
|---|---|---|
| | acetylcarnitine | 0.94 |
| | hexanoylcarnitine | 0.99 |
| | octanoylcarnitine | 0.88 |
| | laurylcarnitine | 0.74 |
| | palmitoylcarnitine | 0.69 |
| | stearoylcarnitine | 0.75 |
| | oleoylcarnitine | 0.7 |

MiR-208a negatively regulates THRAP1 (MED13), potentially having a negative impact on TR-mediated mitochondrial biogenesis. The observed decrease in plasma FA-AC along with the notable changes in multi-tissue TCA cycle energetics strongly supports the concept of anti-miR-related release of THRAP1 (MED13) inhibition and a subsequent increase in mitochondrial biogenesis, which would manifest as an improved mitochondrial function signature consistent with the observations described herein.

Accordingly, biochemical alterations within the plasma from anti-miR208a treated mice in the setting of a HFD suggest that there is an increase in fuel utilization, lipid handling and mitochondrial function. This is can also be consistent with a THRAP1 (MED13)-mediated increase in thyroid hormone receptor signaling.

Example 8

AntimiR-208 Promotes Redox-Homeostasis

Metabolomic analysis for glutathione metabolites was performed on the liver, skeletal muscle, and heart from mice treated with high-fat diet (HFD) alone or HFD in combination with antimiR-208a (M-10101) as described in Example 4. Glutathione plays an important role in redox-homeostasis, antioxidant defense, protein folding and detoxification of drugs, with reduced glutathione (GSH) representing the active form of this tripeptide imposing a substantial influence on redox balance. The thiol group of glutathione can react with electrophiles to generate GSH adducts and glutathione-S-transferases (GST) conjugate GSH with toxins and drug metabolites to form water-soluble products for excretion.

Liver from animals treated with anti-miR showed significantly elevated GSH levels in addition to elevations in several glutathione metabolites vs. control levels, indicating improved hepatic redox balance with antimiR-208a treatment vs. HFD alone (Table 21). Cysteine-glutathione disulfide is a common biomarker of oxidative stress used in global metabolomic analyses. Consistent with the notion of drug-induced redox improvement over HFD alone, hepatic cysteine-glutathione disulfide was decreased with anti-miR treatment when compared to controls. While elevated GSH levels could reflect increased glutathione synthesis, the upstream intermediates of glutathione biosynthesis were largely unaffected by anti-miR treatment (not shown). This observation suggests that elevated hepatic GSH levels correlate with altered glutathione reduction and/or glutathione recycling.

TABLE 21

Relative Fold Change for Metabolite in Hepatic Glutathione Metabolism

| Sub Pathway | Biochemical | Group 1/Group 2 (relative fold of change) |
|---|---|---|
| Glutathione metabolism | glutathione, reduced (GSH) | 1.71 |
| | S-methylglutathione | 1.51 |
| | 5-oxoproline | 1.06 |
| | glutathione, oxidized (GSSG) | 0.99 |
| | cysteine-glutathione disulfide | 0.77 |
| | ophthalmate | 1.21 |
| | S-lactolglutathione | 1.88 |

One change observed in the glutathione metabolism pathway that positively correlated with antimiR-208a treatment was an elevation in S-lactoylglutathione (1.88-fold HFD alone). GSH regeneration is linked to glucose metabolism via the degradation pathway of triosephosphate intermediates. Upstream intermediates of glucose metabolism were elevated in the liver of antimiR-208a treated animals, while the triosephosphate intermediates of glucose metabolism appeared unaffected. This would suggest, in addition to an efficient utilization of glucose-derived pyruvate for TCA cycle energetics, triosephosphate degradation may be occurring with antimiR-208a treatment, which is connected to GSH regeneration via glyoxylase-mediated restoration of glutathione from S-lactoylglutathione. Consequently, the anti-miR-mediated increase in glucose metabolism may contribute, at least in part, to the increase in GSH Observed with antimiR-208a vs. controls.

As described in Example 5 above, skeletal muscle showed a similar pattern of glucose metabolism intermediates as those found in liver in the context of antimiR-208a+HFD vs. HFD alone, including elevated upstream intermediates and apparently no change in the triosephosphate intermediates. Not surprisingly then, skeletal muscle from animals treated with drug also showed a significant increase in GSH when compared to controls (Table 22), and this increase correlated with an increase in S-lactoylglutathione (1.67-fold HFD alone).

TABLE 22

Relative Fold Change for Metabolite in Skeletal Muscle Glutathione Metabolism

| Sub Pathway | Biochemical | Group 1/Group 2 (relative fold of change) |
|---|---|---|
| Glutathione metabolism | glutathione, reduced (GSH) | 1.44 |
| | 5-oxoproline | 0.73 |
| | glutathione, oxidized (GSSG) | 1 |
| | cysteine-glutathione disulfide | 1.04 |
| | ophthalmate | 1.27 |
| | S-lactolglutathione | 1.67 |

Unlike the liver, which showed a slight decrease in the oxidative stress marker cysteine-glutathione disulfide, skeletal muscle samples from antimiR-208a treated animals showed no change in this biochemical, potentially indicating a difference in tissue specific changes in redox balance related to the HFD model. These data further support an anti-miR-related effect on glucose metabolism that is coordinated with both enhanced TCA cycle energetics and GSH recycling in the liver and skeletal muscle, all consistent with antimiR-208a efficacy in the early stages of diet-induced metabolic changes.

Unlike the liver and skeletal muscle, the heart showed a slight increase in GSH levels with antimiR-208a treatment vs. HFD controls, with no detection of S-lactoylglutathione (Table 23).

TABLE 23

Relative Fold Change for Metabolite in Cardiac Glutathione Metabolism

| Sub Pathway | Biochemical | Group 1/Group 2 (relative fold of change) |
|---|---|---|
| Glutathione metabolism | glutathione, reduced (GSH) | 1.19 |
| | 5-oxoproline | 1.02 |
| | glutathione, oxidized (GSSG) | 1.01 |
| | cysteine-glutathione disulfide | 1.21 |

As described in Example 6 above, heart metabolism is different than metabolism in the liver or skeletal muscle and differences in FA uptake/metabolism, glucose metabolism, lactate production and TCA cycle energetics were observed. Since the S-lactoylglutathione/glyoxylase regeneration of glutathione is dependent on triosephosphate degradation and this was observed in liver and skeletal muscle, this pathway may not contribute to the elevation of GSH observed in the heart. However, also mentioned above was the notable increase in cardiac lactate and concurrent decrease in pyruvate, which appears to be associated with an increase in the malate/oxaloacetate shuttle; providing a potential mechanism of improved cytosolic redox status in the hearts of animals treated with drug vs. untreated HFD controls.

The cardiac muscle engages metabolic pathways that distinguish it from other tissues, including the malate-oxaloacetate shuttle (Strong et al., (1979) Eur J Biochem, 102, 625-36), where malate is exported from the mitochondria into the cytosol and its conversion to oxaloacetate is coupled to the conversion of pyruvate to lactate, and cycling of NAD+/NADH. This shuttle has been proposed as a possible mechanism to regulated redox-homeostasis in cardiomyocytes by potentially countering the cytosolic oxidation associated with the malate-aspartate shuttle (Strong et al). This potential mechanism to maintain redox balance in the HFD model via antimiR-208a treatment may account for, at least in part, the differences observed in glutathione metabolism between treated and un-treated samples noted below, and mechanistic differences observed among heart, liver and skeletal muscle for the reconstitution of reduced glutathione (GSH) that occurs with antimiR-208a treatment.

Analysis of the metabolites as described in Examples 4-7 showed that relative to controls on HFD for one week, anti-miR treatment in combination with HFD for one week resulted in a limited number of significant biochemical changes may demonstrate a degree of advantageous metabolic differences with anti-miR administration. Tissue specific patterns of biochemical changes revealed an improvement of mitochondrial function related to elevations in liver and muscle glycolysis and elevated fatty acid uptake and metabolism in the heart as a primary consequence of antimiR treatment in the HFD model. These results were also supported by differences in plasma biomarkers suggesting improved mitochondrial function. Additionally, in response to antimiR-208a treatment, an improvement or preservation of redox-homeostasis in the liver, muscle and heart was evident as well as increased hepatic glycogen synthesis. No significant changes were observed in retroperitoneal fat, which is consistent with the short duration of the HFD and/or combined HFD+antimiR-208a treatment in a C57Bl/6 mouse model.

Example 9

AntimiR-208 Promotes Dipeptide Accumulation

Metabolomic analysis for dipeptides was performed on the skeletal muscle from mice treated with high-fat diet (HFD) alone or HFD in combination with antimiR-208a (M-10101) as described in Example 4. Amino acid dipeptides can be used as building blocks for protein synthesis, and hence muscle growth. Treatment of HFD animals with anti-miR caused an increase in several skeletal muscle dipeptides levels (15 increased of 20 identified, 5 of 20 with statistical significance, p<0.05, and 3 others trending significance) (Table 24).

TABLE 24

Relative Fold Change for Metabolite in Cardiac Glutathione Metabolism

| Sub Pathway | Biochemical | Group 1/Group 2 (relative fold of change) |
|---|---|---|
| Dipeptide | glycylvaline | 1.24 |
| | glycylleucine | 1.2 |
| | alanylvaline | 2.01 |
| | alanylleucine | 1.2 |
| | alanyltryosine | 1.63 |
| | prolylleucine | 1.15 |
| | leucylleucine | 0.86 |
| | valylleucine | 1.89 |
| | histidylleucine | 0.94 |
| | isoleucylalanine | 1.05 |
| | isoleucylglycine | 0.93 |
| | isoleucylserine | 1.31 |
| | leucylalanine | 1.45 |
| | leucylglycine | 1.37 |
| | leucylserine | 1.24 |
| | lysylleucine | 1.32 |
| | phenylalanylserine | 1 |
| | serylleucine | 1.64 |
| | serylphenylalanine | 1.41 |
| | threonylleucine | 2.14 |

A broad increase in skeletal muscle dipeptides possibly indicates inhibition of skeletal muscle growth, resulting in the accumulation of the dipeptide building blocks. Thus, antimiR, 208a may alter skeletal muscle protein synthesis.

The invention claimed is:

1. A method of treating obesity, hypercholesterolemia, type 2 diabetes, hepatic steatosis, hyperlipidemia, insulin resistance, a glycogen storage disease, or aberrant glucose uptake and/or utilization in a subject in need thereof comprising administering to the subject an inhibitor of miR-208a and/or miR-208b, wherein the inhibitor is an antisense oligonucleotide, wherein the antisense oligonucleotide comprises a sequence that is at least partially complementary to a mature sequence of miR-208a and/or miR-208b, and wherein the expression or activity of miR-208a and/or miR-208b is reduced in the cells of the subject following administration.

2. The method of claim 1, wherein the antisense oligonucleotide comprises a sequence that is at least partially complementary to SEQ ID NO: 9 or SEQ ID NO: 11.

3. The method of claim 1, wherein the antisense oligonucleotide comprises at least one sugar and/or backbone modification.

4. The method of claim 3, wherein the sugar modification is a locked nucleic acid, a 2'-O-alkyl modification, or a 2'-halo modification.

5. The method of claim 4, wherein the 2'-halo modification is a 2'-fluoro modification.

6. The method of claim 3, wherein the backbone modification is a phosphorothioate linkage.

7. The method of claim 1, wherein the antisense oligonucleotide is about 6 to about 22 nucleotides in length.

8. The method of claim 1, wherein the antisense oligonucleotide has a sequence of SEQ ID NO:3 or SEQ ID NO:4.

9. The method of claim 8, wherein the antisense oligonucleotide has the structure of Compound 10101 (SEQ ID NO: 13), 10673 (SEQ ID NO: 18), 10674 (SEQ ID NO: 19), 10677 (SEQ ID NO: 20), 10679 (SEQ ID NO: 21), 10707 (SEQ ID NO: 26), 10680 (SEQ ID NO: 22), 10681 (SEQ ID NO: 23), or 10683 (SEQ ID NO: 25).

10. The method of claim 1, wherein the subject is human.

11. The method of claim 1, wherein the inhibitor is administered to the subject by an intradermal, subcutaneous, intramuscular, intraperitoneal or intravenous route of administration.

12. The method of claim 1, wherein the antisense oligonucleotide contains at least 9 locked nucleotides.

13. A method of regulating fatty acid or glucose metabolism in a subject in need thereof comprising administering an inhibitor of miR-208a and/or miR-208b expression or activity to the subject, wherein the inhibitor of miR-208a and/or miR-208b is an antisense oligonucleotide comprising a sequence that is at least partially complementary to a mature sequence of miR-208a and/or miR-208b.

14. The method of claim 13, wherein fatty acid or glucose metabolism is increased in the subject following administration of the inhibitor as compared to a subject not administered the inhibitor.

15. The method of claim 13, wherein the cell is a cardiomyocyte, a skeletal muscle cell, a preadipocyte, an adipocyte, or a hepatocyte.

16. The method of claim 13, wherein the cell is in vitro or in vivo.

17. The method of claim 13, wherein the antisense oligonucleotide contains at least 9 locked nucleotides.

18. A method of enhancing mitochondrial function or redox-homeostasis in a subject in need thereof comprising administering to the subject an antisense oligonucleotide comprising a sequence that is at least partially complementary to a miR-208a or miR-208b sequence, wherein the expression or activity of milt-208a or miR-208b is reduced in the cells of the subject following administration of the antisense oligonucleotide.

19. The method of claim 18, wherein the antisense oligonucleotide contains at least 9 locked nucleotides.

* * * * *